(12) United States Patent
Anderson et al.

(10) Patent No.: US 9,867,869 B2
(45) Date of Patent: Jan. 16, 2018

(54) INSULIN DERIVATIVES FOR DIABETES TREATMENT

(71) Applicants: Massachusetts Institute of Technology, Cambridge, MA (US); The Children's Medical Center Corporation, Boston, MA (US)

(72) Inventors: Daniel G. Anderson, Sudbury, MA (US); Hung-Chieh Chou, Cambridge, MA (US); Michael J. Webber, Cambridge, MA (US); Benjamin C. Tang, Cambridge, MA (US); Yair Levi, Halfa (IL); Yunlong Zhang, Cambridge, MA (US); Rosemary Lynn Kanasty, Cambridge, MA (US); Arturo Jose Vegas, Cambridge, MA (US); Robert S. Langer, Newton, MA (US)

(73) Assignees: Massachusetts Institute of Technology, Cambridge, MA (US); The Children's Medical Center Corporation, Boston, MA (US)

( * ) Notice: Subject to any disclaimer, the term of this patent is extended or adjusted under 35 U.S.C. 154(b) by 37 days.

(21) Appl. No.: 14/652,011

(22) PCT Filed: Dec. 12, 2013

(86) PCT No.: PCT/US2013/074794
§ 371 (c)(1),
(2) Date: Jun. 12, 2015

(87) PCT Pub. No.: WO2014/093696
PCT Pub. Date: Jun. 19, 2014

(65) Prior Publication Data
US 2015/0320837 A1    Nov. 12, 2015

Related U.S. Application Data

(60) Provisional application No. 61/736,079, filed on Dec. 12, 2012, provisional application No. 61/736,092, filed on Dec. 12, 2012, provisional application No. 61/736,109, filed on Dec. 12, 2012.

(51) Int. Cl.
| | | |
|---|---|---|
| *A61K 38/28* | (2006.01) | |
| *A61K 47/48* | (2006.01) | |
| *G01N 33/66* | (2006.01) | |
| *G01N 33/74* | (2006.01) | |

(52) U.S. Cl.
CPC ........ *A61K 38/28* (2013.01); *A61K 47/48023* (2013.01); *A61K 47/48038* (2013.01); *A61K 47/48046* (2013.01); *A61K 47/48092* (2013.01); *A61K 47/48123* (2013.01); *G01N 33/66* (2013.01); *G01N 33/74* (2013.01); *G01N 2333/62* (2013.01)

(58) Field of Classification Search
CPC ........ A61K 38/28; A61K 38/00; A61K 38/22; A61K 47/28; A61K 47/42; A61K 31/69
See application file for complete search history.

(56) References Cited

U.S. PATENT DOCUMENTS

| 4,916,212 A | 4/1990 | Markussen |
|---|---|---|
| 2003/0018684 A1 | 1/2003 | Ohsawa |

FOREIGN PATENT DOCUMENTS

| EP | 214826 | 2/1987 |
|---|---|---|
| EP | 272097 | 6/1988 |
| EP | 375437 | 6/1990 |
| EP | 383472 | 8/1990 |
| WO | 9726265 | 7/1997 |
| WO | 9808871 | 3/1998 |
| WO | 9903861 | 1/1999 |
| WO | 9901423 | 4/1999 |
| WO | 0037474 | 6/2000 |
| WO | 0039088 | 7/2000 |
| WO | 0042026 | 7/2000 |
| WO | 0192334 | 12/2001 |
| WO | 03048195 | 6/2003 |
| WO | 2011000823 | 1/2011 |

OTHER PUBLICATIONS

Zhang et al., J. Mater. Chem., 2012, 22, 16299, published on Jul. 3, 2012.*
Agard, et al., "A strain-promoted [3 +2] azide-alkyne cycloaddition for covalent modification of biomolecules in living systems", J Am Chem Soc., 126:15046-7 (2004).
Akinc, et al., "A combinatorial library of lipid-like materials for delivery of RNAi therapeutics", Nat Biotechnol., 26 (5):561-9 (2008).
Akinc, et al., "Targeted delivery of RNAi therapeutics with endogenous and exogenous ligand-based mechanisms", Mol Ther., 18 (7):1357-64 (2010).
Astriab-Fisher, et al., "Antisense inhibition of P-glycoprotein expression using peptide-oligonucleotide conjugates", Biochem Pharmacol., 60 (I):83-90 (2000).
Astriab-Fisher, et al., "Conjugates of antisense oligonucleotides with the Tat and antennapedia cell-penetrating peptides: effects on cellular uptake; binding to target sequences, and biologic actions", Pharm Res., 19 (6):744-54 (2002).
Author Unknown, "The effect of intensive treatment of diabetes on the development and progression of long-term complications in Insulin-dependent diabetes mellitus. The Diabetes Control and Complications Trial Research Group", N. Engl J Med., 329;977-986 (1993).

(Continued)

*Primary Examiner* — Kaipeen Yang
(74) *Attorney, Agent, or Firm* — Pabst Patent Group LLP

(57) ABSTRACT

Compounds, compositions, and methods for "smart" delivery of a therapeutic, prophylactic or diagnostic agent, such as glucose-mediated delivery of insulin through glucose-sensing insulin derivatives, are provided. The insulin derivatives bind serum albumin or agglomerate in vivo. The insulin derivatives effectively dissociate to release insulin in a hyperglycemic condition, where the complexation of glucose to a glucose-sensing element alters properties of the insulin derivative leading to the dissociation. The compounds, compositions, and methods provide a delivery strategy for both self-regulated and long-term diabetes management.

18 Claims, 35 Drawing Sheets

(56) References Cited

OTHER PUBLICATIONS

Baudys, et al., "Extending Insulin Action in Vivo by Conjugation to Carboxymethyl Dextran", Bioconjugate Chem., 9:176-183 (1998).
Berman, "Insulin kinetics, models, and delivery schedules", Diabetes Care, 3:266-9 (1980).
Browning, et al., "Prevalence of hepatic steatosis in an urban population in the United States: Impact of ethnicity", Hepatology, 40 (6):1387-95 (2004).
Caplen, et al., "Specific inhibition of gene expression by small double-stranded RNAs in invertebrate and vertebrate systems", PNAS, 98 (17):9742-7 (2001).
Cesarone, et al., "Insulin receptor substrate 1 knockdown in human MCF7 ER+ breast cancer cells by nuclease-resistant IRS1 siRNA conjugated to a disulfide-bridged D-peptide analogue of Insulin-like growth factor I", Bioconjug Chem., 18 (6):1831-40 (2007).
Chiu, et al., "Visualizing a correlation between siRNA localization, cellular uptake, and RNAi in living cells", Chem Biol., 11 (8):1165-75 (2004).
Chu, et al., "Aptamer mediated siRNA delivery", Nucleic Acids Res., 34 (10):e73 (2006).
Chu, et al., "In vitro and in vivo testing of glucose-responsive insulin-delivery microdevices in diabetic rats", Lab Chip, 12:2533-9 (2012).
Cramer and Pugh, The influence of insulin use on glycemic control: How well do adults follow prescriptions for insulin\, Diabetes Care, 28(1):78-83 (2005).
Damge, et al., "Nanoparticle strategies for the oral delivery of insulin", Expert Opin. Drug Delivery, 5:45-68 (2008).
Davidson, et al., "Highly efficient small interfering RNA delivery to primary mammalian neurons induces MicroRNA-like effects before mRNA degradation", J Neurosci., 24 (45): 10040-6 (2004).
Davis, et al., "Evidence of RNAi in humans from systemically administered siRNA via targeted nanoparticles", Nature, 464 (7291): 1067-70 (2010).
Dorsett,et al., "siRNAs: applications in functional genomics and potential as therapeutics", Nat Rev Drug Discov, 3 (4):318-29 (2004).
Elbashir, et al., "Duplexes of 21-nucleotide RNAs mediate RNA interference in cultured mammalian cells", Nature, 411 (6836): 494-8 (2001a).
Elsayed, et al., "Chitosan-sodium lauryl sulfate nanoparticles as a carrier system for the in vivo delivery of oral insulin", AAPS PharmSciTech., 12:958-64 (2011).
Esposito and Giugliano, "Current insulin analogues in the treatment of diabetes: emphasis on type 2 diabetes", Expert Opin. Biol. Ther., 12:209-21 (2012).
Evans, et al., "A review of modern insulin analogue pharmacokinetic and pharmacodynamic profiles in type 2 diabetes: improvements and limitations", Diabetes Obes. Metab,. 13:677-84 (2011).
Gerich, "Insulin glargine: long-acting basal insulin analog for improved metabolic control", Curr. Med. Res. Opin. 20:31-7 (2004).
Gerich, "Novel insulins: expanding options in diabetes management", Am. J. Med., 113:308-316 (2002).
Hannon and Rossi, "Unlocking the potential of the human genome with RNA interference", Nature, 431 (7006):371-8 (2004).
Harris, et al., "Pegylation: a novel process for modifying pharmacokinetics" Clin Pharmacokinet., 40 (7):539-51 (2001).
Helms and Kelley, "Insulin glulisine: an evaluation of its pharmacodynamic properties and clinical application", Ann. Pharmacother., 43:658-68 (2009).
Hicke and Stephens, "Escort aptamers: a delivery service for diagnosis and therapy", J Clin Invest., 106 (8):923-8 (2000).
Hinds, et al., "Synthesis and Characterization of Poly(ethylene glycol)-Insulin Conjugates", Bioconjugate Chem., 11:195-201 (2000).
Hong, et al., "Alginate beads containing pH-sensitive liposomesand glucose oxidase: glucose-sensitive release", Colloid Polym. Sci., 287:1207-14 (2009b).
Hong, et al., "Analysis and optimization of copper-catalyzed azide-alkyne cycloaddition for bioconjugation", Angew. Chem., Int. Ed., 48:9879-83 (2009a).
Hong-Jensen, et al., "Reversible insulin self-assembly under carbohydrate control", J Am Chem Soc., 127(17):6158-9 (2005).
Hordern, "Insulin detemir: a review", Drugs Today, 42:505-17 (2006).
Huang ,et al., "Microdomain pH gradient and kinetics inside composite polymeric membranes of pH and glucose sensitivity", Pharm. Res., 25:1150-7 (2008).
Huynh, et al., "Functionalized injectable hydrogels for controlled insulin delivery", Biomaterials, 29:2527-34 (2008).
Ikeda and Taira, "Ligand-targeted delivery of therapeutic siRNA", Pharm Res., 23 (8): 1631-40 (2006).
Jeandidier, et al., "Current status and future prospects of parenteral insulin regimens, strategies and delivery systems for diabetes treatment", Adv. Drug Deliv. Rev., 35:179-98 (1999).
Jeong, et al., "siRNA conjugate delivery systems", Bioconjug Chem, 20 (1), 5-14 (2009).
Jonassen, et al., "Biochemical and physiological properties of a novel series of long-acting insulin analogs obtained by acylation with cholic acid derivatives", Pharm. Res., 23:49-55 (2006).
Kahn, "Banting Lecture. Insulin action, diabetogenes, and the cause of type II diabetes", Diabetes, 43:1066-84 (1994).
Kawamura, et al., "Synthesis of glucose-responsive bioconjugated gel particles using surfactant-free emulsion polymerization", Colloids Surf B Biointerfaces, 99:74-81 (2011).
Kim, et al., "Synthetic dsRNA Dicer substrates enhance RNAi potency and efficacy", Nat Biotechnol., 23 (2):222-6 (2005).
Kumareswaran, et al., "Artificial pancreas: an emerging approach to treat Type 1 diabetes", Expert Rev. Med. Devices, 6:401-10 (2009).
Lapeyre, et al., "Glucose-responsive mitrogels with a core-shell structure", Colloid Interface Sci., 327:316-23 (2008).
Lee, et al., "Synthesis and biological properties of insulin-deoxycholic acid chemical conjugates", Bioconjugate Chem., 16:615-20 (2005).
Leonard and Roy, "QSAR by LFER model of HIV protease inhibitor mannitol derivatives using FA-MLR, PCRA, and PLS techniques", Bioorg Med Chem., 14 (4):1039-46 (2006).
Lindgren, et al., "Cell-penetrating peptides", Trends Pharmacol Sci., 21 (3):99-103 (2000).
Lorenz, et al., "Steroid and lipid conjugates of siRNAs to enhance cellular uptake and gene silencing in liver cells", Bioorg Med Chem Lett., I4 (19):4975-7 (2004).
Love, et al., "Lipid-like materials for low-dose, in vivo gene silencing", PNAS, 107 (5):1864-9 (2010).
Lutz, "Copper-free azide-alkyne cycloadditions: new insights and perspectives", Angew. Chem., Int. Ed., 47:2182-4 (2008).
Mahon, et al., "Combinatorial approach to determine functional group effects on lipidoid-mediated siRNA delivery", Bioconjug Chem., 21 (8):1448-54 (2010).
Matsumoto, et al., "Glucose-responsive polymer gel bearing phenylborate derivative as a glucose-sensing moiety operating at the physiological pH", Biomacromolecules, 5:1038-45 (2004).
McManus, et al., "Gene silencing in mammals by small interfering RNAs", Nat Rev Genet, 3 (10), 737-47 (2002).
Moschos, et al., "Lung delivery studies using siRNA conjugated to TAT(48-60) and penetratin reveal peptide induced reduction in gene expression and induction of innate immunity", Bioconjug Chem,., 18 (5):1450-9 (2007).
Mukerjee and Pruthi, "Oral Insulin Delivery by Polymeric Nanospheres", Biomed. Nanotechnol., 3:68-74 (2007).
Muratovska and Eccles, "Conjugate for efficient delivery of short interfering RNA (siRNA) into mammalian cells", FEBS Lett., 558 (1-3):63-8 (2004).
Owens, et al., "Insulins today and beyond", Lancet, 358:739-46 (2001).
Owens, et al., "New horizons—alternative routes for insulin therapy", Nat. Rev. Drug Discov., 1:529-40 (2002).

(56) References Cited

OTHER PUBLICATIONS

Phillips, et al., "Supramolecular Protein Engineering: Design of Zinc-stapled Insulin Hexamers as a Long Acting Depot", J. Biol. Chem., 285:11755-9 (2010).
Pickup, et al., "Nanomedicine and its potential in diabetes research and practice", Diabetes Metab. Res. Rev., 24: 604-10 (2008).
Pooga, et al., "Cell penetration by transportan", FASEB J., 12 (I):67-77 (1998).
Prochiantz, Messenger proteins homeoproteins, TAT and others ,, J Soc Biol., 194(3-4):119-23 (2000).
Ravaine, et al., "Chemically controlled closed-loop insulin delivery", J. Control Release, 132:2-11 (2008).
Rozema, et al., "Dynamic PolyConjugates for targeted in vivo delivery of siRNA to hepatocytes", PNAS, 104 (32):12982-7 (2007).
Schroeder, et al., "Lipid-based nanotherapeutics for siRNA delivery", J Intern Med., 267 (I), 9-21 (2010).
Semple, et al., "Rational design of cationic lipids for siRNA delivery", Nat Biotechnol., 28 (2): 172-6 (2010).
Shechter, et al., "Albumin-insulin conjugate releasing insulin slowly under physiological conditions: a new concept for long-acting insulin", Bioconjugate Chem., 16: 913-20 (2005).
Shechter, et al., "Reversible pegylation of insulin facilitates its prolonged action in vivo", Eur. J. Pharm. Biopharm., 70:19-28 (2008).
Siddiqui, "Insulin analogues: new dimension of management of diabetes mellitus", Mymensingh Med J., 16:117-21 (2007).
Soutschek, et al., "Therapeutic silencing of an endogenous gene by systemic administration of modified siRNAs", Nature 432 (7014):173-8 (2004).
Springsteen and Wang, "A detailed examination of boronic acid-dial complexation", Tetrahedron, 58:5291-5300 (2002).
Stanton, et al., "Medicinal Chemistry of siRNA Delivery", J Med Chem., 53 (22):7887-901 (2010).
Stumvoll, et al., "Type 2 diabetes: principles of pathogenesis and therapy", Lancet, 365:1333-46 (2005).
Szypowska, et al.,"E., Long-acting insulin analogue detemir compared with NPH Insulin in type 1 diabetes. A systematic review and meta-analysis", Pol. Arch. Med. Wewn, 121:237-46 (2011).
Tang, et al., "A reversible hydrogel membrane for controlling the delivery of macromolecules", Biotechnol. Bioeng., 82:47-53 (2003).
Tripathi, et al., "Anti-HIV-I activity of anti-TAR polyamide nucleic acid conjugated with various membrane transducing peptides", Nucleic Acids Res., 33 (13):4345-56 (2005).
Turner, et al., "Cell-penetrating peptide conjugates of peptide nucleic acids (PNA) as inhibitors of HIV-1 Tat-dependent transactivation in cells", Nucleic Acids Res., 33 (21): 6837-49 (2005).
Turner, et al., "synthesis, cellular uptake and HIV-I Tat dependent trans-activation inhibition activity of oligonucleotide analogues disulphide-conjugated to cell-penetrating peptides", Nucleic Acids Res., 33 (I):27-42 (2005b).
Vaishnaw, et al., "A status report on RNAi therapeutics", Silence 1 (I):14 (2010).
Vives, et al., "A truncated HIV-I Tat protein basic domain rapidly translocates through the plasma membrane and accumulates in the cell nucleus", J Biol Chem.,272 (25):16010-7 (1997).
Wang, et al., "Boronic Acid-Based Sensors", Curr. Org. Chem., 6:1285-317 (2002).
Whitehead, et al. "Knocking down barriers: advances in siRNA delivery", Nat Rev Drug Discov., (2):129-38 (2009).
Wild, et al., "Global prevalence of diabetes: estimates for the year 2000 and projections for 2030", Diabetes Care, 27: 1047-1053 (2004).
Wolfrum, et al., "Mechanisms and optimization of in vivo delivery of lipophilic siRNAs", Nat Biotechnol., 25 (10), 1149-57 (2007).
Wu, et al., "Molecular targeting and treatment of an epidermal growth factor receptor-positive glioma using boronated cetuximab", Clin Cancer Res., 13 (4):1260-8 (2007).
Wu, et al., "Phenylboronic acid grafted chitosan as a glucose-sensitive vehicle for controlled insulin release", J. Pharm. Sci., 100:2278-86 (2011).
Xia, et al., "Intravenous siRNA of brain cancer with receptor targeting and avidin-biotin technology", Pharm Res., 24 (12):2309-16 (2007).
Xu, et al., "Investigation of Variation in Gene Expression Profiling of Human Blood by Extended Principle Component Analysis", PLoS One, 6 (10):e26905 (2011).
Yamada, et al., "Versatile site-specific conjugation of small molecules to siRNA using click chemistry", J Org Chem., 76 (5)1198-211 (2011).
Zhang, et al., "Intravenous RNA interference genetherapy targeting the human epidermal growth factor receptor prolongs survival in intracranial brain cancer", Clin Cancer Res., 10 (11):3667-77 (2004).
Zion, "Glucose-responsive materials for self-regulated insulin delivery", Ph. D. Thesis, Massachusetts Institute of Technology (2004).
International Search Report for PCT/US2013/074794 dated Jun. 14, 2014.

\* cited by examiner

General Form of PBAs used:

Where X is any of the following: -Fluro(F), -Nitro($NO_2$), -Cyano(CN), or H

Specific Examples of some PBAs used:

INSULIN DERIVATIVES FOR DIABETES TREATMENT

CROSS-REFERENCE TO RELATED APPLICATIONS

This application is a 371 application of International Application No. PCT/US2013/074794, filed Dec. 12, 2013, which claims benefit and priority to U.S. Provisional Application No. 61/736,079, filed Dec. 12, 2012, U.S. Provisional Application No. 61/736,092, filed Dec. 12, 2012, and U.S. Provisional Application No. 61/736,109, filed Dec. 12, 2012. International Application No. PCT US2013/074794, Filed Dec. 12, 2013, U.S. Provisional Application No. 61/736,079, filed Dec. 12, 2012, Application No. 61/736,092, filed Dec. 12, 2012, and Application No. 61/736,109, filed Dec. 12, 2012, are hereby incorporated by reference in their entirety.

FIELD OF THE INVENTION

This invention generally relates to smart or interactive delivery systems for therapeutics, prophylactic or diagnostic agents in response to glucose levels.

BACKGROUND OF THE INVENTION

Diabetes mellitus is a disorder of glucose regulation with accumulation of glucose in the blood. In normal individuals, insulin is secreted basally, usually in the range of 0.5 to 1.0 units per hour, and the levels are increased after a meal. Responsive to the rise in blood glucose levels following a meal, the pancreas secretes a bolus of insulin, which returns blood glucose to normal levels by stimulating the uptake of glucose into cells and signaling the liver to reduce glucose production. There are normally two phases of insulin release in response to a meal. The early phase (responsible for shutting down hepatic glucose production) is a spike of insulin release that occurs within 2-15 minutes of eating. The late phase release extends about 2 hours. Between meals the liver breaks down glycogen stores to provide glucose to the brain and other tissues.

Diabetes results in chronic hyperglycemia due to the inability or reduced ability of the pancreas to produce adequate amounts of insulin or due to the inability or reduced ability of cells to synthesize and/or release insulin. In diabetics, the effectiveness of the first-phase response is decreased or absent, leading to elevated postprandial glucose levels. Diabetes is a major public health problem affecting 285 million people across the world and this number is expected to be over 450 million by 2030 (Wild, et al., *Diabetes Care,* 27: 1047-1053 (2004). The malfunction of glucose regulation arises from (1) insufficient secretion of insulin due to autoimmune-mediated destruction of pancreatic f3-cells (type 1 diabetes) or (2) disorders of both insulin resistance and secretion (type 2 diabetes) (Pickup, et al., *Diabetes Metab. Res. Rev.,* 24: 604-610 (2008); Stumvoll, et al. *Lancet,* 365:1333-1346 (2005); and Kahn, *Diabetes* 43:1066-1084 (1994).

Frequent subcutaneous insulin injections and regular monitoring of blood glucose levels are essential for treatment of type 1 diabetic patients and some type 2 diabetic patients (Owens, et al., *Lancet,* 358:739-746 (2001)). However, such self-administration is painful and requires an indispensable commitment of patients. More importantly, this treatment, known as open-loop insulin delivery, does not maintain normoglycemia due to highly dynamic blood glucose concentrations (Jeandidier, et al., *Adv. Drug Deliv. Rev.,* 35:179-198 (1999); Owens, et al., *Nat. Rev. Drug Discov.,* 1:529-540 (2002)). Lack of tight control over glucose concentrations closer to the normal level accounts for many chronic complications such as limb amputation, blindness and kidney failure and can result in fatal hypoglycemia (*N Engl J Med.,* 329:977-986 (1993)). Therefore, a pancreas-like, synthetic closed-loop device able to continuously and intelligently release insulin in response to blood glucose levels is highly desirable (Kumareswaran, et al. *Expert Rev. Med. Devices,* 6:401-410 (2009); Ravaine, et al., *J. Control Release,* 132:2-11 (2008)).

A straightforward strategy to achieve continuous release in response to glucose levels is to integrate a glucose monitoring moiety and a sensor-triggered insulin releasing moiety into one system. To date, a number of glucose-responsive formulations and devices have been explored, mainly derived from three categories: (1) glucose oxidase (GOx) based enzymatic reaction-induced response systems; (2) binding lectin protein Concanavalin A (Con A) based response systems, and (3) phenylboronic acid (PBA) based synthetic glucose-binding systems (Ravaine, et al., *J. Control Release* 132:2-11 (2008)).

Efforts to prepare insulin with patient-specific kinetics have explored a number of different modification strategies to create variants with more rapid activity as well as those with prolonged activity, and combinations of various types may be useful for improved glycemic control. For comparison, native insulin, which forms hexamers when formulated with zinc, has an onset time of 30-60 minutes, a peak window of action from 2-3 hours, and a duration of action of 8-10 hours. Fast acting formulations have been developed, such as Insulin Lispro where the B29 lysine residue and the B28 proline residue have been switched, in order to prevent hexamer formation and improve uptake. Lispro has a reduced onset time of just 5-15 minutes, with its a peak action at 30-90 minutes and a duration of action of 4-6 hours. Long acting formulations, such as Insulin Detemir where a saturated fourteen-carbon alkyl segment is covalently attached to the amine side-chain of lysine B29, have been developed to prolong insulin duration by enabling it to bind to and be sequestered by circulating serum albumin. As a result, Insulin Detemir has an onset of action at 1-2 hours, with peak action at 6-8 hours and duration lasting up to 24 hours. Long acting insulin, in particular, is useful as a daily injection to supplement basal insulin levels and prevent spikes in blood glucose levels throughout the day.

PBA is boronic acid containing a phenyl substituent and two hydroxyl groups attached to boron. PBA and its derivatives form complexes with polyol molecules such as glucose and fructose, and can form complexes with polyols and diols. The ability of PBA to bind polyols and diols has been exploited in different ways to provide a glucose binding insulin delivery system. Some researchers have directly coupled a PBA moiety to insulin, to provide glucose binding insulin. For example, U.S. Publication No. 20030186846 by Hoeg-Johnson, et al., discloses an insulin delivery system made of insulin derivatives with a built in glucose sensor, such as an aryl boronate moiety.

These glucose insulin delivery systems have several limitations. For PBA systems, the challenge remains to design devices that function in response to glucose under physiological conditions.

It is therefore an object of this invention to provide a non-toxic, interactive or "smart" insulin delivery system that is responsive to changing glucose concentrations.

It is a further object of the present invention to provide a method of controlling blood glucose levels in a patient in need thereof, by administering a smart insulin delivery system which responds to changing glucose concentrations.

SUMMARY OF THE INVENTION

Compounds, compositions, and methods for "smart" delivery of a therapeutic, prophylactic or diagnostic agent, such as glucose-mediated delivery of insulin through glucose-sensing insulin derivatives, are provided. The insulin derivatives bind serum albumin or agglomerate in vivo. The insulin derivatives effectively dissociate to release insulin under hyperglycemic conditions, where the complexation of glucose to a glucose-sensing element alters properties of the insulin derivative leading to the dissociation. The compounds, compositions, and methods provide a delivery strategy for both self-regulated and long-term diabetes management. Other therapeutic, prophylactic, or diagnostic agents can be included or substituted for delivery. For example, derivatives of glucagon, GLP-1, or a GLP-1 agonist can be used.

In some embodiments, the insulin derivative contains insulin or an insulin analog covalently linked a component containing a glucose binding component. In some embodiments, the component containing the glucose binding component includes a hydrophobic group. For example, the derivatized insulin can include one or more phenylboronic acid (PBA) groups, a hydrophobic group, and insulin or an insulin analog. The hydrophobic group can be covalently linked to the insulin or insulin analog and the PBA groups can be covalently linked to the hydrophobic group, the insulin or insulin analog, or both. In some embodiments, the insulin or insulin analog can form insulin hexamers and the derivatized insulin can bind to serum albumin in inverse proportion to glucose levels. For example, the insulin derivative can bind to serum albumin when glucose levels are low or normal and can be released from binding when glucose levels are high.

In some embodiments, the insulin derivative has the formula $X_1$-$X_2$, where $X_1$ is insulin or an insulin analog and $X_2$ is a component containing a glucose binding component.

In some embodiments, the insulin or insulin analog is derivatized with a lipid. The lipid is derivatized with a PBA group. For example, in the formula above $X_2$ can be —CO-alkylene-$R_9$ or —CO-alkenyl-$R_9$, where $R_9$ is a phenylboronic acid. The alkylene or alkenyl group can be substituted or unsubstituted. The number of carbons in the alkylene or alkenyl group can vary. In some embodiments, the number of carbons is from about 3 to about 25. In some embodiments, the number of carbons is 11.

In some embodiments, the insulin or insulin analog is derivatized with a bile acid. The bile acid is derivatized with one or more PBA groups. For example, in the formula above $X_2$ can be —CO—$R_{13}$, where $R_{13}$ is a bile acid and one or more hydroxyls on the bile acid are derivatized with a phenylboronic acid group. In some embodiments, the bile acid is cholic acid, lithocholic acid, hyocholic acid, deoxycholic acid, hyodeoxycholic acid, or chenodeoxycholic acid.

In some embodiments, the insulin or insulin analog is derivatized with a pseudolysine-containing group. The pseudolysine-containing group is derivatized with a PBA group. For example, in the formula above $X_2$ can be —CO—$(CH_2)_r$—NH—CO—$CHR_{14}$—NH—CO—$(CH_2)_s$, where r is an integer from 3-25, s is an integer from 3-25, and $R_{14}$ is an amine-containing group comprising a phenylboronic acid group. In some embodiments, r is 3, 5, or 11 and s is 6, 8, 10, 12, or 14. In some embodiments, r and s together total to an integer from 13 to 21.

In some embodiments, the insulin or insulin analog is derivatized with a linker with a functional group. The linker is derivatized with a PBA group. The functional group is selected from a variety of functional groups such that agglomeration of the insulin is glucose-responsive. For example, in the formula above $X_2$ can be —CO—$(CH_2)_j$—NH—CO—$CR_1R_2$, where j is an integer from 3-25, where $R_1$ is —NH—$R_{12}$ or —NH—CO—$CH_2$—$CH_2$—$CNR_{12}$—$R_{32}$, where $R_{32}$ is glucamine, gluconic acid, glucosamine, fructosamine, galactosamine, mannosamine, or other hexosamines; $R_{12}$ is selected from the group consisting of hydrogen, —$SO_2$alkyl, —$SO_2$cycloalkyl, —$SO_2$heterocycloalkyl, —$SO_2$aryl, —$SO_2$heteroaryl, —COalkyl, —COcycloalkyl, —COheterocycloalkyl, —COaryl, —COheteroaryl, —CONHalkyl, —CONHcycloalkyl, —CONHheterocycloalkyl, —CONHaryl, —CONHheteroaryl, where alkyl, cycloalkyl, heterocycloalkyl, aryl, and heteroaryl groups are substituted or unsubstituted; $R_2$ is —$(CH_2)_n$—$R_{11}$, where n is an integer from 3-25; and $R_{11}$ is a phenylboronic acid group. In some embodiments, n is 4. In some embodiments, $R_{12}$ is a sulfonyl chloride, isocyanate, carboxylic acid chloride, aldehyde, or hydrogen.

In some embodiments, the insulin or insulin analog is derivatized with an oligomer of monomer residues having modified side chains. At least one of the side chains is modified with a PBA group. For example, in the formula above $X_2$ can be an oligomer of 2 to 5 monomer residues, where the monomers comprise single modified side chains, dual modified side chains, or combinations thereof. The side chains are modified with a phenylboronic acid group, hydrophobic residues, hydrophilic residues, charged residues, diol residues, fluorescent residues, and combinations thereof, where at least one of the side chains is modified with phenylboronic acid.

In some embodiments, each monomer residue of the oligomer is —CO—O—$R_3$—, where $R_3$ is —$CR_4$—$(CH_2)_m$—NH— or pyrrolidine substituted with $R_4$, where m is an integer from 0-25, $R_4$ is —CO—NH—$R_5$ or —CO—NH—C(CH—CO—NH—$R_5$)$_2$, and $R_5$ is the side chain modification. In some embodiments, $R_5$ is a phenylboronic acid group, $C_{8-18}$ alkyl, —$CH_2$-phenyl, —$(CH_2$—$CH_2$—O$)_p$—H or —$(CH_2$—$CH_2$—O$)_p$—$CH_3$, wherein p is an integer from 1-500, —$CH_2$-dioxane, —$CH_2$—$CH_2$-oxazane, —$CH_2$—$CH_2$—N$(CH_2$—$CH_3)_2$, —$CH_2$—$CH_2$-pyrazole, a fluorescent group, -piperidine-phenyl, -piperidine-oxazane, -piperidine-$CH_2$—$CH_2$—N$(CH_2$—$CH_3)_2$, -piperidine-$CH_2$—$CH_2$-pyrazole, -dimethylaminobenzyl, or -pyridine. At least one $R_5$ is a phenylboronic acid group.

In some embodiments, the insulin or insulin analog is derivatized with a diol-containing group. The diol-containing group is complexed with a PBA group. For example, in the formula above $X_2$ can be —CO—$R_6$-$R_7$, where $R_6$ is a linker or is not present and $R_7$ is a diol-containing group complexed to a hydrophobic phenylboronic acid (PBA) group. The diol-containing group includes one or more diols. The hydrophobic PBA group includes one or more PBA groups covalently linked to a hydrophobic group. At least on diol and one hydrophobic PBA group form a boronic ester.

In some embodiments, the diol-containing group is -(DOPA-Gly)$_i$—$NH_2$, wherein i is an integer from 1-5. In some embodiments, the diol-containing group is 6-methyl-6-deoxy-D-galactose, 1-deoxy-β-D-lactopyranoside, α-D-Mannopyranosyl, or adenosine. In some embodiments, $R_6$ is —CO—(CH$_2$)$_h$—R$_{31}$—, where h is an integer from 3-25 and R$_{31}$ is O-triazole- or CO—NH—CH$_2$—CO-dibenzo-cyclocta-triazole-. In some embodiments, the hydrophobic group is —(CH2)$_k$—CH$_3$, where k is an integer from 3-25. In some embodiments, the hydrophobic group is a bile acid. In some embodiments, k is 11.

The glucose binding component is a chemical group capable of binding to or reacting with glucose. Examples of reversible glucose sensors include organic borates, such aryl boronates or other borates. In preferred embodiments, the glucose binding component is a PBA group. In some embodiments, the PBA grow is:

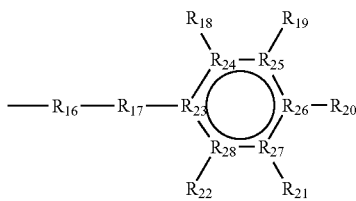

where R$_{16}$ is NH, NR$_{29}$, or is not present; R$_{17}$ is CH$_2$, CO, SO$_2$, or is not present; R$_{18}$, R$_{19}$, R$_{20}$, R$_{21}$, and R$_{22}$ are each independently —B(OH)$_2$, —F, —NO$_2$, —CN, —H, or not present, where one and only one of R$_{18}$, R$_{19}$, R$_{20}$, R$_{21}$, and R$_{22}$ is —B(OH)$_2$; R$_{23}$, R$_{24}$, R$_{25}$, R$_{26}$, and R$_{27}$ are each independently C or N, where at most only three of R$_{23}$, R$_{24}$, R$_{25}$, R$_{26}$, and R$_{27}$ are N; and R$_{29}$ is C$_{1-4}$ alkyl.

Also provided are methods of making derivatized insulin. In some embodiments, the derivatized insulin is made by (i) reacting a N-hydroxysuccinimide (NHS)-activated alkyne linker with insulin or an insulin analog to form an alkyne-derivatized insulin, (ii) reacting a diol-containing compound comprising azide with the alkyne-derivatized insulin to form diol-derivatized insulin, and (iii) reacting a hydrophobic phenylboronic acid (PBA) group with the diol-derivatized insulin to form the derivatized insulin.

In some embodiments, the derivatized insulin is made by:
(i) (a) reacting NH$_2$—(CH$_2$)$_q$—CO—O—CH$_3$ with a carboxyphenylboronic acid group to form R$_9$—(CH$_2$)$_q$—CO—O—CH$_3$, where q is an integer from 3-25 and R$_9$ is a phenylboronic acid group, or
(b) reacting NH$_2$—(CH$_2$)$_q$—CO—O—CH$_3$ with a bromo-chlorosulfonyl benzene group to form R$_{15}$—SO$_2$—NH—(CH$_2$)$_q$—CO—O—CH$_3$, and reacting the R$_{15}$—SO$_2$—NH—(CH$_2$)$_q$—CO—O—CH$_3$ with a diboron ester to form R$_9$—(CH$_2$)$_q$—CO—O—CH$_3$, where q is an integer from 3-25, R$_{15}$ is a bromobenzene group, and R$_9$ is a phenylboronic acid group;
(ii) reacting the R$_9$—(CH$_2$)$_q$—CO—O—CH$_3$ to form R$_9$—(CH$_2$)$_q$—COOH, and
(iii) reacting the R$_9$—(CH$_2$)$_q$—COOH with insulin or an insulin analog to form the derivatized insulin.

Also provided are derivatized insulins made by the methods provided herein.

Also provided are methods of alleviating one or more symptoms of diabetes by administering to a diabetic subject an effective amount of a derivatized insulin as provided herein.

Also provided are methods of making a derivatized insulin. In some embodiments, the method of making derivatized insulin includes screening of different derivatized insulins to identify derivatized insulins useful for treating diabetes. For example, an agglomerate of a plurality of the derivatized insulin molecules can be tested for glucose-responsive release of the derivatized insulin from the agglomerate. Glucose-responsive release of the derivatized insulin from the agglomerate identifies the derivatized insulin as useful for treating diabetes. Also provided are derivatized insulins made by the method.

DETAILED DESCRIPTION OF THE INVENTION

I. Definitions

Figure 1A:
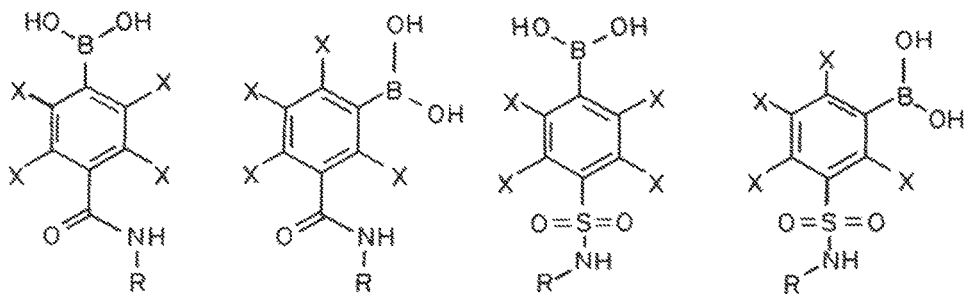
FIG. 1A is a diagram of the generic structures of PBAs used for glucose sensing (top row) with various electron-withdrawing groups (X=-Fluoro, -Nitro, —Cyano, or H) at various positions in the ring. Additionally, specific structural examples (bottom row) showing the most common form of PBAs used in these studies.

"Controlling blood glucose levels" refers to the maintenance of blood glucose concentrations at a desired level, typically between 70-130 mg/dL or 90-110 mg/dL.

"Dosage unit form" as used herein refers to a physically discrete unit of conjugate appropriate for the patient to be treated.

"Hydrophilic," as used herein, refers to molecules which have a greater affinity for, and thus solubility in, water as compared to organic solvents. The hydrophilicity of a compound can be quantified by measuring its partition coefficient between water (or a buffered aqueous solution) and a water-immiscible organic solvent, such as octanol, ethyl acetate, methylene chloride, or methyl tert-butyl ether. If after equilibration a greater concentration of the compound is present in the water than in the organic solvent, then the compound is considered hydrophilic.

"Hydrophobic," as used herein, refers to molecules which have a greater affinity for, and thus solubility in, organic solvents as compared to water. The hydrophobicity of a compound can be quantified by measuring its partition coefficient between water (or a buffered aqueous solution) and a water-immiscible organic solvent, such as octanol, ethyl acetate, methylene chloride, or methyl tert-butyl ether. If after equilibration a greater concentration of the compound is present in the organic solvent than in the water, then the compound is considered hydrophobic.

"Peptide," as used herein includes "polypeptide," "oligopeptide," and refers to a chain of at α-amino acid residues linked together by covalent bonds (e.g., peptide bonds). The length of the peptide is limited at the lower end only by the minimum number amino acids required to form a self-assembling peptide.

"Pharmaceutically acceptable carrier" as used herein means a non-toxic, inert solid, semi-solid or liquid filler, diluent, encapsulating material or excipient. Remington's Pharmaceutical Sciences Ed. by Gennaro, Mack Publishing, Easton, Pa., current edition, discloses various carriers used in formulating pharmaceutical compositions and known techniques for the preparation thereof.

The term "oligomeric", as used herein, describes something made primarily from a plurality of monomeric units and is generally referred to as an "oligomer." An oligomer can have a molecular weight between 10 Daltons and 15,000 Daltons, between 100 Daltons and 10,000 Daltons, or between 500 Daltons and 5,000 Daltons. An oligomer can have from 3 to 100 monomeric units, from 4 to 50 monomeric units, or from 5 to 25 monomeric units.

"Biocompatible" and "biologically compatible," as used herein, generally refer to materials that are, along with any metabolites or degradation products thereof, generally non-toxic to the recipient, and do not cause any significant adverse effects to the recipient. Generally speaking, biocompatible materials are materials which do not elicit a significant inflammatory, immune or toxic response when administered to an individual.

The terms "smart delivery system" or "interactive delivery system", as used interchangeably herein, refer to a delivery system for one or more therapeutic, prophylactic, or diagnostic agents wherein the rate of delivery is responsive to one or more stimuli indicative of the need for delivery. As a non-limiting example, a smart insulin delivery system delivers insulin at a rate that is dependent upon the glucose levels in proximity to the delivery system.

The total response, i.e. the total amount of insulin released or made biologically available will depend upon the total time the glucose level is high enough to promote dissociation, i.e., the amount of time it takes to restore normoglycemia. The response is preferably pulsatile, and preferably little to no insulin is released at hypo- or normoglycemia. The insulin derivatives described herein should have a lower rate of dissociation at normoglycemia than at hyperglycemia.

The term "pulsatile" or "pulsatile release," as used herein, refers to the release of multiple doses from a single administration to a subject. The individual doses can be administered at a variety of intervals, depending on the formulation of the delivery system and the application. A smart pulsatile delivery system is capable of administering multiple doses of a therapeutic, prophylactic, or diagnostic agent in response to one or more stimuli, preferably wherein the dosage delivered is responsive to the deviation of the stimuli from a target value. As a non-limiting example, a smart pulsatile insulin delivery system preferably delivers little to no insulin during periods of normoglycemia but delivers a dosage of insulin in response to hypoglycemic conditions that is responsive to the deviation from normoglycemia, preferably in an amount sufficient to restore normglycemic glucose levels.

For the insulin derivatives, the amount of insulin derivative released depends upon the glucose level and the time to locally restore normglycemia; more generally, the amount released should depend upon the deviation of the external stimulus from the normal value and the time needed to return to the normal value.

The expression "an amino acid residue having a carboxylic acid group in the side chain" designates amino acid residues like Asp, Glu and hGlu. The amino acids can be in either the L- or D-configuration. If nothing is specified it is understood that the amino acid residue is in the L configuration.

The expression "an amino acid residue having a neutral side chain" designates amino acid residues like Gly, Ala, Val, Leu, Ile, Phe, Pro, Ser, Thr, Cys, Met, Tyr, Asn and Gln.

By "activated acid" is meant a carboxylic acid in which an activated leaving group has been attached to the acyl carbon enabling reaction with an amino group under formation of an amide bond and release of the leaving group. Activated fatty acids may be activated esters of fatty acids, activated amides of fatty acids and anhydrides or chlorides. Activated fatty acid includes derivatives thereof such as N-hydroxybenzotriazole and N-hydroxysuccinimide.

By "fatty acid" is meant a linear or branched carboxylic acids having at least 2 carbon atoms and being saturated or unsaturated. Examples of fatty acids are capric acid, lauric acid, tetradecanoic acid (myristic acid), pentadecanoic acid, palmitic acid, heptadecanoic acid, and stearic acid.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. Likewise, preferred cycloalkyls have from 3-10 carbon atoms in their ring structure, and more preferably have 5, 6 or 7 carbons in the ring structure. The ranges provided above are inclusive of all values between the minimum value and the maximum value.

The term "alkyl" includes both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

The alkyl groups may also contain one or more heteroatoms within the carbon backbone. Preferably the heteroatoms incorporated into the carbon backbone are oxygen, nitrogen, sulfur, and combinations thereof. In certain embodiments, the alkyl group contains between one and four heteroatoms.

"Alkenyl" and "Alkynyl", as used herein, refer to unsaturated aliphatic groups containing one or more double or triple bonds analogous in length (e.g., $C_2$-$C_{30}$ and the preferred ranges discussed above) and possible substitution to the alkyl groups described above.

"Aryl", as used herein, refers to 5-, 6- and 7-membered aromatic ring. The ring may be a carbocyclic, heterocyclic, fused carbocyclic, fused heterocyclic, bicarbocyclic, or biheterocyclic ring system, optionally substituted by halogens, alkyl-, alkenyl-, and alkynyl-groups. Broadly defined, "Ar", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl", "aryl heterocycles", or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —$CN$, or the like. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro [2,3b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_{1-4}$) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms consisting of carbon and 1, 2, 3, or 4 heteroatoms each selected from the group consisting of non-peroxide oxygen, sulfur, and N(Y) where Y is absent or is H, O, ($C_1$-$C_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

"Halogen", as used herein, refers to fluorine, chlorine, bromine, or iodine.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

When a compound is stated to be "soluble at physiological pH values" it means that the compound can be used for preparing compositions that are fully dissolved at physiological pH values. Such favorable solubility may either be due to the inherent properties of the compound alone or a result of a favorable interaction between the compound and one or more ingredients contained in the vehicle.

II. Compositions

A. Glucose Binding Component

The insulin derivative includes a chemical group capable of binding to or reacting with glucose. Examples of reversible glucose sensors are organic borates, preferably aryl boronates or other borates. Boronic acids covalently react with cis-diols to form five or six membered cyclic esters in an alkaline aqueous solution, which dissociates in acidic pH.

Boronate sensors that bind glucose under physiological conditions are preferred. Examples of useful boronates include, but are not limited to, aryl boronates, aminomethyl-aryl-2-boronates, and other boronates with amino groups in the vicinity or aryl boronates substituted with electron-withdrawing groups for example, sulfo-, carboxy-, nitro-, cyano-, fluoro-phenyl boronates, pyridine boronates, pyridinium boronates or their combinations. Diboronates may be employed to provide glucose selectivity over for instance fructose and lactate.

In a preferred embodiment, the hydrophilic domain of the self-assembling peptide is terminated with phenylboronic acid (PBA) group. A PBA group is a compound, residue or moiety comprising a benzene with a boronic acid functional group. The ring can be further substituted or not further substituted (beyond the boronic acid functional group and the covalent linkage to backbone structure) and can be amino heterocyclic. For example, a PBA group can have the structure:

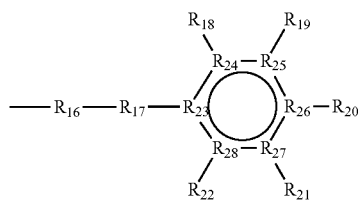

where $R_{16}$ is NH, $NR_{29}$, or is not present; $R_{17}$ is $CH_2$, CO, $SO_2$, or is not present; $R_{18}$, $R_{19}$, $R_{20}$, $R_{21}$, and $R_{22}$ are each independently —B(OH)$_2$, —F, —NO$_2$, —CN, —H, or not present, where one and only one of $R_{18}$, $R_{19}$, $R_{20}$, $R_{21}$, and $R_{22}$ is —B(OH)$_2$; $R_{23}$, $R_{24}$, $R_{25}$, $R_{26}$, and $R_{27}$ are each independently C or N, where at most only three of $R_{23}$, $R_{24}$, $R_{25}$, $R_{26}$, and $R_{27}$ are N; and $R_{29}$ is $C_{1-4}$ alkyl.

The PBA structure can be designed to bind glucose at a physiological value. The pKa of traditional phenylboronic acid is approximately 8.9. However, the PBA conjugate is chemically modified to lower the pK to less than 8.9 (Matsumoto A. et al., *Chem. Commun.*, 2010, 46, 2203-2205). Based on this value, only a limited percentage of PBA should be able to covalently bind glucose at physiological pH. However, there is sufficient glucose interaction to affect agglomeration of the compositions.

Figure 1A:
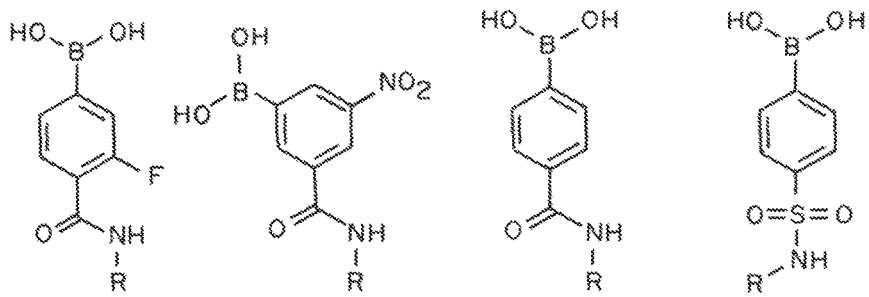
Figure 1B:
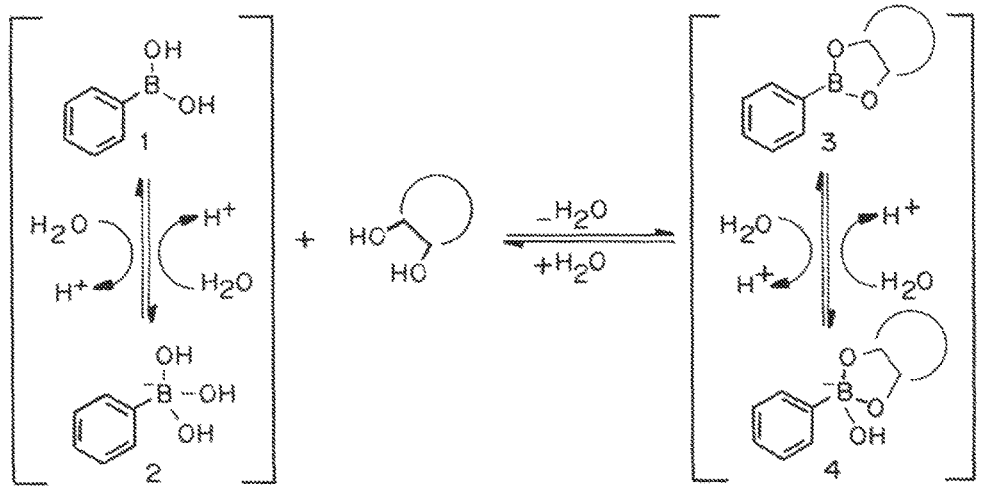
FIG. 1B is a diagram showing the binding equilibrium of phenylboronic acid with a diol.

The phenylboronic acid moieties are in equilibrium between the charged (anionic) and uncharged form as shown in FIG. 1B. Only charged phenylboronic acid moieties can form a stable complex with glucose. The complex between the uncharged form and glucose is unstable because of its high susceptibility to hydrolysis. When the charged phenylboronic acid moieties form complexes with glucose, the equilibrium is shifted in the direction of increasing charged phenylboronic acid groups. The increasing negative charge on the PBA groups results in disruption of the secondary structure causing the compositions to dissociate and make therapeutic biologically available. Therefore, the rate of such therapeutic release adapts to glucose level fluctuations.

The amount of negatively charged PBA is increased with the increase of the glucose level, which results in the dissociation of the compositions and subsequent increase of the rate of the therapeutic release.

B. Therapeutic, Prophylactic or Diagnostic Agents

The compositions described herein can be used for the responsive and/or controlled delivery of one or more therapeutic, prophylactic, or diagnostic agents. In some embodiments the compositions contain only a single therapeutic, prophylactic, or diagnostic agent, i.e. insulin. In other embodiments multiple agents can be delivered either in a responsive manner or in a controlled manner, either together or independently. For example, in some embodiments it can be advantageous to provide sustained extended release of a first therapeutic, prophylactic, or diagnostic agent, while at the same time providing for release of a second therapeutic, prophylactic, or diagnostic agent that is responsive to a particular stimulus. Examples of therapeutic, prophylactic, or diagnostic agents include insulin, insulin analogs, glucagon, GLP-1, or a GLP-1 agonist can be used. Combinations of derivatives of different therapeutic, prophylactic, or diagnostic agents can be used together in compositions for treating subjects.

1. Insulin

In preferred embodiments compositions are provided containing insulin or an insulin analog. "Insulin" refers to a natural peptide hormone made by the pancreas that controls the level of the sugar glucose in the blood. Insulin permits cells to use glucose. Human insulin has three primary amino groups: the N-terminal group of the A-chain and of the B-chain and the ε-amino group of LysB29. Any of these primary amines, or a primary amine added in an insulin analog, can be used to as the attachment point of derivatizing molecules and groups.

"Insulin analog" as used herein refers to human insulin in which one or more amino acid residues have been replaced by another amino acid residue or deleted or in which the A chain and/or the B chain has been extended by addition of one or more amino acid residues at the N-terminal or at the C-terminal and which controls the level of glucose in the blood but with different pharmacokinetics than the naturally occurring insulin. Examples of insulin analogs include NPH insulin; also known as Humulin N, Novolin N, Novolin NPH, NPH Iletin II, and isophane insulin, marketed by Eli Lilly and Company under the name Humulin N, is an intermediate-acting insulin given to help manage the blood sugar level of those with diabetes. Many people reported problems following being switched to these insulins in the 80s, from porcine/bovine insulins. Problems included mood/character changes, memory problems, and hypo-unawareness. By "insulin derivative" as used herein is meant a naturally occurring insulin or an insulin analogue which has been chemically modified, e.g., by introducing a side chain in one or more positions of the insulin backbone or by oxidizing or reducing groups of the amino acid residues in the insulin or by acylating a free amino group or a hydroxy group.

By "desB30" or "B(1-29)" is meant a natural insulin B chain or an insulin analog thereof lacking the B30 amino acid residue and by "A(1-21)" is meant the natural insulin A chain or an analog thereof. DesB30,desB29 human insulin is a human insulin lacking B29 and B30.

By "B1," "A1," etc. is meant the amino acid residue in position 1 in the B chain of insulin (counted from the N-terminal end) and the amino acid residue in position 1 in the A chain of insulin (counted from the N-terminal end), respectively. The amino acid residue in a specific position can also be denoted as, e.g., $Phe^{B1}$, which means that the amino acid residue in position B1 is a phenylalanine residue.

The insulin analogs can be such that position 28 of the B chain can be modified from the natural Pro residue to Asp, Lys, or Ile. Lys in position B29 can also be modified to Pro. Furthermore B30 can be Lys in which case B29 is different from Cys, Met, Arg and Lys.

Also, Asn at position A21 can be modified to Ala, Gln, Glu, Gly, His, Ile, Leu, Met, Ser, Thr, Trp, Tyr or Val, in particular to Gly, Ala, Ser, or Thr and in particular to Gly. Furthermore, Asn at position B3 can be modified to Lys or Asp. Further examples of insulin analogs are des(B30) human insulin, insulin analogs where one or both of B1 and B2 have been deleted; insulin analogs where the A-chain and/or the B-chain have an N-terminal extension and insulin analogs where the A-chain and/or the B-chain have a C-terminal extension. Further insulin analogs are such that one or more of B26-B30 have been deleted.

Lispro.

Eli Lilly and Company had the first insulin analog with "lispro" as a rapid acting insulin analog. It is marketed under the trade name Humalog. It was engineered through recombinant DNA technology so that the penultimate lysine and proline residues on the C-terminal end of the B-chain were reversed. This modification did not alter the insulin receptor binding, but blocked the formation of insulin dimers and hexamers. This allowed larger amounts of active monomeric insulin to be available for postprandial (after meal) injections.

Aspart.

Novo Nordisk created "aspart" and marketed it as Novo-Log/NovoRapid (UK-CAN) as a rapid acting insulin analog. It was created through recombinant DNA technology so that the amino acid, B28, which is normally proline, is substituted with an aspartic acid residue. The sequence was inserted into the yeast genome, and the yeast expressed the insulin analog, which was then harvested from a bioreactor. This analogue also prevents the formation of hexamers, to create a faster acting insulin. It is approved for use in CSII pumps and Flexpen, Novopen delivery devices for subcutaneous injection.

Glulisine.

Glulisine is a newer rapid acting insulin analog from Sanofi-Aventis, approved for use with a regular syringe, in an insulin pump or the Opticlik Pen. Standard syringe delivery is also an option. It is sold under the name Apidra. The FDA-approved label states that it differs from regular human insulin by its rapid onset and shorter duration of action.

Shifted Isoelectric Point Insulins.

Normal unmodified insulin is soluble at physiological pH. Analogues have been created that have a shifted isoelectric point so that they exist in a solubility equilibrium in which most precipitates out but slowly dissolves in the bloodstream and is eventually excreted by the kidneys. These insulin analogs and derivatives are used to replace the basal level of insulin, and may be effective over a period of up to 24 hours. However, some insulin derivatives, such as insulin detemir, bind to albumin rather than fat like earlier insulin varieties, and results from long-term usage (e.g. more than 10 years) have never been released.

Glargine Insulin.

Sanofi-Aventis developed glargine as a longer lasting insulin analog, and markets it under the trade name Lantus. It was created by modifying three amino acids. Two positively charged arginine molecules were added to the C-terminus of the B-chain, and they shift the isoelectric point from 5.4 to 6.7, making glargine more soluble at a slightly acidic pH and less soluble at a physiological pH. Replacing the acid-sensitive asparagine at position 21 in the A-chain by glycine is needed to avoid deamination and dimerization of the arginine residue. These three structural changes and formulation with zinc result in a prolonged action when compared with biosynthetic human insulin. When the pH 4.0 solution is injected, most of the material precipitates and is not bioavailable. A small amount is immediately available for use, and the remainder is sequestered in subcutaneous tissue. As the glargine is used, small amounts of the precipitated material will move into solution in the bloodstream, and the basal level of insulin will be maintained up to 24 hours. The onset of action of subcutaneous insulin glargine is somewhat slower than NPH human insulin. It is clear solution as there is no zinc in formula.

Detemir Insulin.

Novo Nordisk created insulin detemir and markets it under the trade name Levemir as a long-lasting insulin derivative for maintaining the basal level of insulin. The basal level of insulin may be maintained for up to 20 hours, but the time is clearly affected by the size of the injected dose. This insulin has a high affinity for serum albumin, increasing its duration of action.

2. Diabetes Medications

Exemplary diabetes medications include sulfonylureas, meglitinides, biguanides, thiazolidinediones, alpha-glucosidase inhibitors, or DPP-4 inhibitors. Sulfonylureas stimulate the beta cells of the pancreas to release more insulin. Chlorpropamide (Diabinese) is the only first-generation sulfonylurea still in use today. The second generation sulfonylureas are used in smaller doses than the first-generation drugs. There are three second-generation drugs: glipizide (Glucotrol and Glucotrol XL), glyburide (Micronase, Glynase, and Diabeta), and glimepiride (Amaryl). Meglitinides are drugs that also stimulate the beta cells to release insulin. Repaglinide (Prandin) and nateglinide (Starlix) are meglitinides. Metformin (Glucophage) is a biguanide. Biguanides lower blood glucose levels primarily by decreasing the amount of glucose produced by the liver. Rosiglitazone (Avandia) and pioglitazone (ACTOS) are in a group of drugs called thiazolidinediones. These drugs help insulin work better in the muscle and fat and also reduce glucose production in the liver. DPP-4 inhibitors help improve A1C without causing hypoglycemia. They work by preventing the breakdown of a naturally occurring compound in the body, GLP-1. GLP-1 reduces blood glucose levels in the body, but is broken down very quickly so it does not work well when injected as a drug itself. By interfering in the process that breaks down GLP-1, DPP-4 inhibitors allow it to remain active in the body longer, lowering blood glucose levels only when they are elevated. Sitagliptin (JANUVIA) and saxagliptin (ONGLYZA) are the two DPP-4 inhibitors currently on the market.

In some embodiments compositions are provided containing an insulin derivative and one or more additional diabetes medications that can be delivered together in a responsive manner, or independently by providing extended release of the diabetes medication in combination with responsive release of the insulin derivative in response to increased glucose levels.

In addition to insulin and insulin analogs, other therapeutic, prophylactic or diagnostic agents can be encapsulated to treat or manage diseases or disorders. These can include small drugs, proteins or peptide, nucleic acid molecules such as DNA, mRNA and siRNA, polysaccharides, lipids, and combinations thereof.

The specific therapeutic, prophylactic, or diagnostic agents encapsulated will depend upon the condition to be treated. For example, in compositions containing a polymeric matrix responsive to blood alcohol levels it may be advantageous to use one or more drugs commonly used for treating alcoholism or other addictions, i.e. disulfiram or calcium carbamide, diazepam or librium, or an opiate antagonists such as naloxone, naltrexone, cyclazocine, diprenorphine, etazocine, levalorphan, metazocine, or nalorphine.

Diagnostic agents may be release alone or in combination with therapeutic and/or prophylactic agents. Examples include radionuclides, radiopaque molecules, and MRI, x-ray or ultrasound detectable molecules.

C. Pharmaceutical Compositions

Pharmaceutical compositions containing an insulin derivative may be administered parenterally to subjects in need of such a treatment. Parenteral administration can be performed by subcutaneous, intramuscular or intravenous injection by means of a syringe, optionally a pen-like syringe. Alternatively, parenteral administration can be performed by means of an infusion pump. Further options are to administer the insulin nasally or pulmonally, preferably in compositions, powders or liquids, specifically designed for the purpose.

Injectable compositions of the insulin derivatives can be prepared using the conventional techniques of the pharmaceutical industry which involve dissolving and mixing the ingredients as appropriate to give the desired end product. Thus, according to one procedure, an insulin derivative can be dissolved in an amount of water which is somewhat less than the final volume of the composition to be prepared. An isotonic agent, a preservative and a buffer can be added as required and the pH value of the solution is adjusted—if necessary—using an acid, e.g., hydrochloric acid, or a base, e.g., aqueous sodium hydroxide, as needed. Finally, the volume of the solution can be adjusted with water to give the desired concentration of the ingredients.

In some embodiments, the buffer can be selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers and their combinations constitutes an alternative embodiment.

In some embodiments, the formulation can further comprise a pharmaceutically acceptable preservative which can be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In some embodiments, the preservative can be present in a concentration from 0.1 mg/ml to 20 mg/ml. In some embodiments, the preservative can be present in a concentration from 0.1 mg/ml to 5 mg/ml. In some embodiments, the preservative can be present in a concentration from 5 mg/ml to 10 mg/ml. In some embodiments, the preservative can be present in a concentration from 10 mg/ml to 20 mg/ml. Each one of these specific preservatives and their combinations constitutes an alternative embodiment. The use of a preservative in pharmaceutical compositions is well-known to the skilled person. For convenience reference is made to Remington: *The Science and Practice of Pharmacy*, current edition.

In some embodiments, the formulation can further comprise an isotonic agent which can be selected from the group consisting of a salt (e.g., sodium chloride), a sugar or sugar alcohol, an amino acid (e.g., glycine, L-histidine, arginine, lysine, isoleucine, aspartic acid, tryptophan, threonine), an alditol (e.g., glycerol (glycerine), 1,2-propanediol (propyleneglycol), 1,3-propanediol, 1,3-butanediol) polyethyleneglycol (e.g., PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. However, sugars that readily complex with phenylboronic acid can be avoided in compositions using insulin derivatives with a phenylboronic acid group. In some embodiments, the sugar additive can be sucrose. Sugar alcohol is defined as a $C_4$-$C_8$ hydrocarbon having at least one —OH group and includes, for example, mannitol, sorbitol, inositol, galactitol, dulcitol, xylitol, and arabitol. In some embodiments, the sugar alcohol additive can be mannitol. The sugars or sugar alcohols mentioned above can be used individually or in combination. There is no fixed limit to the amount used, as long as the sugar or sugar alcohol is soluble in the liquid preparation and does not adversely affect the effects achieved using the insulin derivatives (such as glucose-responsiveness). In some embodiments, the sugar or sugar alcohol concentration can be between about 1 mg/ml and about 150 mg/ml. In some embodiments, the isotonic agent can be present in a concentration from 1 mg/ml to 50 mg/ml. In some embodiments, the isotonic agent can be present in a concentration from 1 mg/ml to 7 mg/ml. In some embodiments, the isotonic agent can be present in a concentration from 8 mg/ml to 24 mg/ml. In some embodiments, the isotonic agent can be present in a concentration from 25 mg/ml to 50 mg/ml. Each one of these specific isotonic agents and their combinations constitutes an alternative embodiment. The use of an isotonic agent in pharmaceutical compositions is well-known.

Typical isotonic agents are sodium chloride, mannitol, dimethyl sulfone and glycerol and typical preservatives are phenol, m-cresol, methyl p-hydroxybenzoate and benzyl alcohol. Examples of suitable buffers are sodium acetate, glycylglycine, HEPES (4-(2-hydroxyethyl)-1-piperazineethanesulfonic acid) and sodium phosphate.

A composition for nasal administration of an insulin derivative can, for example, be prepared as described in European Patent No. 272097 (to Novo Nordisk A/S).

Compositions containing insulin derivatives can be used in the treatment of states which are sensitive to insulin. Thus, they can be used in the treatment of type 1 diabetes, type 2 diabetes and hyperglycaemia, for example, as sometimes seen in seriously injured persons and persons who have undergone major surgery. The optimal dose level for any subject will depend on a variety of factors including the efficacy of the specific insulin derivative employed, the age, body weight, physical activity, and diet of the patient, on a possible combination with other drugs, and on the severity of the state to be treated. It is recommended that the daily or periodic dosage of the insulin derivative of this invention be determined for each individual subject by those skilled in the art in a similar way as for known insulin compositions.

Where expedient, the insulin derivatives can be used in mixture with other types of insulin, e.g., insulin analogs with a more rapid onset of action. Examples of such insulin analogs are described, e.g., in the European patent applications having the publication Nos. EP 214826 (Novo Nordisk A/S), EP 375437 (Novo Nordisk A/S) and EP 383472 (Eli Lilly & Co.).

In some embodiments, the present compounds can be administered in combination with one or more further active substances in any suitable ratios. Such further active agents can be selected from antidiabetic agents, antihyperlipidemic agents, antiobesity agents, antihypertensive agents and agents for the treatment of complications resulting from or associated with diabetes. Suitable antidiabetic agents include insulin, GLP-1 (glucagon like peptide-1) derivatives such as those disclosed in WO 98/08871 (Novo Nordisk A/S), which is incorporated herein by reference, as well as orally active hypoglycemic agents.

Suitable orally active hypoglycemic agents preferably include imidazolines, sulfonylureas, biguanides, meglitinides, oxadiazolidinediones, thiazolidinediones, insulin sensitizers, α-glucosidase inhibitors, agents acting on the ATP-dependent potassium channel of the pancreatic β-cells, e.g., potassium channel openers such as those disclosed in WO 97/26265, WO 99/03861 and WO 00/37474 (Novo Nordisk A/S) which are incorporated herein by reference, potassium channel openers, such as ormitiglinide, potassium channel blockers such as nateglinide or BTS-67582, glucagon antagonists such as those disclosed in WO 99/01423 and WO 00/39088 (Novo Nordisk A/S and Agouron Pharmaceuticals, Inc.), all of which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antihyperlipidemic agents and antilipidemic agents, compounds lowering food intake, and PPAR (peroxisome proliferator-activated receptor) and RXR (retinoid×receptor) agonists such as ALRT-268, LG-1268 or LG-1069.

Insulin derivatives can be provided in the form of essentially zinc free compounds or in the form of zinc complexes. When zinc complexes of an insulin derivative are provided, two $Zn^{2+}$ ions, three $Zn^{2+}$ ions or four $Zn^{2+}$ ions can be bound to each insulin hexamer. Solutions of zinc complexes of the insulin derivatives will contain mixtures of such species.

In some embodiments, a pharmaceutical composition comprising a therapeutically effective amount of an insulin derivative together with a pharmaceutically acceptable carrier can be provided for the treatment of type 1 diabetes, type 2 diabetes and other states that cause hyperglycaemia in a subject in need of such a treatment. An insulin derivative can be used for the manufacture of a pharmaceutical composition for use in the treatment of type 1 diabetes, type 2 diabetes and other states that cause hyperglycaemia.

In some embodiments, there is provided a pharmaceutical composition for treating type 1 diabetes, type 2 diabetes and other states that cause hyperglycaemia in a subject in need of such a treatment, comprising a therapeutically effective amount of an insulin derivative in mixture with an insulin or an insulin analog which has a rapid onset of action, together with pharmaceutically acceptable carriers and additives.

In some embodiments, an insulin derivative which is soluble at physiological pH values is provided. In some embodiments, an insulin derivative according to the invention which is soluble at pH values in the interval from about 6.5 to about 8.5 is provided. In some embodiments, an insulin derivative which binds serum albumin is provided. In some embodiments, an insulin derivative which forms insulin hexamers is provided. In some embodiments, an insulin derivative which agglomerates is provided. In some embodiments, an insulin derivative which forms conjugates is provided.

In some embodiments, a pharmaceutical composition comprising an insulin derivative where the insulin derivative binds serum albumin is provided. In some embodiments, a pharmaceutical composition comprising an insulin derivative where the insulin derivative forms insulin hexamers is provided. In some embodiments, a pharmaceutical composition comprising an insulin derivative where the insulin derivative agglomerates is provided. In some embodiments, a pharmaceutical composition comprising an insulin derivative where the insulin derivative forms conjugates is provided.

In some embodiments, a pharmaceutical composition comprising an insulin derivative which is soluble at physiological pH values is provided. In some embodiments, a pharmaceutical composition comprising an insulin derivative according to the invention which is soluble at pH values in the interval from about 6.5 to about 8.5 is provided. In some embodiments, a pharmaceutical composition comprising an insulin derivative which binds serum albumin is provided. In some embodiments, a pharmaceutical composition comprising an insulin derivative which forms insulin hexamers is provided. In some embodiments, a pharmaceutical composition comprising an insulin derivative which agglomerates is provided. In some embodiments, a pharmaceutical composition comprising an insulin derivative which forms conjugates is provided.

In some embodiments, a pharmaceutical composition with a prolonged profile of action which comprises an insulin derivative is provided.

In some embodiments, a pharmaceutical composition which is a solution containing from about 50 U/ml to about 1000 U/ml, from about 200 U/ml to about 1000 U/ml, from about 200 U/ml to about 500 U/ml, from about 300 U/ml to about 1000 U/ml, or from about 300 U/ml to about 500 U/ml, of an insulin derivative or of a mixture of the insulin derivative with a rapid acting insulin analog is provided. One unit of native insulin is approximately 36 µg of insulin. Equivalent units for insulin derivatives and analogs will vary from this and can be determined by those of skill in the art.

In some embodiments, a pharmaceutical composition which is a solution containing from about 120 nmol/ml to about 2400 nmol/ml, from about 400 nmol/ml to about 2400 nmol/ml, from about 400 nmol/ml to about 1200 nmol/ml, from about 600 nmol/ml to about 2400 nmol/ml, or from about 600 nmol/ml to about 1200 nmol/ml of an insulin derivative or of a mixture of the insulin derivative with a rapid acting insulin analog is provided.

D. Glucose-Dependent Insulin-Binding Peptides

Insulin-binding peptides for facilitating glucose-dependent insulin activity and/or solubility are also provided. A combinatorial library of peptides which incorporate amino acids with glucose-responsive moieties, such as phenylboronic acid groups can be used to identify peptides that bind insulin and that, through that binding, affect activity and/or solubility of the insulin. Such effects of identified peptides can be used to alter bioavailability of insulin based on glucose concentration. Screening of the peptides can be accomplished by, for example, exposing immobilized insulin to the complete peptide library and washing with detergent to elute non-binding or weakly binding compounds. Finally, the immobilized insulin can be washed with varying concentrations of glucose and the eluted peptides collected as peptides with glucose-responsive insulin binding. This method allows rapid screening of a huge library on a manageable scale and will produce a subset of hits that are insulin binding.

The eluent containing the presumed insulin-binding sequences will be identified using mass spectrometry (MS) techniques. As it is assumed that the sample will be complex, peptides will be separated by a reversed-phase HPLC column in-line with the MS, and tandem MS/MS will be used to determine the peptide sequence. In order to improve the certainty of identification of hits, the eluent will be split into several fractions for independent sampling, and the same library will be screened 10 times by the protocol in 2, and hits will be ranked by the number of times that they appear in each of these screens.

The resultant peptide hits from MS screening will be resynthesized by solid phase techniques. These peptides hits will be separately incubated with insulin, and this insulin complex will be subsequently tested for insulin receptor activation when compared to native insulin in a cell-based assay. The envisioned assay will measure the level of phosphorylated Akt, a signaling intermediate downstream of the activated insulin receptor. In addition, insulin activity will be monitored in the presence of the peptide hit and hyperglycemic levels of glucose. This will validate whether suppression of insulin activity by the hit peptides is glucose-responsive.

The formulation of delivery of insulin with peptide hits will be examined to determine whether a more efficient glucose-responsive trigger can be generated. Using protein engineering, we can explore tethering the peptide to insulin using a flexible linker to improve the binding and responsiveness of the compound. In addition, multivalent peptide structures can be explored to evaluate whether the formation of higher order insulin-peptide aggregates could be used to improve the delivery and the potency of the therapy. The insulin-peptide complexes will also be formulated with existing drug delivery platforms, for example polymeric nanoparticles, to optimize drug delivery kinetics and protect both the insulin and peptide from enzymatic degradation.

The insulin/peptide formulation will be injected subcutaneously or intravenously into streptazotocin-induced diabetic mice. The blood glucose of these mice will be monitored to determine the efficacy and duration of glycemic correction, including probing the insulin-responsiveness by bolus glucose challenge of reversed mice, and monitoring for the appropriate dose to ensure long-term normoglycemia. For short-term effect studies, blood glucose will be monitored every 30 minutes after injection until 8 hours. For long-term effect studies, blood glucose will be monitored 4 times a day for 2 weeks. Promising candidates will be evaluated in additional models with help from Sanofi for both safety and efficacy.

II. Methods of Making Glucose-Responsive Compositions

A. Methods of Making Derivatized Insulin

Insulin or insulin analogs can be derivatized using any suitable techniques. The starting product for the acylation of the parent insulin or insulin analog or a precursor thereof can be produced by either well-known organic synthesis or by well-known recombinant production in suitable transformed microorganisms. Thus the insulin starting product can be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture. As an example desB(30) human insulin can be produced from a human insulin precursor B(1-29)-Ala-Ala-Lys-A(1-21) which is produced in yeast as disclosed in U.S. Pat. No. 4,916,212. This insulin precursor can then be converted into desB30 human insulin by ALP cleavage of the Ala-Ala-Lys peptide chain to give desB30 human insulin which can then be acylated to give the present insulin derivatives.

B. Dosage Forms

Dosage forms may be formulated in a conventional manner using one or more physiologically acceptable carriers comprising known excipients and auxiliaries which facilitate processing into preparations which can be used pharmaceutically. In one embodiment, prior to injection, the formulation is in the form of a suspension.

Formulation of drugs is discussed in, for example, Hoover, John E., Remington's Pharmaceutical Sciences, Mack Publishing Co., Easton, Pa. (current edition), and Liberman, H. A. and Lachman, L., Eds., Pharmaceutical Dosage Forms, Marcel Decker, New York, N.Y. (1980). Proper formulation is dependent upon the route of administration chosen.

In a preferred embodiment, the formulation is an injectable formulation. An injectable insulin formulation can be made by suspending the insulin derivative in a diluent. The suspension is sterilized and filled in a vial suitable for unit or multiple injection dosing. Sterile injectable preparations may be formulated as known in the art. Among the acceptable vehicles and solvents that may be employed are water, Ringer's solution, U.S.P. and isotonic sodium chloride solution. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use. Components and compositions for such formulations are described further elsewhere herein.

IV. Methods of Using Compositions

A. Methods of Administration

The formulations can be administered subcutanteously, intramuscularly, or intradermally. In preferred embodiment, the formulation is injected subcutaneously.

In some embodiments, there is provided a method of treating type 1 diabetes, type 2 diabetes and other states that cause hyperglycaemia in a subject in need of such a treatment, comprising administering to the subject a therapeutically effective amount of an insulin derivative together with a pharmaceutically acceptable carrier and pharmaceutical acceptable additives.

In some embodiment, there is provided a method of treating type 1 diabetes, type 2 diabetes and other states that cause hyperglycaemia in a subject in need of such a treatment, comprising administering to the subject a therapeutically effective amount of an insulin derivative in mixture with an insulin or an insulin analogue which has a rapid onset of action, together with a pharmaceutically acceptable carrier and pharmaceutical acceptable additives.

In some embodiments, there is provided a use of an insulin derivative for the manufacture of a medicament for blood glucose lowering. In some embodiments, there is provided a use of an insulin derivative for the manufacture of a medicament for treatment of diabetes.

"Dosage unit form" as used herein refers to a physically discrete unit of conjugate appropriate for the patient to be treated. In one embodiment, the formulation is an insulin formulation designed to release insulin into systemic circulation over time with a basal release profile following injection in a patient. In another embodiment, the formulation is designed to release insulin into systemic circulation over time with a non-basal release profile following injection in a patient. Exemplary non-basal release profiles include a regular human insulin release profile and a prandial release profile. In one embodiment the formulation is designed to release insulin into systemic circulation over time with a regular human insulin release profile following injection in a patient. In another embodiment, the formulation is designed to release insulin into the systemic circulation over time with a prandial release profile following injection in a patient.

B. Subjects to be Treated

The compositions and formulations including a responsive composition can be administered to a subject in need of delivery of a therapeutic, prophylactic, or diagnostic agent in a responsive manner. In a preferred set of embodiments, the patient is in need of administration of a therapeutic agent in response to increases in blood glucose levels, i.e., due to diabetes.

Figure 7:
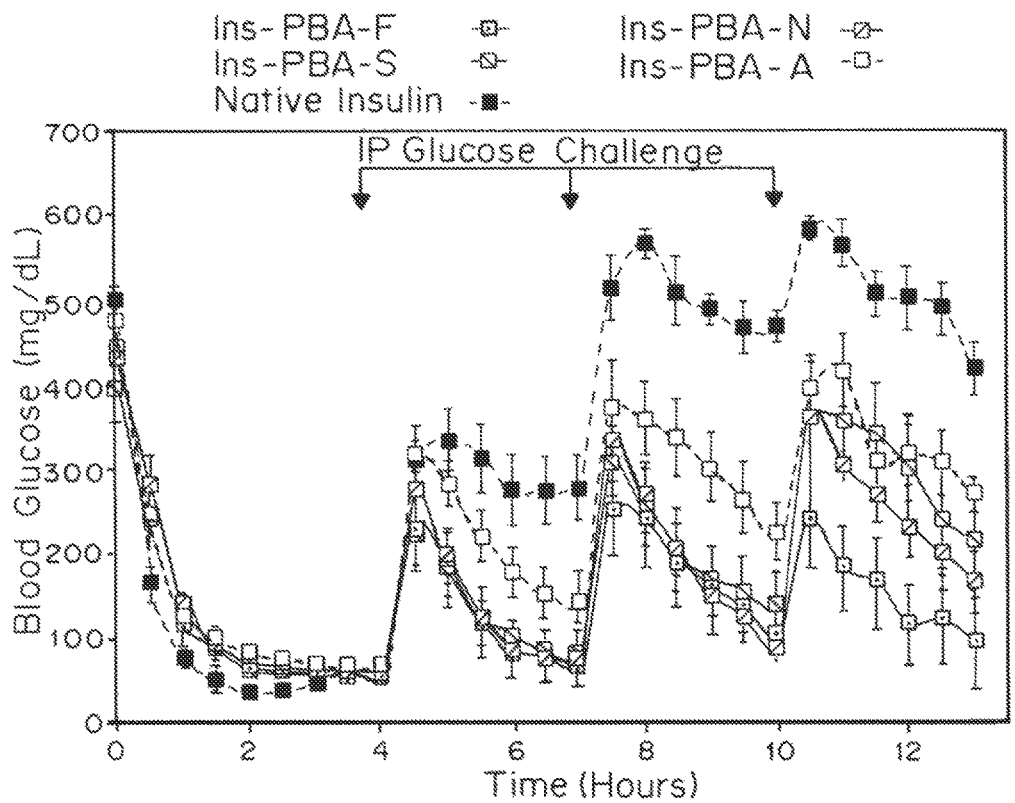
FIG. 7 is a graph of blood glucose over time using 4 modified insulin derivatives. The insulin derivatives were injected at t=0 and then intraperitoneal glucose tolerance tests were performed at 4, 7, and 10 hours. All analogues demonstrate superior recovery following challenge compared to native insulin. The order of the graph lines after 6 hours are, from top to bottom, native insulin and Ins-PBA-A, with the rest overlapping. The order of the graph lines after 9 hours are, from top to bottom, native insulin and Ins-PBA-A, with the rest overlapping. The order of the graph lines after 12 hours are, from top to bottom, native insulin, Ins-PBA-A, Ins-PBA-S, Ins-PBA-N, and Ins-PBA-F.

In some embodiments, as the patient's blood glucose levels rise, the glucose complexes with a glucose-sensing component, such as phenylboronic acid (PBA). The complexation of glucose alters the chemical and/or physical properties of the insulin derivative such that release of the insulin is facilitated. For example, insulin derivatives can bind serum albumin (thus keeping the insulin from being bioavailable) based on the chemical and/or physical properties of the insulin derivative. When glucose complexes with the insulin derivative, the properties of the insulin derivative changes (such as by increasing the aqueous solubility of the insulin derivative), thus facilitating release of the insulin derivative from the albumin. As the patient's blood glucose levels rise, the glucose binds to the glucose binding portion of the insulin derivative, disrupting interactions contributing to albumin binding or agglomeration of the insulin derivative. The interaction with glucose leads to release of the insulin derivative in a blood glucose-dependent manner as shown in FIG. 7.

In some embodiments, the insulin formulation is administered to patients who are not fully insulin dependent. In one embodiment, the formulation provides a sufficient amount of insulin to the patient during the day so that the patient does not require additional insulin-containing formulations to maintain his/her blood glucose levels within a safe range. The patient is typically not fully insulin dependent.

In another embodiment, the formulation is administered to a patient who is receiving intensive insulin therapy as one of the insulin-containing formulations administered to the patient during the day. Preferably the formulation delivers insulin to the patient with a basal release profile.

As used herein, "controlling blood glucose levels" refers to the maintenance of blood glucose concentrations at a desired level, typically between 70-130 mg/dL or 90-110 mg/dL.

In preferred embodiments, the formulation when administered to a patient with diabetes is able to maintain normoglycemia (normal glycemic levels) for a period of up to 2 days, 5 days, 1 week, 2 weeks, one month, or up to two months.

The present invention will be further understood by reference to the following non-limiting examples.

EXAMPLES

Example 1

Synthesis and Testing of Long-Acting Insulin Derivatives

This example demonstrates the synthesis and development of several classes of long-acting insulin derivatives that have been designed to afford glucose-mediated binding to serum albumin to prepare glucose-responsive insulin. This was achieved by combining a lipidic or hydrophobic moiety to facilitate binding of serum albumin (or other proteins, such as globulin, lipoprotein complexes-HDL, LDL, etc.) with a phenylboronic acid (PBA) moiety, a class of molecules known to bind to glucose and other cis-1,2 or cis-1,3 diols. PBA compounds and PBA-containing polymers have previously demonstrated utility in glucose sensing and insulin delivery. However, direct conjugation of PBA to insulin has not yet been demonstrated to afford glucose-mediated control of insulin activity.

A. Phenylboronic Acids for Glucose Sensing

The insulin derivatives described in this example represent three separate libraries of modified insulins. All insulin derivative in this example are modified via the B29 lysine to contain a hydrophobic component as well as a phenylboronic acid (PBA), which can bind to glucose. FIG. 1 illustrates some representative PBA structures that can be incorporated into the design of these modified insulins. PBAs useful for this purpose can take many forms. Four structures were explored in the design of the molecules described in this example, but molecular design can be broadened to include any of a number of PBA chemistries, as illustrated in FIG. 1.

B. Lipid-Modified Insulin Derivatives (Library 1)

Figure 2:
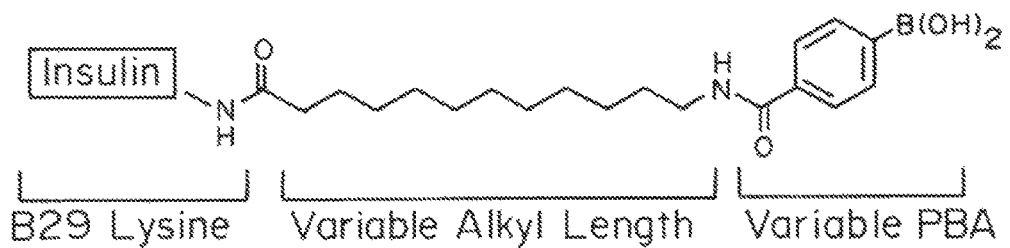
FIG. 2 is a diagram of the structures of example of lipid-modified insulin derivatives, with a variable-length alkyl segment terminated in one of several PBAs.

Example structures for the first library of modified insulins are shown in FIG. 2. The full library of synthetized compounds can be found in Library 1. This insulin library consists of modification of the B29 lysine on insulin via an alkyl segment terminated with a phenylboronic acid. Hydrophobic moieties, such as alkyl segments, are known to interact with hydrophobic domains of serum albumin, and form the basis for the effect observed by long-lasting insulin (detemir). This general scheme is illustrated in FIG. 2. This modular approach affords control over the length of the alkyl segment and control over the type of PBA used, including any of the structures shown in FIG. 1.

C. Bile Acid Modified Insulins (Library 2)

Figure 3:
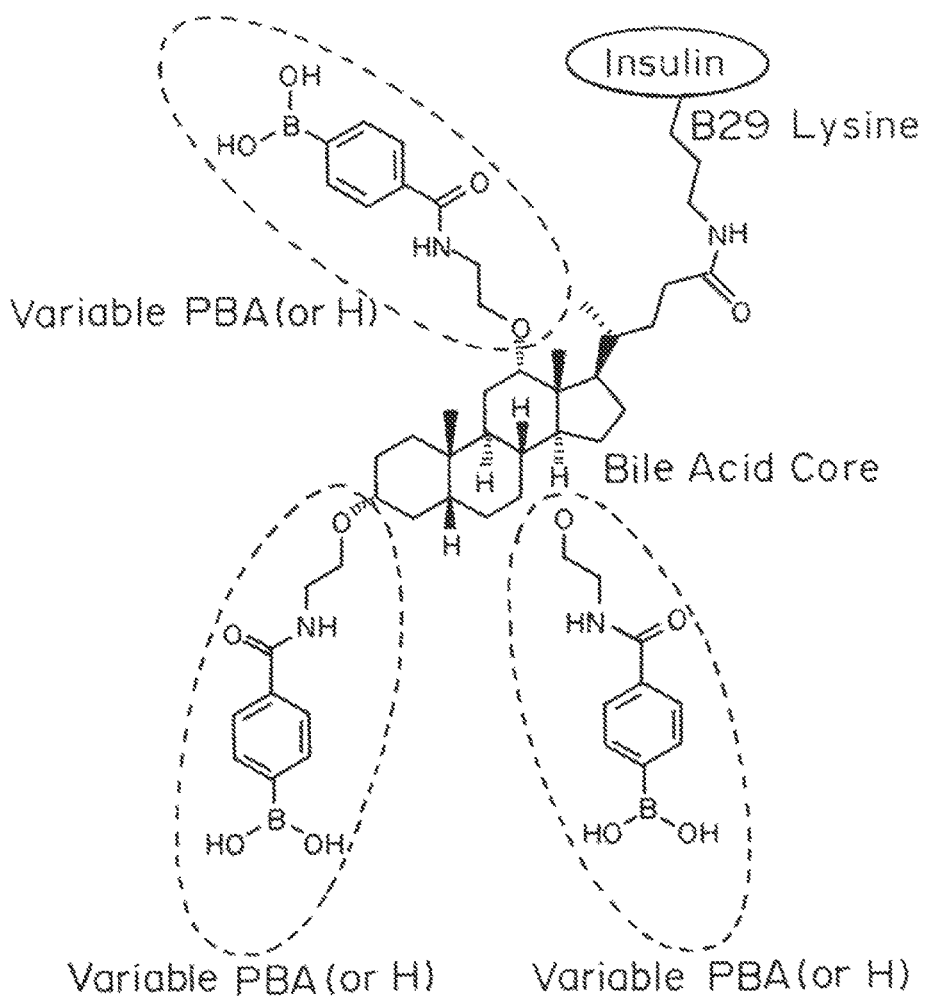
FIG. 3 is a diagram of an example of a bile acid insulin conjugate. Bile acid (cholic acid in this instance) is attached via the B29 lysine residue, and modified with between 1 and 3 variable PBAs.

An example structure for the second library of modified insulins are shown in FIG. 3. The full library of synthetized compounds can be found in Library 2. These insulins are modified with a bile acid conjugated to between 1 and 3 PBAs. Bile acids, including cholic acid, lithocholic acid, hyocholic acid, deoxycholic acid, hyodeoxycholic acid, and chenodeoxycholic acid, can be used as a core for these structures. Bile acids are known to be strong binders to serum albumin, to afford the insulin with long-lasting properties. These bile acids can be modified at hydroxyl groups located at several different positions within the structure. As with the past library, any of a number of PBAs could be added at these positions. Based on the availability of different bile acids with varying number of hydroxyl groups for modification, bile acid conjugates could have between 1-3 PBAs attached to the central bile acid core, with any PBA from the examples shown in FIG. 1 being suitable. The PBAs afford glucose sensing properties. This is illustrated in FIG. 3, with the example showing a cholic acid core modified at 3 sites with a phenylboronic acid, attached via an ethanolamine spacer. This spacer length is, similarly variable.

D. Pseudolysine-Modified Insulin Derivatives (Library 3)

Figure 4:
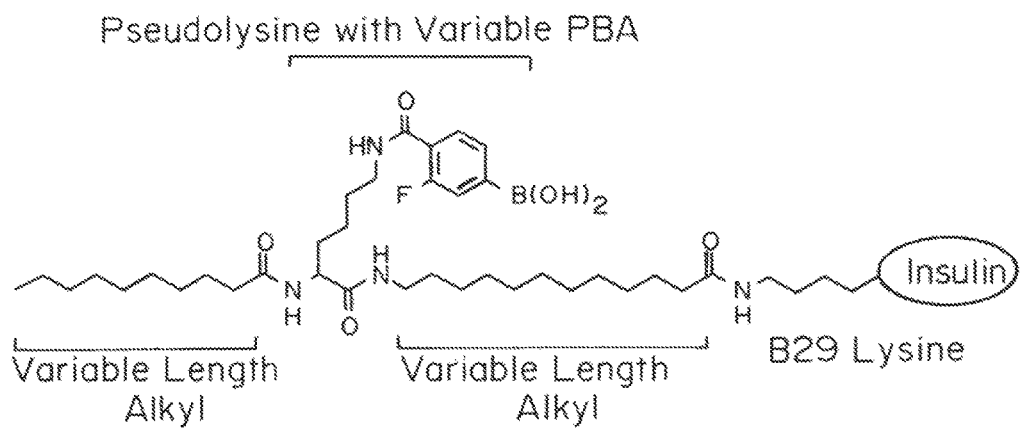
FIG. 4 is a diagram of an example of pseudolysine insulin conjugate. An amino acid (lysine or other amine-containing R-group) is installed between two tunable alkyl segments to modify length of the hydrophobic segment.

An example of a pseudolysine-modified insulin library is shown in FIG. 4. The full library of synthetized compounds can be found in Library 3. This library combines a PBA off of a lysine residue. A similar amine-containing amino acid could also be used, such as ornithine or aminopropanoic acid. Any of the PBAs shown in FIG. 1 could be used to modify this amine and provide the ability to bind to glucose. This PBA-containing amino acid is flanked by 2 alkyl segments of variable length to facilitate binding with serum albumin. As with the other modification strategies, the small molecule is again attached to the B29 lysine of insulin.

E. Results

Figure 5A:
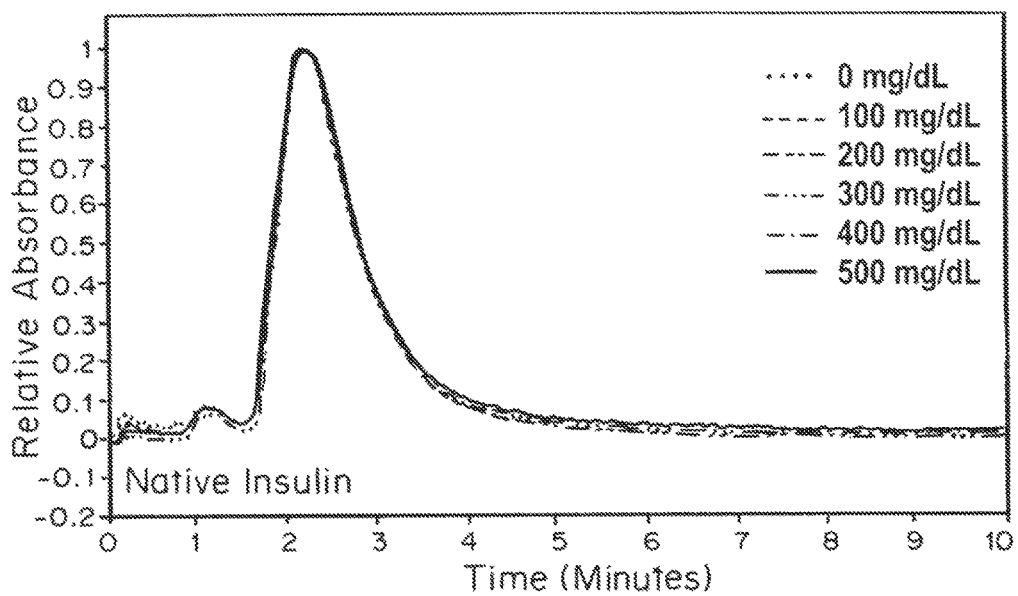
FIGS. 5a, 5b, and 5c are graphs of serum albumin chromatography showing native insulin (a), standard long-lasting insulin detemir (LA-C14) (b) and one of the glucose-responsive insulin variants (c). For (c), the order of the graph lines between 2 and 3 minutes are, from top to bottom, 0, 200, 100, 300, 400, and 500 mg/dL.
Figure 5B:
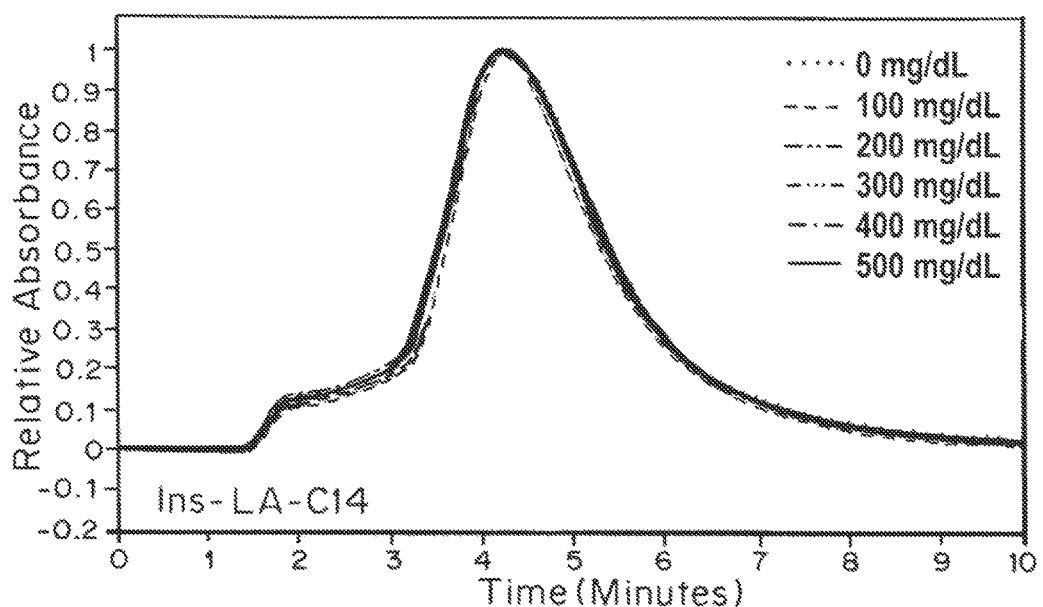
Figure 5C:
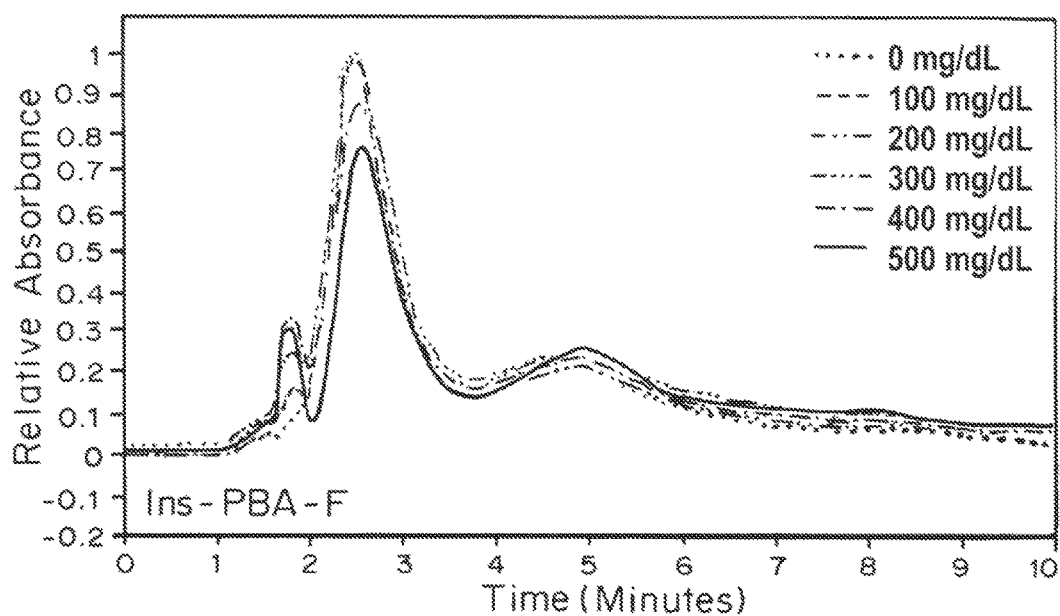

Long-lasting glucose-responsive insulins of the type proposed here are designed for the ability to undergo glucose-mediated binding to serum albumin. As a first means of assessing their function, chromatography with a serum albumin solid support can inform glucose-dependent binding to albumin. An example of this is shown in FIG. 5. The shift in retention as the glucose concentration of the mobile phase suggests a glucose-mediated decrease in binding affinity for the chemically modified insulin (in this case Ins-PBA-F). Insulins of this type may be useful as both long-acting and glucose-responsive insulin derivatives.

Figure 6:
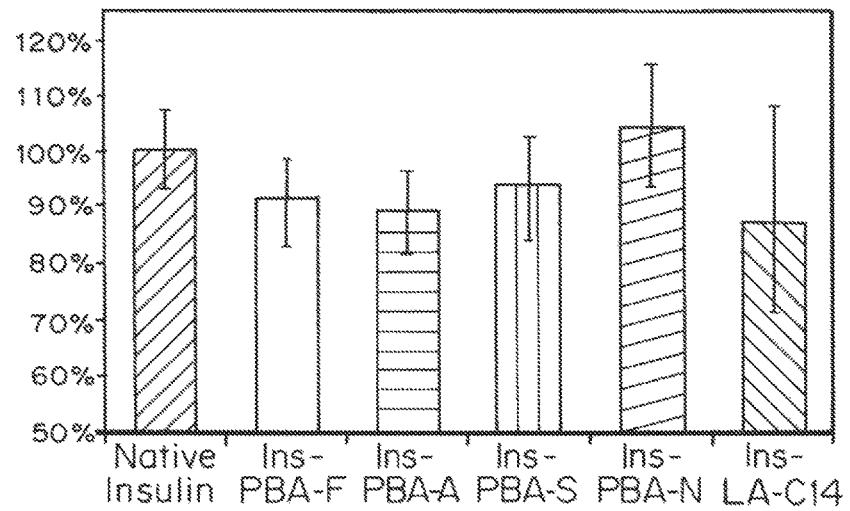
FIG. 6 is a graph the relative insulin activity of 4 PBA-modified insulin variants compared to insulin detemir (Ins-LA-C14), all of which have been modified via the B29 lysine of insulin. No significant change in activity was observed for any of the modified variants.

Chemically modifying insulin has the potential to inhibit the normal function of the protein. It is speculated that modification specifically via the B29-lysine amine preserves insulin function. An in vitro assay to verify activation of the insulin receptor demonstrates that insulins modified via this position have retained function and ability to signal through this receptor. FIG. 6 illustrates these findings, with none of the 5 modified insulins shown demonstrating significant reduction in function compared to a control of unmodified native insulin.

Long-lasting glucose-responsive insulins of the type proposed here should have long-term activity and be able to reduce blood glucose levels upon challenge with insulin. A mouse model of insulin-deficient diabetes, prepared using streptozotocin to poison pancreatic B-cells, was used to verify activity and function for the modified insulins developed here. As an example, PBA-modified insulin derivatives tested using this method reduced blood glucose levels to within a normoglycemic (<200 mg/dL) range following a single subcutaneous administration (FIG. 7). A comparable dose of native insulin also reversed hyperglycemia, but demonstrated a brief period of hypoglycemia (BG<50 mg/dL). Four hours following administration, an intraperitoneal glucose tolerance test (IPGTT) was administered. Following a spike in blood glucose levels, each of the PBA-modified insulin derivatives restored blood glucose to a normoglycemic level, whereas native insulin failed to reduce blood sugar. Of note, Ins-PBA-S, Ins-PBA-F, and Ins-PBA-N derivatives reversed blood glucose to pre-challenge levels. A second IPGTT performed 7 hours following insulin administration demonstrated that Ins-PBA-S, Ins-PBA-F, and Ins-PBA-N were again able to restore normoglycemic levels. Ins-PBA-A was not able to restore normoglycemia following the second challenge. A third IPGTT performed at 10 hours following insulin administration revealed that Ins-PBA-F and Ins-PBA-N were still able to restore normoglycemia, and Ins-PBA-F was especially potent in reversing blood glucose levels to pre-challenge values.

Figure 8A:
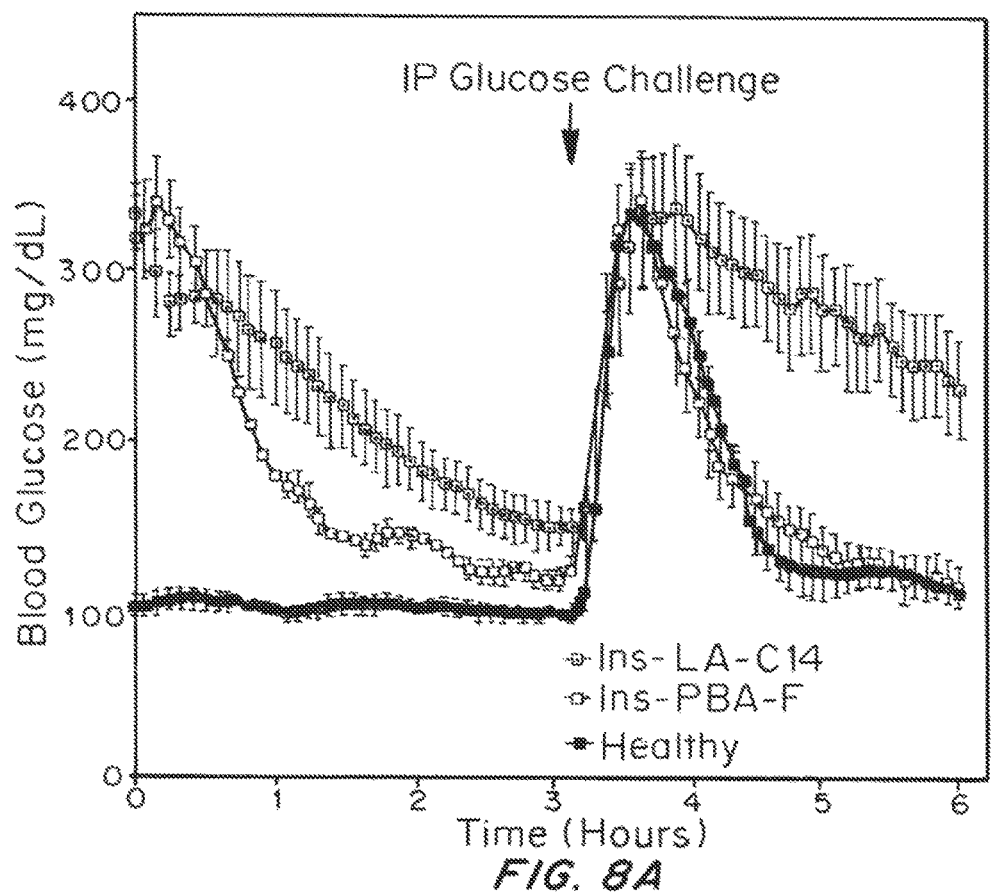
FIGS. 8a, 8b, 8c, and 8d are graphs of results from continuous glucose monitoring in mice treated with one PBA-modified insulin derivative (Ins-PBA-F) compared to a normal long-acting but non-glucose responsive version (Ins-LA-C14) as well as a healthy animal with a fully functioning pancreas. (a) Blood glucose levels over time with an intraperitoneal glucose tolerance test at 3 hours. The order of the graph lines at 2 hours are, from top to bottom, Ins-LA-C14, Ins-PBA-F, and healthy individual. The order of the graph lines at 5 hours are, from top to bottom, Ins-LA-C14, Ins-PBA-F, and healthy animal. (b) Initial slope following insulin administration. The graph line with the lower slope is Ins-LA-C14. (c) Slope following glucose challenge, and (d) area under the curve for response to glucose challenge. The graph line with the lower slope is Ins-LA-C14. The slopes of Ins-PBA-F and healthy animal are higher and nearly overlapping.
Figure 8B:
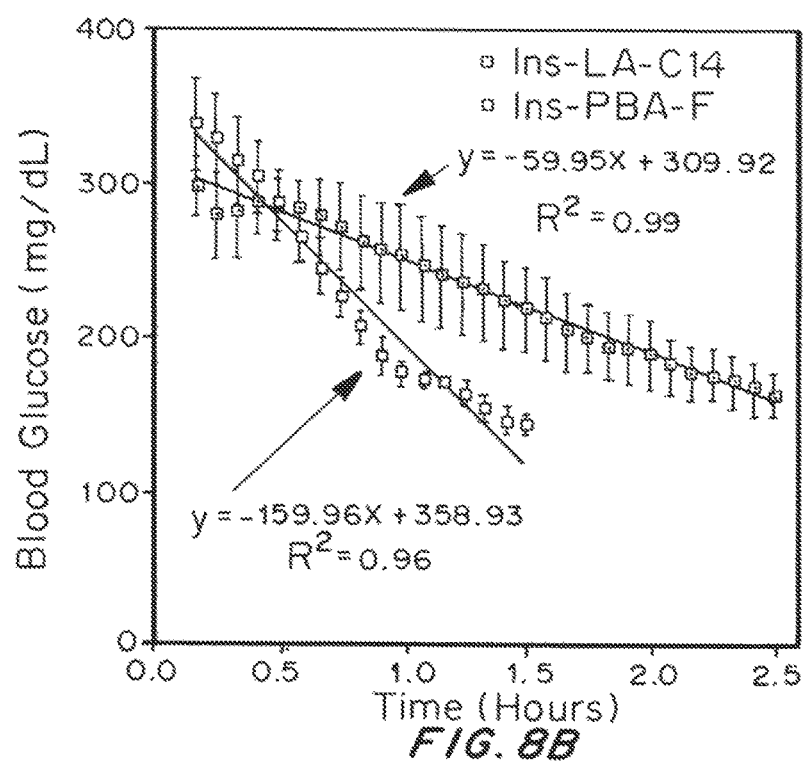
Figure 8C:
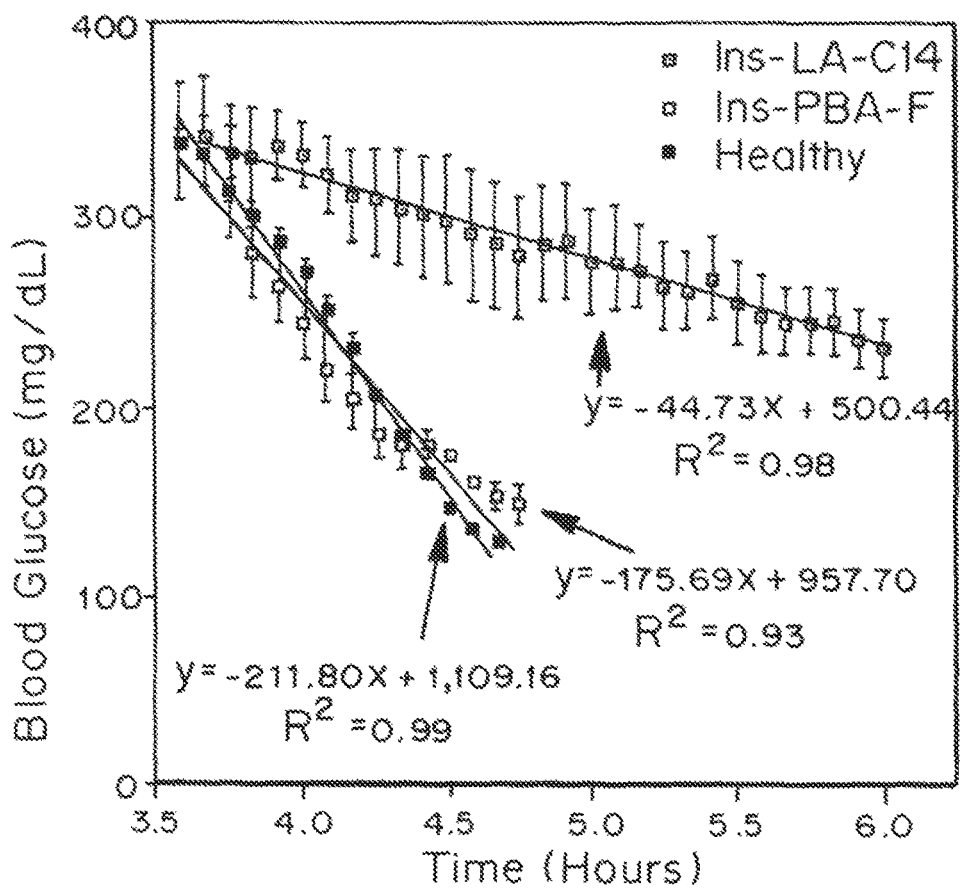
Figure 8D:
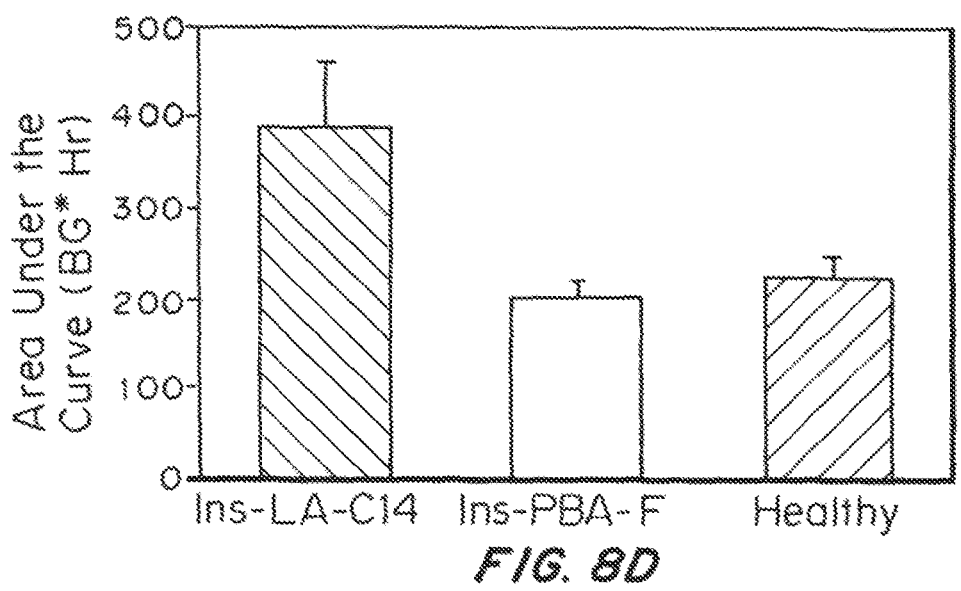

To further verify that the kinetics and responsiveness of PBA-modified insulin derivatives following IPGTT are actually glucose responsive, continuous glucose monitoring was used to provide five-minute resolution for blood glucose measurements. In these studies, our best performing insulin (Ins-PBA-F) was compared to the active ingredient of a clinically used long-acting insulin formulation (Ins-LA-C14) in insulin-deficient mice (FIG. 8a). Healthy age-matched mice were used as a positive control (gold standard for glucose responsiveness). Following administration, both insulin derivatives reversed blood glucose to normoglycemic levels, but the slope of this decrease was significantly faster for Ins-PBA-F than for Ins-LA-C14 (FIG. 8b). An IPGTT was performed 3 hours following insulin administration. Injection of glucose prompted a comparable rise in blood glucose levels in all groups. However, in the case where mice were treated with Ins-PBA-F, a rapid reversal was observed following challenge that was similar in slope to the response seen for a healthy mouse with no insulin deficiency (FIG. 8c). In the case of the long acting variant, Ins-LA-C14, the response following glucose challenge was much slower than both the Ins-PBA-F and healthy control. While the slopes between insulin treatments varied considerably, the slopes for each individual treatment after initial administration and following IPGTT were similar. Quantifying the area under curve beginning with the IPGTT at 3 hours and continuing until the 6-hour endpoint of the study, the responsiveness of Ins-PBA-F was similar to that for a healthy animal, while the Ins-LA-C14 had a much larger area and does not return to baseline over the timeframe integrated (FIG. 8d).

Figure 9A:
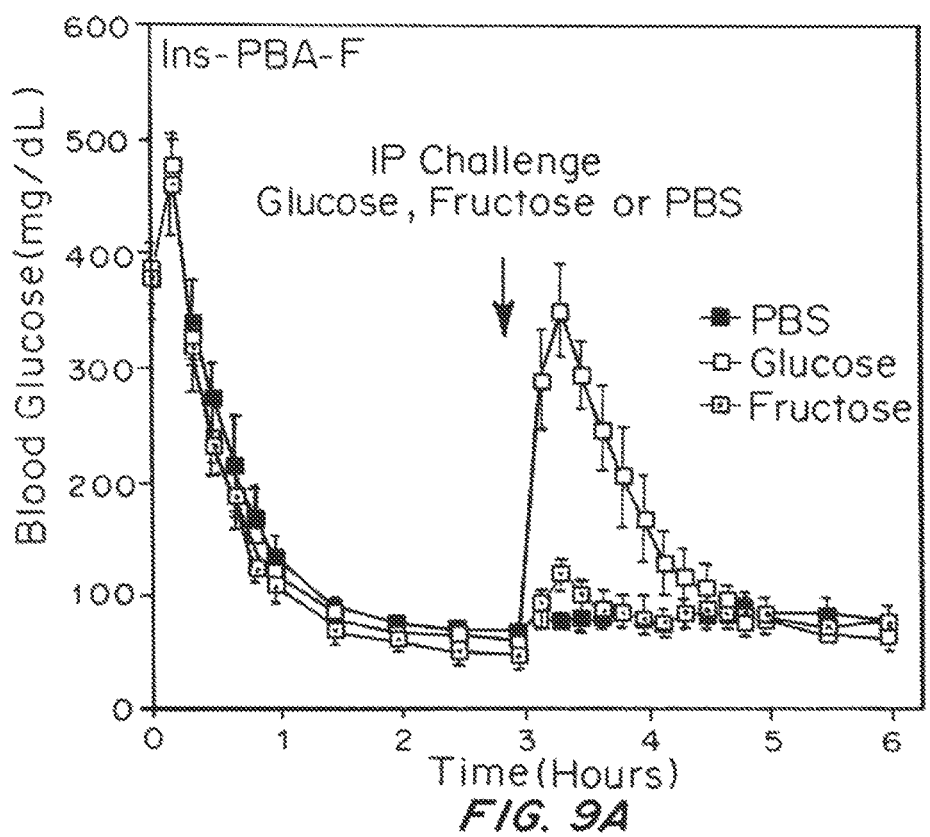
FIGS. 9a and 9b are graphs of blood glucose levels over time using insulin derivatives with an intraperitoneal tolerance test at 3 hours with glucose, fructose (a non-glucose diol), and PBS. (a) Results using PBA-modified insulin Ins-PBA-F. The order of the graph lines at 3⅓ hours are, from top to bottom, glucose, fructose, and PBS. (b) Comparison study performed with a standard long-acting insulin (Ins-LA-C14) that does not have a PBA modification. The order of the graph lines at 3⅓ hours are, from top to bottom, glucose, fructose, and PBS. The order of the graph lines at 6 hours are, from top to bottom, fructose, glucose, and PBS.
Figure 9B:
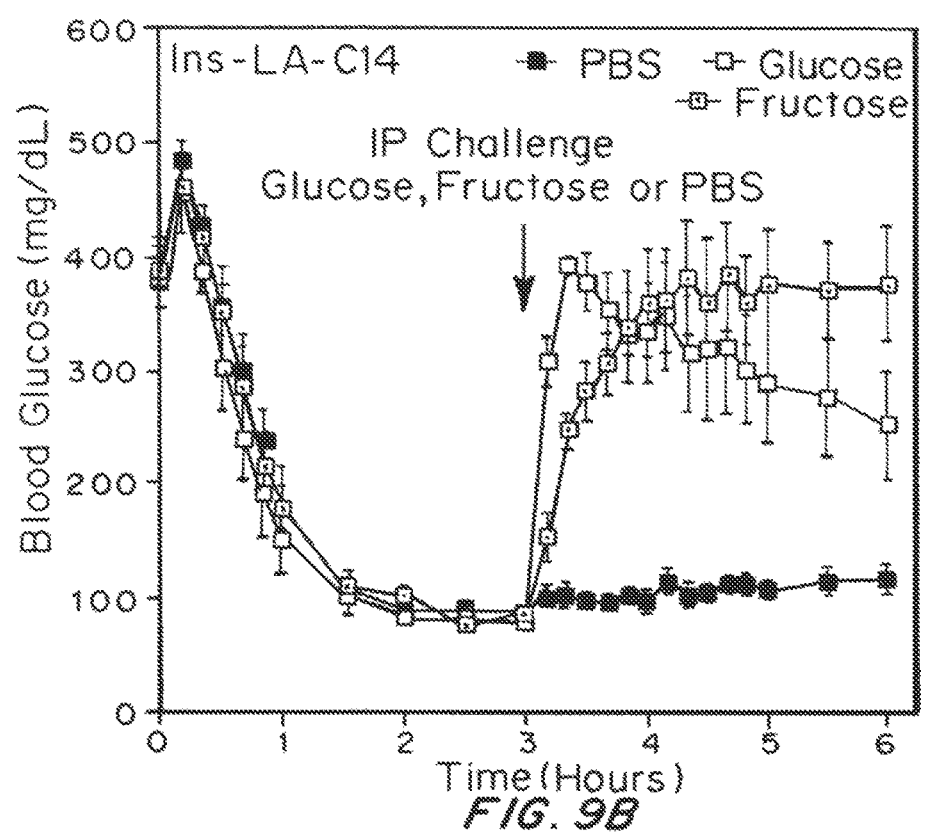
Figure 10:
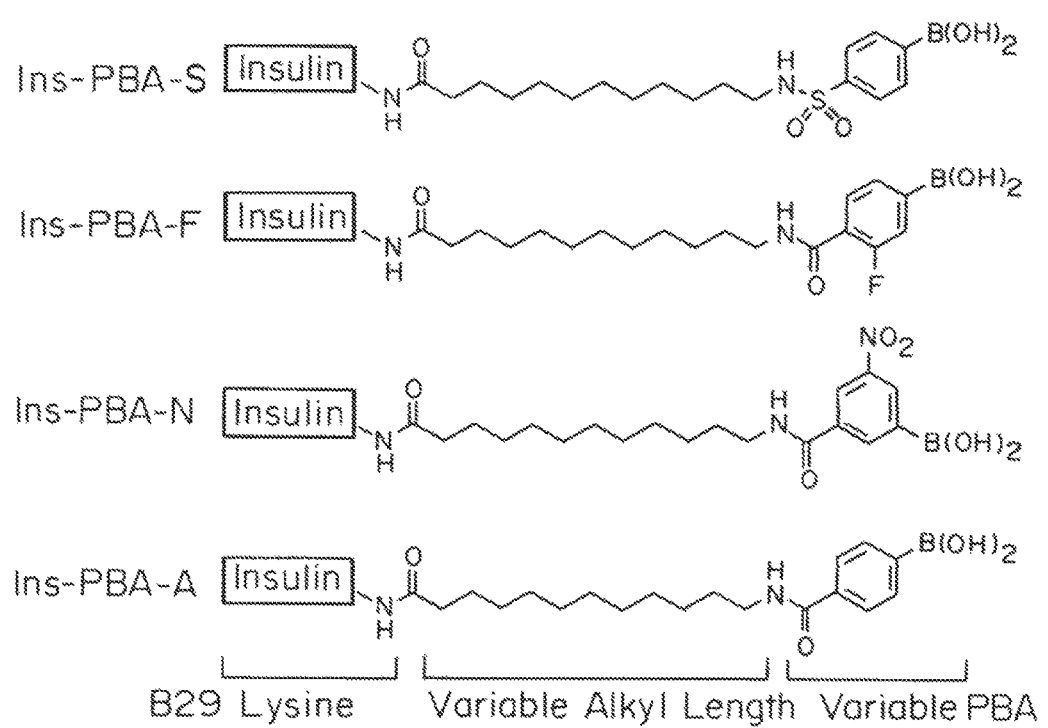
FIG. 10 is a diagram of the structures of example derivatized insulins in Library 1.
Figure 11A:
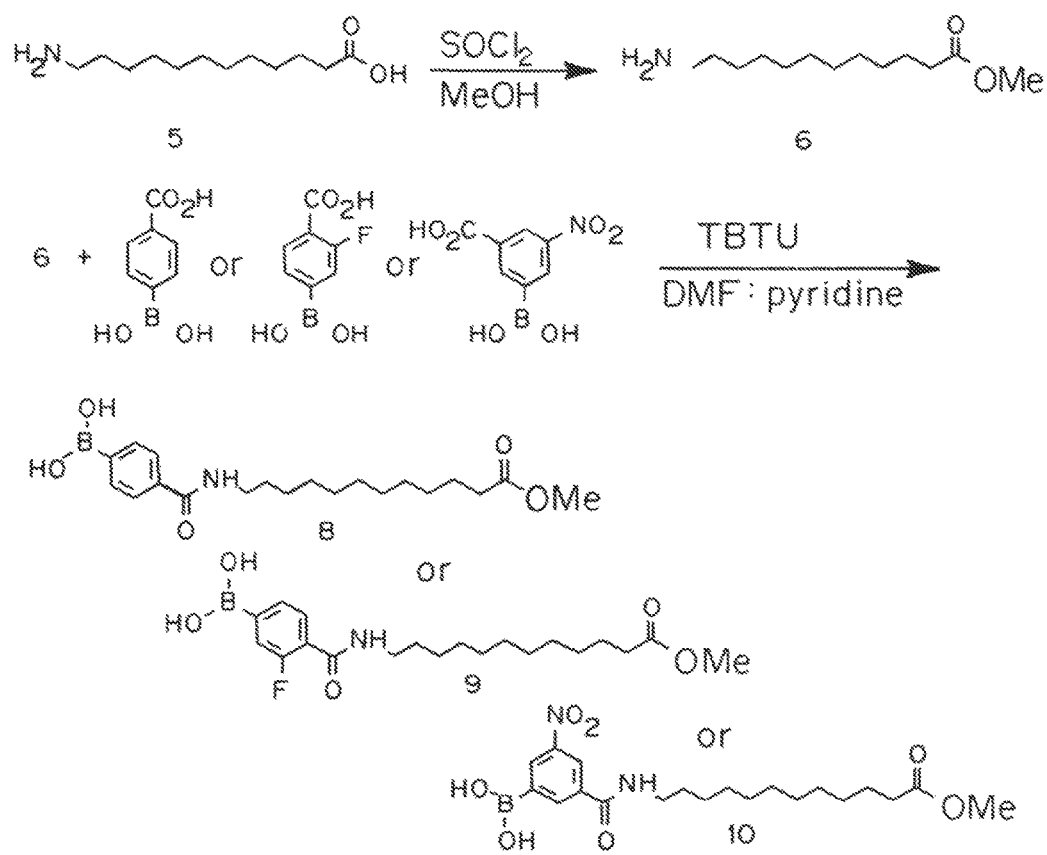
FIGS. 11A and 11B are diagrams showing an example of the synthetic scheme for making example derivatized insulins in Library 1.
Figure 11B:
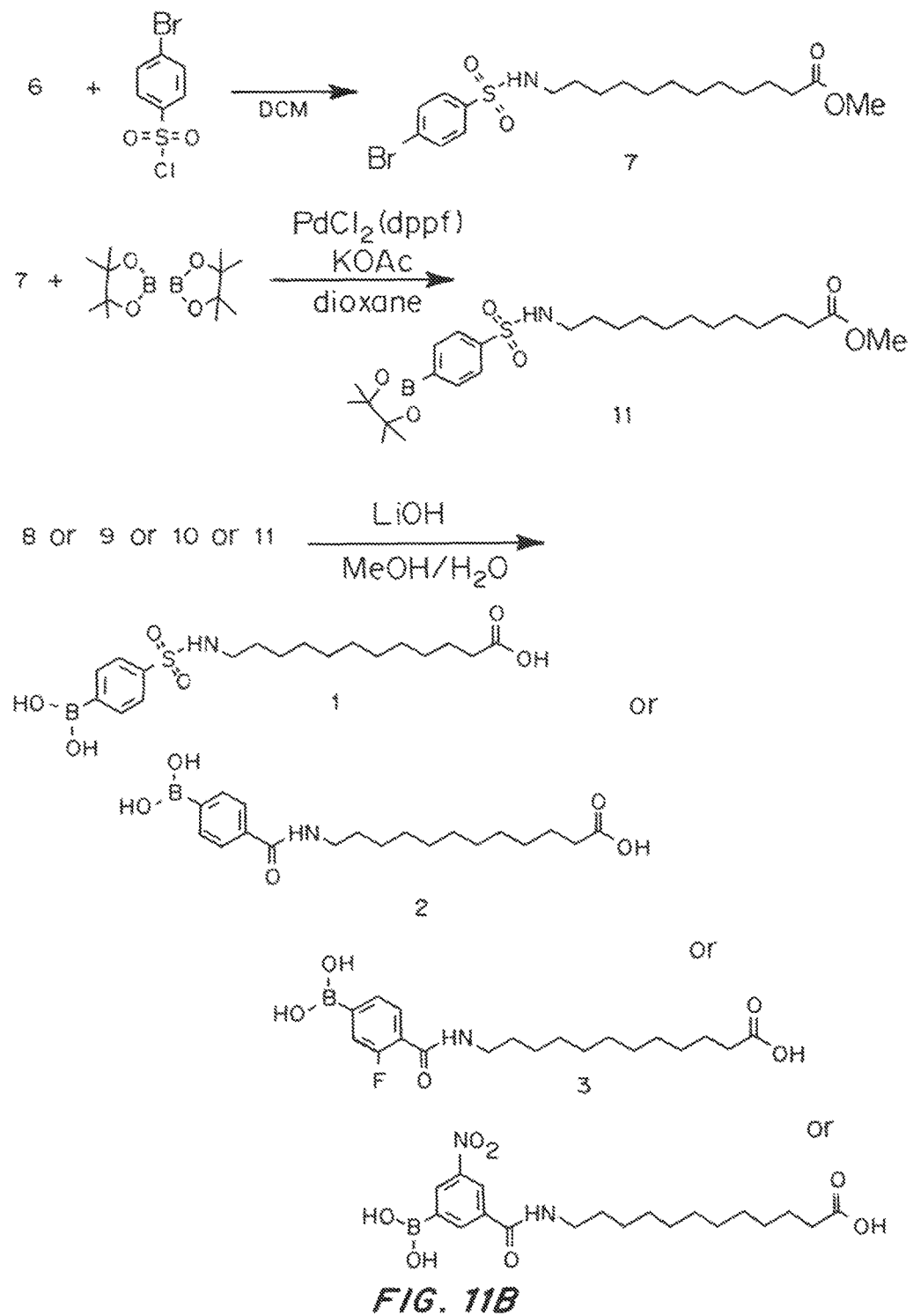
Figure 12:
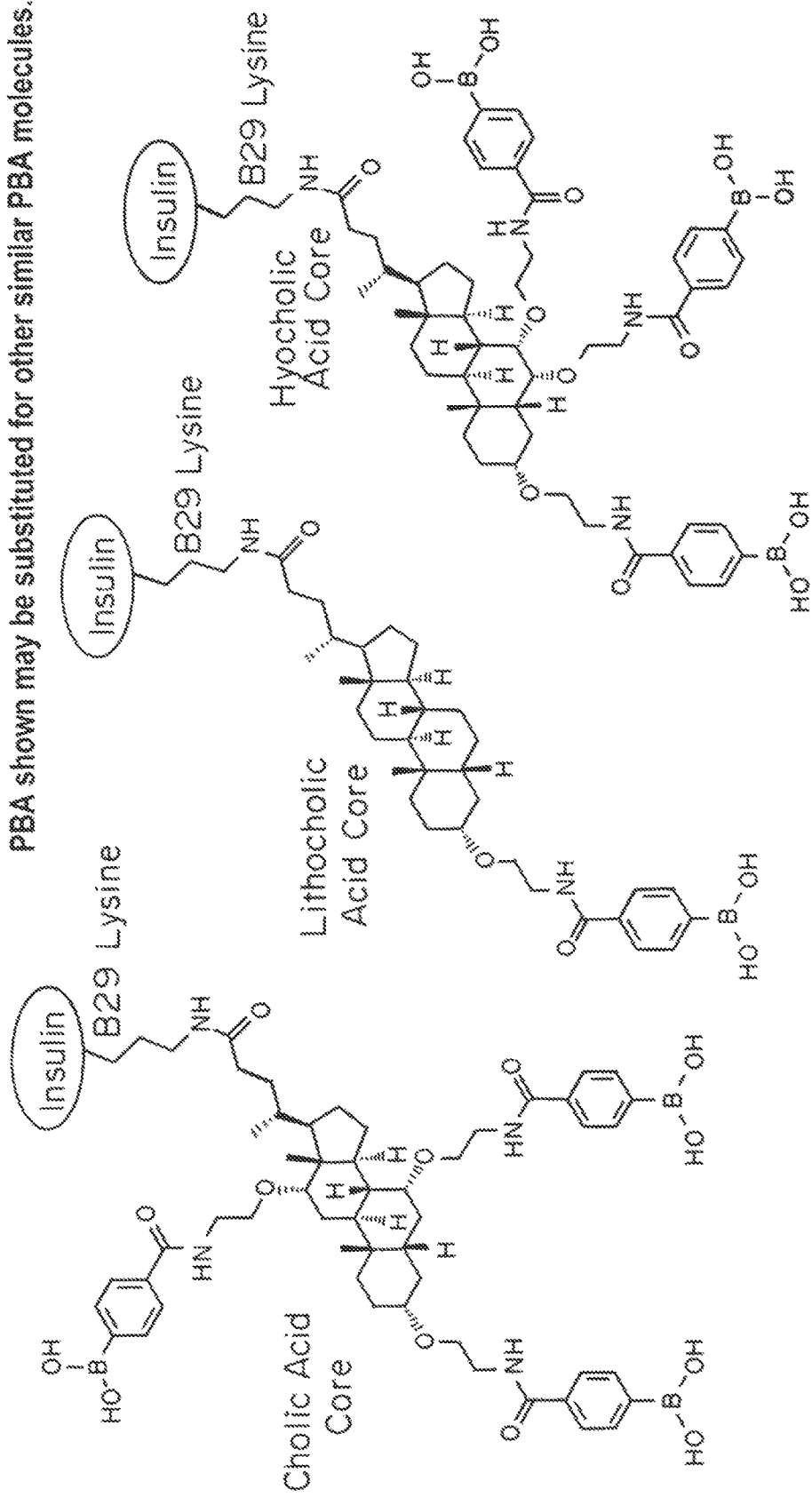
FIG. 12 is a diagram of the structures of example derivatized insulins in Library 2.
Figure 12:
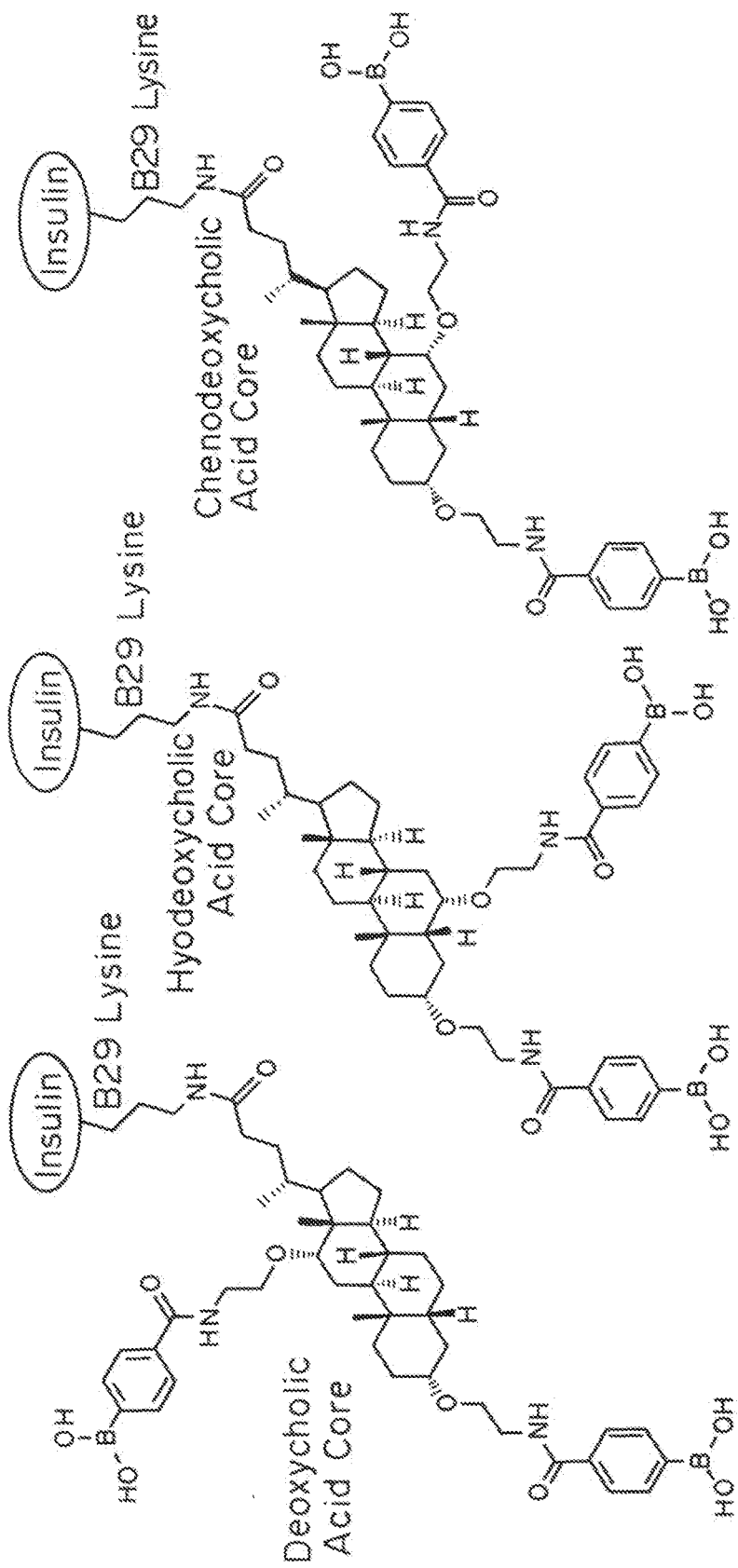
Figure 13A:
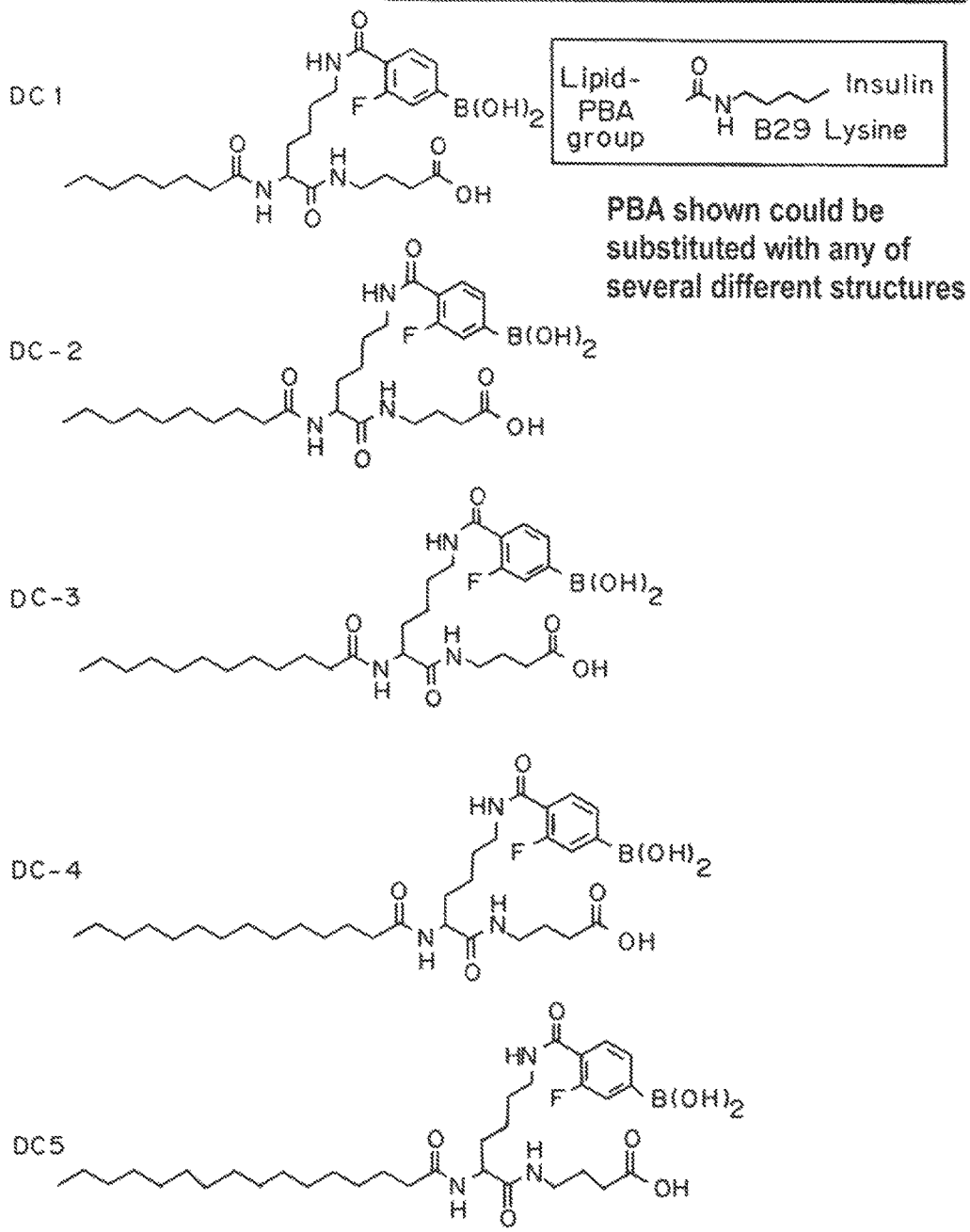
FIGS. 13A, 13B, and 13C are diagrams of the structures of example derivatized insulins in Library 3.
Figure 13B:
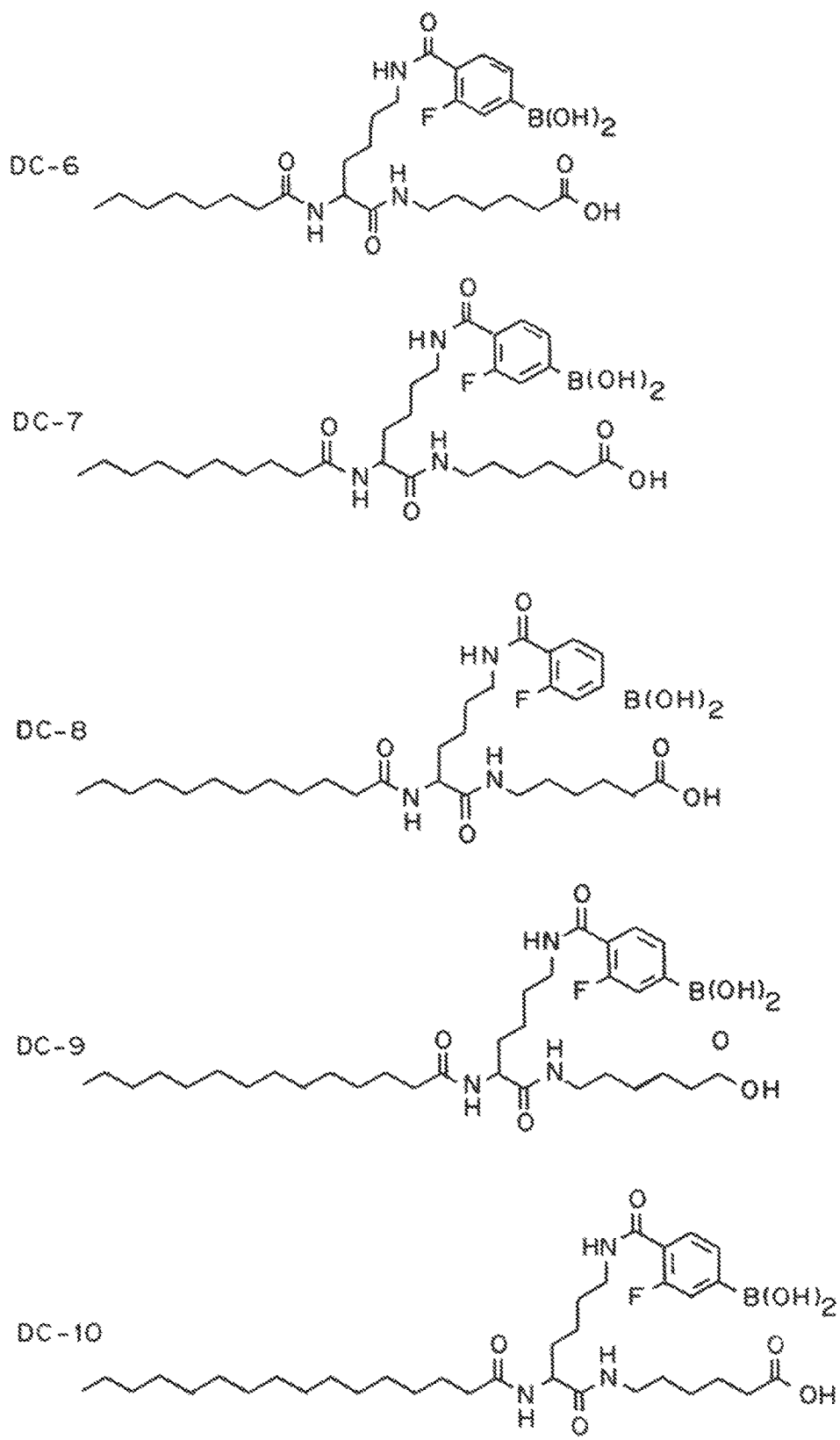
Figure 13C:
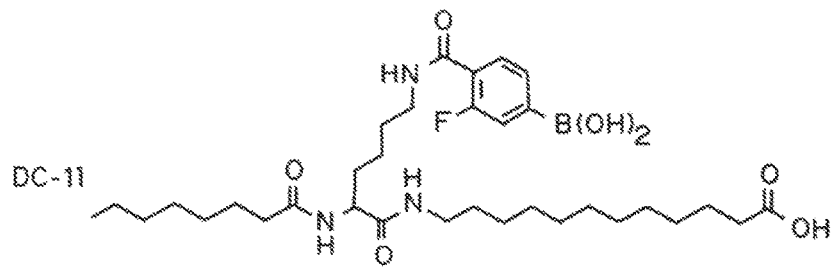
Figure 13C:
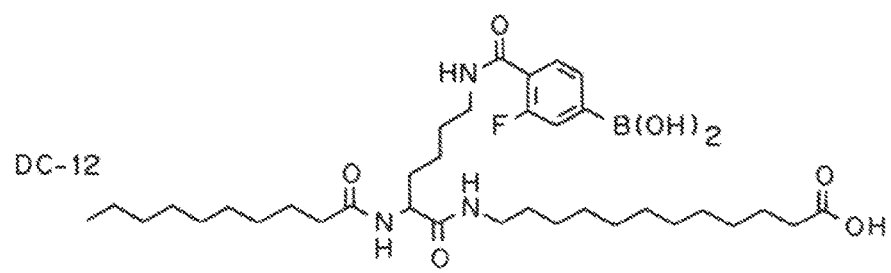
Figure 13C:
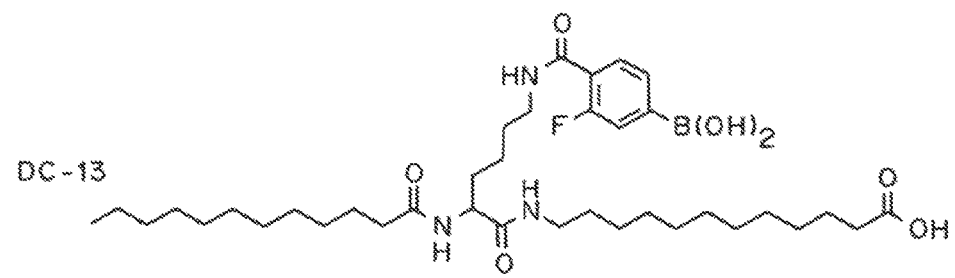
Figure 13C:
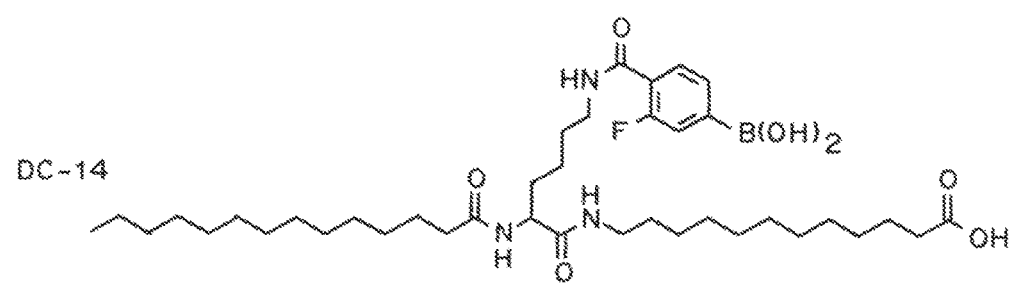
Figure 13C:
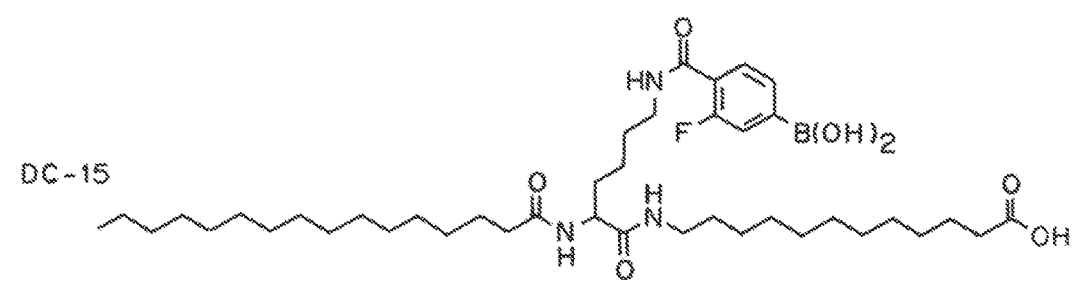
Figure 14:
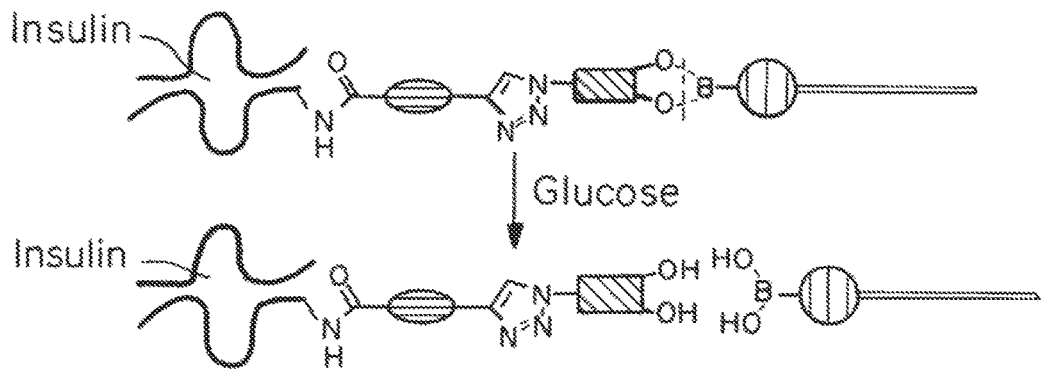
FIG. 14 is a diagram of glucose-responsiveness of an example of derivatized insulin.

In order to explore the activation of these PBA-containing insulin derivatives with a non-glucose diol, the IPGTT was performed using fructose instead of glucose. It is expected that other diols would activate PBA insulins, since PBA is not a glucose-specific binder. For treatment with Ins-PBA-F, glucose challenge resulted in a spike and reversal of blood glucose levels, as previously seen. (FIG. 9a). However, when fructose was instead used to challenge the mice, blood glucose levels were only slightly elevated and quickly returned to baseline for the duration of the study. In contrast, treatment with Ins-LA-C14 demonstrated a gradual rise in blood glucose levels, presumably due to the conversion of administered fructose into glucose (FIG. 9b). When glucose was used to challenge following Ins-LA-C14 treatment, the behavior was similar to that seen in previous studies.

F. Synthetic Methods

Materials:

12-Aminododecanoic acid, [1,1'-Bis(diphenylphosphino) ferrocene]dichloropalladium(II), complex with dichloromethane (Pd(dppf)Cl$_2$DCM), lithium hydroxide, triethylamine, bis(pinacolato)diboron, potassium acetate, 4-carboxyphenylboronic acid, 4-bromosulfonyl chloride, 3-Carboxy-5-nitrophenylboronic acid, dichloromethane, ethyl acetate, methanol, and dioxane were purchased from Sigma Aldrich (St. Louis, Mo., USA). 4-Carboxy-3-fluorophenylboronic acid was purchased from Optima Chemical (Douglas, Ga., USA). O-(Benzotriazol-1-yl)-N,N,N',N'-tetramethyluronium tetrafluoroborate (TBTU) was purchased from AnaSpec (Fremont, Calif., USA).

Compound Characterizations:

1. 12-((4-boronophenyl)sulfonamido) dodecanoic acid 1

Methyl 12-((4-(4,4,5,5-tetramethyl-1,3,2-dioxaborolan-2-yl)phenyl)sulfonamido)dodecanoate 11 (2.71 g, 5.47 mmole) and lithium hydroxide (1.56 g, 65.20 mmole) were dissolved in a 3:1 MeOH/water solution (80 ml). The reaction was stirred overnight under nitrogen and the solvent was removed in vacuo. The reaction was then dissolved in water, acidified to pH 1 using 1 N HCl, and the precipitate collected by filtration. Column chromatography (0-20% MeOH in DCM) gave a white product (1.4 g, 3.56 mmole, 65%).

$^1$H NMR (CD$_3$OD): δ7.84 (d, 2H), δ7.82 (d, 2H), δ3.31 (t, 2H), δ2.84 (t, 2H), δ2.27 (m, 2H), δ1.59 (m, 2H), δ1.26 (14H).

$^{13}$C NMR (CD$_3$OD): δ177.0, 134.5, 126.1, 116.7, 43.3, 34.2, 29.8, 29.7, 29.5, 26.9, 25.4

HRMS: calculated 399.1887; found: 399.1900.

2. 12-(4-boronobenzamido)dodecanoic acid 2

(4-((12-methoxy-12-oxododecyl)carbamoyl)phenyl)boronic acid 8 (4.22 g, 11.20 mmole) and lithium hydroxide (1.35 g, 55.97 mmole) were dissolved in a 3:1 MeOH/water solution (80 ml). The reaction was stirred overnight under nitrogen and the solvent was removed in vacuo. The reaction was then dissolved in water, acidified to pH 1 using 1 N HCl, and the precipitate collected by filtration. Column chromatography (0-20& MeOH in DCM) gave a white product (2.64 g, 7.28 mmole, 65%).

$^1$H NMR (CD$_3$OD) δ7.73 (d, 2H), δ7.67 (d, 2H), δ3.27 (t, 2H), δ2.22 (t, 2H), δ1.56 (m, 4H), δ1.30 (m, 14H).

$^{13}$C NMR (CD$_3$OD) δ177.0, 133.9, 126.5, 100.5, 40.4, 34.2, 29.9, 29.7, 29.5, 27.4, 25.4.

HRMS: calculated 363.2217; found: 399.1900.

3. 12-(4-borono-2-fluorobenzamido) dodecanoic acid 3

(3-fluoro-4-((12-methoxy-12-oxododecyl)carbamoyl) phenyl)boronic acid 9 (5.15 g, 13.04 mmole) and lithium hydroxide (1.56 g, 65.20 mmole) were dissolved in a 3:1 MeOH/water solution (80 ml). The reaction was stirred overnight under nitrogen and the solvent was removed in vacuo. The reaction was then dissolved in water, acidified to pH 1 using 1 N HCl, and the precipitate collected by filtration. Column chromatography (0-20% MeOH in DCM) gave a white product (3.23 g, 8.48 mmole, 65%).

$^1$H NMR (CD$_3$OD) δ7.73 (m, 3H), δ3.35 (t, 2H), δ2.26 (t, 2H), δ1.60 (m, 4H), δ1.31 (m, 14H).

$^{13}$C NMR (CD$_3$OD) δ177.0, 129.7, 127.7, 121.1, 121.0, 40.3, 34.2, 29.9, 29.7, 29.5, 27.3, 25.4.

HRMS: calculated 381.2123; found: 381.2124.

4. 12-(3-borono-5-nitrobenzamido) dodecanoic acid 4

(3-((12-methoxy-12-oxododecyl)carbamoyl)-5-nitrophenyl)boronic acid 10 (1.02 g, 2.43 mmole) and lithium hydroxide (0.29 g, 12.13 mmole) were dissolved in a 3:1 MeOH/water solution (40 ml). The reaction was stirred overnight under nitrogen and the solvent was removed in vacuo. The reaction was then dissolved in water, acidified to pH 1 using 1 N HCl, and the precipitate collected by filtration. Column chromatography (0-20% MeOH in DCM) gave a white product (0.64 g, 1.88 mmole, 65%).

$^1$H NMR (CD$_3$OD) δ8.58 (m, 2H), δ8.45 (s, 1H), δ3.34 (t, 2H), δ2.20 (t, 2H), δ1.54 (m, 4H), δ1.22 (m, 14H).

$^{13}$C NMR (CD$_3$OD) δ177.1, 167.2, 148.5, 138.7, 136.0, 131.0, 123.9, 40.6, 30.0, 29.8, 29.6, 27.4, 25.4.

HRMS: calculated 408.2068; found: 408.2068.

5. Methyl 12-((4-bromophenyl) sulfonamido)dodecanoate 7

Methyl 12-aminododecanoate 6 (5.08 g, 22.19 mmole) and 4-bromosulfonyl chloride (4.73 g, 18.49 mmole) were dissolved in dichloromethane (100 ml) with triethylamine (7.73 ml, 55.47 mmole). The reaction was stirred overnight and the solvent was removed in vacuo. The reaction was then dissolved in ethyl acetate and extracted with water and brine. The organic layer was dried with MgSO$_4$ and evaporated in vacuo. Column chromatography (0-20% MeOH in DCM) gave a white product (6.2 g, 13.84 mmole, 75%).

$^1$H NMR (CD$_3$OD) δ7.73 (d, 2H), δ7.67 (d, 2H), δ3.67 (s, 3H), δ2.96 (t, 2H), δ2.31 (t, 2H), δ1.59 (m, 2H), δ1.48 (m, 2H), δ1.22 (m, 14H)

$^{13}$C NMR (CD$_3$OD) δ175.1, 139.8, 133.0, 129.3, 128.0, 52.1, 43.9, 34.8, 30.1, 29.9, 29.8, 29.7, 27.1, 25.6.

HRMS: calculated 447.1079; found: 447.1094.

6. (4-((12-methoxy-12-oxododecyl)carbamoyl)phenyl)boronic acid 8

Methyl 12-aminododecanoate 6 (2.00 g, 8.73 mmole), 4-carboxyphenylboronic acid (2.18 g, 13.10 mmole), and TBTU (4.21 g, 13.10 mmole), were dissolved in a 1:1 DMF/pyridine solution (100 ml). The reaction was stirred overnight under nitrogen and the solvent was removed in vacuo. The reaction was dissolved in ethyl acetate and extracted with 30% citric acid and brine. The organic layer was dried with MgSO$_4$ and evaporated in vacuo. Column chromatography (0-20% MeOH in DCM) gave a white product (2.84 g, 7.53 mmole, 85%).

$^1$H NMR (CD$_3$OD) δ7.77 (d, 2H), δ7.71 (d, 2H), δ3.62 (s, 3H), δ3.27 (t, 2H), δ2.27 (t, 2H), δ1.55 (m, 4H), δ1.25 (m, 14H).

$^{13}$C NMR (CD$_3$OD) δ175.3, 168.2, 134.1, 128.7, 126.5, 110.7, 51.3, 40.4, 38.2, 36.3, 34.1, 31.2, 29.7, 27.4, 20.1.

HRMS: calculated 377.2374; found: 377.2378.

7. (3-fluoro-4-((12-methoxy-12-oxododecyl)carbamoyl)phenyl) boronic acid 9

Methyl 12-aminododecanoate 6 (2.00 g, 8.73 mmole), 4-Carboxy-3-fluorophenylboronic acid (2.41 g, 13.10 mmole), and TBTU (4.21 g, 13.10 mmole), were dissolved in a 1:1 DMF/pyridine solution (100 ml). The reaction was stirred overnight under nitrogen and the solvent was removed in vacuo. The reaction was dissolved in ethyl acetate and extracted with 30% citric acid and brine. The organic layer was dried with MgSO$_4$ and evaporated in vacuo. Column chromatography (0-20% MeOH in DCM) gave a white product (2.98 g, 7.53 mmole, 85%).

$^1$H NMR (CD$_3$OD) δ7.65 (m, 3H), δ3.64 (s, 3H), δ3.35 (t, 2H), δ2.30 (t, 2H), δ1.59 (m, 4H), δ1.30 (m, 14H).

$^{13}$C NMR (CD$_3$OD) δ175.3, 166.1, 161.1, 159.1, 129.8, 121.3, 121.1, 51.3, 40.3, 34.1, 30.0, 29.7, 29.5, 27.3, 25.3.

HRMS: calculated 395.2279; found: 395.2293.

8. (3-((12-methoxy-12-oxododecyl)carbamoyl)-5-nitrophenyl) boronic acid 10

Methyl 12-aminododecanoate 6 (2.00 g, 8.73 mmole), 3-Carboxy-5-nitrophenylboronic acid (2.78 g, 13.10 mmole), and TBTU (4.21 g, 13.10 mmole), were dissolved in a 1:1 DMF/pyridine solution (100 ml). The reaction was stirred overnight under nitrogen and the solvent was removed in vacuo. The reaction was dissolved in ethyl acetate and extracted with 30% citric acid and brine. The organic layer was dried with MgSO$_4$ and evaporated in vacuo. Column chromatography (0-20% MeOH in DCM) gave a pale yellow product (3.18 g, 7.53 mmole, 85%).

$^1$H NMR (CD$_3$OD) δ8.60 (m, 2H), δ8.45 (s, 1H), δ3.59 (s, 3H), δ3.35 (t, 2H), δ2.23 (t, 2H), δ1.55 (m, 4H), δ1.23 (m, 14H).

$^{13}$C NMR (CD$_3$OD) δ175.3, 167.1, 148.5, 138.6, 136.0, 130.9, 123.7, 51.3, 40.6, 34.1, 29.9, 29.7, 29.5, 27.4, 25.3.

HRMS: calculated 422.2224; found: 422.2223.

9. Methyl 12-((4-(4,4,5,5-tetramethyl-1,3,2-dioxaborolan-2-yl)phenyl)sulfonamido)dodecanoate 11

Methyl 12-((4-bromophenyl)sulfonamido)dodecanoate 7 (2.96 g, 6.61 mmole), bis(pinacolato)diboron (2.52 g, 9.91 mmole), Pd(dppf)Cl$_2$DCM (0.81 g, 0.9 mmole), and potassium acetate (2.60 g, 26.43 mmole) were dissolved in dioxane (100 ml) and refluxed under nitrogen overnight. The reaction was filtered through Celite and the solvent removed in vacuo. The reaction was dissolved in ethyl acetate and extracted with water and brine. The organic layer was dried with MgSO$_4$ and evaporated in vacuo. Column chromatography (0-20% MeOH in DCM) gave a white product (2.71 g, 5.47 mmole, 85%).

$^1$H NMR (CD$_3$OD) δ7.90 (d, 2H), δ7.84 (d, 2H), δ3.65 (s, 3H), δ2.84 (t, 2H), δ2.31 (t, 2H), δ1.58 (m, 2H), δ1.43 (m, 2H), δ1.36 (12H), δ1.22 (m, 14H) $^{13}$C NMR (CD$_3$OD) δ175.3, 143.8, 135.5, 126.4, 85.0, 51.3, 43.3, 34.1, 29.9, 29.8, 29.7, 29.5, 26.9, 25.3, 24.5.

HRMS: calculated 495.2826; found: 495.2853.

Example 2

Synthesis and Testing of Glutamate-Derivatized Insulin

This example relates to combinatorial generation of a library of chemically modified human insulins for glucose responsive delivery. A library of chemically modified, human insulins will be developed, with bioavailability that is dependent on local glucose concentration. Specifically:

Synthesis of a library of approximately 700 chemically modified insulin analogs that have diverse chemical groups on the B29 lysine position to insert glucose-responsive properties.

Modified insulin analogs will be assayed for glucose-responsive aggregation in physiological pH using size-exclusive chromatography (SEC).

Lead glucose-responsive modified insulin analogs will be scaled up evaluated for ability to bind to insulin receptor and activate the insulin signaling pathway.

Formulations of modified insulin analogs as aggregated particles will be generated to determine glucose-responsive insulin release in varying glucose levels in vitro. This study tests the insulin-releasing profile as a function of time and glucose concentrations.

Leads will be tested for glucose correction in diabetic mouse models. Responsiveness will be evaluated by monitoring insulin levels in response to glucose challenge. Promising candidates will be evaluated in additional models with Sanofi help for both safety and efficacy.

This example also relates to non-covalent insulin-binding peptides for glucose-dependent activity will be developed to facilitate a glucose trigger for insulin activity and/or solubility of insulin. Specifically:

Develop and synthesize a combinatorial library of 100 million oligopeptides which incorporate amino acids with glucose-responsive moieties.

Establish rapid screening of this library for insulin-binding affinity and glucose-responsiveness.

Leverage high throughput mass spectrometry proteomics for sequencing and identification of peptide hits.

Evaluate the effect of positive hits on insulin activity by a cell-based assay, and validate that this is dependent upon glucose concentration.

Explore formulations of positive peptide hits with insulin.

Probe the therapeutic efficacy of promising leads by glucose correction in diabetic mouse models, examining responsiveness by monitoring insulin levels in response to glucose challenge. Promising candidates will be evaluated in additional models for both safety and efficacy, with partnership from Sanofi.

A. Background and Significance

While a daily regimen consisting of blood glucose monitoring and regular insulin injections before meals is sufficient to manage diabetes in most patients, this traditional standard of care is sometimes inadequate, and can lead to acute complications such as coma, and over time even kidney failure and blindness. To better address changes in blood glucose, a combination of long and short insulin analogues have been developed. However, these methods are not inherently sensitive to glucose, and depend on external glucose sensors, leading to poorly regulated normoglycemia. Attempts have been made to develop glucose-responsive carrier materials that can encapsulate insulin and make it bioavailable on demand, but these methods traditionally require a high ratio of polymeric carrier relative to the amount of insulin delivered, raising concerns for its usage in regular injections.

As an alternative to glucose-responsive materials, we propose novel peptides that bind to and inhibit insulin in a glucose-dependent manner. This allows insulin activity to be responsive to changes in blood glucose concentrations, while the insulin-peptide complex is still composed predominately of the drug insulin. The addition of an inherent glucose sensing capacity to the peptide binder facilitates the development of formulations with glucose sensing capabilities using FDA approved forms of insulin. Here we propose to develop and screen a library of oligopeptides for glucose-responsive binders of insulin, with the goal to design a formulated insulin that can maintain active glycemic control for at least 12 hours.

B. Research Design and Methods

1. Combinatorial Generation of a Library of Modified Insulin Analogs for Glucose Responsive Delivery Synthesis of Approximately 700 Modified Insulin Analogs A series of modified insulin with potential glucose-responsive effects will be synthesized using the chemical ligation method developed in the Anderson group. We currently use either click chemistry or direct amide linkage to modify insulin in B29 lysine position, which preserves the cellular activity of the hormone. The appended chemical groups are designed to systematically cover a wide range of functionalities that vary hydrophobicity/hydrophilicity, charge, and glucose binding (for example, diol and phenylboronic acid) moieties. Some representative structures are demonstrated in FIGS. 1 and 2. The pilot batch of 700 modified insulin analogs will be synthesized in 5 mg scale for an initial screen of glucose responsiveness.

The derivatization sstructures can be $-CO-(CH_2)_j-NH-CO-CR_1R_2$, where j is an integer from 3-25, where $R_1$ is $-NH-R_{12}$ or $-NH-CO-CH_2-CH_2-CNR_{12}-R_{32}$, where $R_{32}$ is glucamine, gluconic acid, glucosamine, fructosamine, galactosamine, mannosamine, or other hexosamines; $R_{12}$ is selected from the group consisting of hydrogen, $-SO_2$alkyl, $-SO_2$cycloalkyl, $-SO_2$heterocycloalkyl, $-SO_2$aryl, $-SO_2$heteroaryl, $-CO$alkyl, $-CO$cycloalkyl, $-CO$heterocycloalkyl, $-CO$aryl, $-CO$heteroaryl, $-CONH$alkyl, $-CONH$cycloalkyl, $-CONH$heterocycloalkyl, $-CONH$aryl, $-CONH$heteroaryl, where alkyl, cycloalkyl, heterocycloalkyl, aryl, and heteroaryl groups are substituted or unsubstituted; $R_2$ is $-(CH_2)_n-R_{11}$, where n is an integer from 3-25; and $R_{11}$ is a phenylboronic acid group. In some embodiments, n is 4. In some embodiments, $R_{12}$ is a sulfonyl chloride, isocyanate, carboxylic acid chloride, aldehyde, or hydrogen. Examples of structures are shown in FIG. 23.

Glucose-Responsive Aggregation in Physiological pH Using Size-Exclusion Chromatography (SEC) to Screen for Glucose-Responsive Analogs All synthesized modified insulin analogs will be first formulated with zinc(II), phenol, m-cresol and sodium chloride to induce aggregation. SEC will be used to measure the molecular weight of the insulin aggregate in the presence and absence of glucose in the mobile phase. Analogs with decreasing MW in the presence of glucose will be selected for scale-up synthesis and further characterizations.

Insulin Receptor Binding Affinity and Activation of the Insulin Signaling Pathway Selected insulin analogs will be tested for their affinities to insulin receptor compared to native insulin. An insulin activity assay will be performed to evaluate the ability of modified insulin to activate the insulin signaling pathway by measuring the level of phosphorylated Akt.

Formulation of Modified Insulin Analogs In Vitro Glucose-Responsive Insulin Release Several formulation methods will be explored. Cholesterol will be included in the formulation to increase the stability of aggregated particles and both natural and synthesized lipids will also be tested to optimize the formulation. Dynamic light scattering (DLS) methods will be used to measure the size and molecular weight of the aggregation. Aggregated particles will be dialyzed in PBS with different glucose concentrations (0, 5, 10, 20 and 30 mM) at 37° C. The released insulin monomers will be quantified at different points using HPLC with native insulin as an internal standard.

In Vivo Test of Lead Modified Insulin Analogs in Diabetic Mice Models

C57BL/6J mice were injected with streptozocin (STZ) to induce diabetes. Diabetic mice will be given subcutaneous injections of formulated insulin analogs. Initial studies will examine blood glucose every 30 minutes after injection until 8 hours. For long-term effect studies, blood glucose will be monitored 4 times a day for 2 weeks. More advanced safety and efficacy evaluation will be performed in collaboration with Sanofi.

2. Non-Covalent Insulin-Binding Peptides for Glucose Responsive Delivery

Combinatorial Synthesis of a Library of 100 Million Short Peptides that Incorporate Glucose-Responsive Moieties We propose to use manual solid-phase peptide synthesis to generate a large combinatorial library of short peptides. Using expertise in the Anderson lab, we will generate this library from a subset of amino acids that afford R group chemistry, as well as chemically modified amino acids that contain glucose-binding moieties such as phenylboronic acid. The choice of a peptide library enables *facile* synthesis of a large number of compounds and enables subsequent hit identification through mass spectrometric analyses.

Immobilized insulin will be exposed to the complete peptide library, with subsequent detergent washes to elute non-binding or weakly binding compounds. Subsequently, elution will be performed using varying concentrations of glucose, and the eluent will be collected to select for peptides with glucose-responsive insulin binding. This method allows rapid screening of a huge library on a manageable scale and will ideally produce a subset of hits that are insulin-binding peptides that lose affinity in the presence of glucose.

Sceening of Peptide Library for Insulin-Binding and Glucose-Responsiveness

Insulin-binding peptides for facilitating glucose-dependent insulin activity and/or solubility are also provided. A combinatorial library of peptides which incorporate amino acids with glucose-responsive moieties, such as phenylboronic acid groups can be used to identify peptides that bind insulin and that, through that binding, affect activity and/or solubility of the insulin. Such effects of identified peptides can be used to alter bioavailability of insulin based on glucose concentration. Screening of the peptides can be accomplished by, for example, exposing immobilized insulin to the complete peptide library and washing with detergent to elute non-binding or weakly binding compounds. Finally, the immobilized insulin can be washed with varying concentrations of glucose and the eluted peptides collected as peptides with glucose-responsive insulin binding. This method allows rapid screening of a huge library on a manageable scale and will produce a subset of hits that are insulin binding.

High Throughput Mass Spectrometry Proteomics for Identification of Peptide Hits

The eluent containing the presumed insulin-binding sequences will be identified using mass spectrometry (MS) techniques. As it is assumed that the sample will be complex, peptides will be separated by a reversed-phase HPLC column in-line with the MS, and tandem MS/MS will be used to determine the peptide sequence. In order to improve the certainty of identification of hits, the eluent will be split into several fractions for independent sampling, and the same library will be screened 10 times by the protocol in 2, and hits will be ranked by the number of times that they appear in each of these screens.

Determining Insulin Signaling Activity and Glucose-Dependence Using in Vitro Cell Culture The resultant peptide hits from MS screening will be resynthesized by solid phase techniques. These peptides hits will be separately incubated with insulin, and this insulin complex will be subsequently tested for insulin receptor activation when compared to native insulin in a cell-based assay. The envisioned assay will measure the level of phosphorylated Akt, a signaling intermediate downstream of the activated insulin receptor. In addition, insulin activity will be monitored in the presence of the peptide hit and hyperglycemic levels of glucose. This will validate whether suppression of insulin activity by the hit peptides is glucose-responsive.

Explore Modified Formulations and Delivery of Peptide/Insulin Target Compounds

The formulation of delivery of insulin with peptide hits will be examined to determine whether a more efficient glucose-responsive trigger can be generated. Using protein engineering, we can explore tethering the peptide to insulin using a flexible linker to improve the binding and responsiveness of the compound. In addition, multivalent peptide structures can be explored to evaluate whether the formation of higher order insulin-peptide aggregates could be used to improve the delivery and the potency of the therapy. The insulin-peptide complexes will also be formulated with existing drug delivery platforms, for example polymeric nanoparticles, to optimize drug delivery kinetics and protect both the insulin and peptide from enzymatic degradation.

Promising Leads Will be Tested for Glucose Correction in Diabetic Mouse Models

The insulin/peptide formulation will be injected subcutaneously or intravenously into streptazotocin-induced diabetic mice. The blood glucose of these mice will be monitored to determine the efficacy and duration of glycemic correction, including probing the insulin-responsiveness by bolus glucose challenge of reversed mice, and monitoring for the appropriate dose to ensure long-term normoglycemia. For short-term effect studies, blood glucose will be monitored every 30 minutes after injection until 8 hours. For long-term effect studies, blood glucose will be monitored 4 times a day for 2 weeks. Promising candidates will be evaluated in additional models with help from Sanofi for both safety and efficacy.

Example 3

Synthesis and Testing of Insulin Derivatives Complexed with Hydrophobic Phenylboronic Acid Groups Insulins with both long acting and glucose responsive properties were engineered in order to achieve improved glycemic control for diabetics.

Extended insulin release was achieved through conjugation of the protein to hydrophobic groups, which can ultimately be cleaved in response to glucose concentration. The desired insulin analogs were synthesized via a three-step reaction sequence. First, native insulin was selectively modified with a clickable alkyne moiety at the B29 residue. A diol was then linked to the insulin via copper-free click chemistry. Finally, the diol group reacted with a phenylboronic acid via formation of a dynamic boronate ester. The specific structures of the alkyne, the diol, and the boronic acid were thoroughly investigated to determine efficient analog synthesis, proper binding affinity between the diol and the boronic acid, the modified compound's responsiveness to glucose, and that the bioactivity of the insulin was preserved. The modified insulin analogs were purified with a variety of physical methods and characterized in vivo. To circumvent problematic low solubility of the analogs caused by the conjugation of hydrophobic groups, zinc was used to formulate fully injectable suspensions in phosphate buffer saline. This study demonstrated the feasibility of generating long acting glucose responsive insulins under physiological conditions.

Despite decades of insulin studies for the treatment of diabetes mellitus, diabetic patients must still adhere to daily insulin injections to manage hyperglycemia. This management is less than ideal for these patients because present, blood glucose levels must be manually tested using an external glucose sensor [Zucchini et al., *Diabetes Technol. Ther.* 2011, 13, 1187-1193], resulting in insufficient patient compliance [Cramer and Pugh, *Diabetes Care* 2005, 28, 78-83]. In addition, misregulation of plasma glucose often results in complications, including heart diseases, hypertension, kidney failure, blindness, and coma, in the case of severe hypoglycemia [Chu et al., *Lab Chip* 2012, 12, 2533-2539]. Accordingly, an injectable, self-regulating insulin release formulation is highly desirable for these patients. However, this technology has yet to truly materialize.

Previous attempts to develop glucose-responsive systems predominantly relied on polymeric carriers, using three major mechanisms to induce insulin release [Chu et al., *Lab Chip* 2012, 12, 2533-2539, Matsumoto et al., *Biomacromolecules* 2004, 5, 1038-1045, Wu et al., *J. Pharm. Sci.* 2011, 100, 2278-2286, Lapeyre et al., *Colloid Interface Sci.* 2008, 327, 316-323, Hong et al., *Colloid Polym. Sci.* 2009, 287, 1207-1214, Huang et al., *Pharm. Res.* 2008, 25, 1150-1157, Kawamura et al., *Colloids Surf B Biointerfaces* 2011, Tang et al., *Biotechnol. Bioeng.* 2003, 82, 47-53]. The interaction of a phenylboronic acid (PBA) with a diol was widely used in hydrogel formulations. In these systems, polymers were modified with PBA or polymerized with PBA moieties, which were then loaded with insulin. The diffusion rate of the insulin varied based on reversible gel swelling, which is governed by glucose concentration [Matsumoto et al., *Biomacromolecules* 2004, 5, 1038-1045, Wu et al., *J. Pharm. Sci.* 2011, 100, 2278-2286, Lapeyre et al., *Colloid Interface Sci.* 2008, 327, 316-323]. Alternatively, glucose oxidase (GO) and insulin were co-encapsulated within pH sensitive hydrogels [Chu et al., *Lab Chip* 2012, 12, 2533-2539, Hong et al., *Colloid Polym. Sci.* 2009, 287, 1207-1214, Huang et al., *Pharm. Res.* 2008, 25, 1150-1157]. The resulting release rate of insulin was thus enhanced at high glucose levels, due to fact that enzymatic oxidation of glucose into gluconic acid causes local acidification followed by matrix swelling. Finally, the competitive interaction between Concanavalin-A (Con-A), a protein with multiple binding sites for glucose, and diols/polysaccharides was harnessed to prepare dynamic, high molecular weight complexes [Kawamura et al., *Colloids Surf B Biointerfaces* 2011, Tang et al., *Biotechnol. Bioeng.* 2003, 82, 47-53]. These complexes disintegrate when glucose concentration increases, allowing insulin to be released. The glucose-regulated insulin formulation (Smartinsulin) with Con-A and dextran demonstrated the potential of this technology [Zion, Ph. D. Thesis, Massachusetts Institute of Technology, 2004]. However, in all the systems mentioned above, protein payloads were usually less than 10% w/v within the formulation. As a result, large amounts of non-therapeutic carrier materials could quickly accumulate within the body after repeated injections, leading to severe immunological consequences. Thus using degradable polymers to create the systems mentioned above is highly sought after and currently being investigated [Mukerjee and Pruthi, *Biomed. Nanotechnol.* 2007, 3, 68-74, Elsayed et al., *AAPS PharmSciTech* 2011, 12, 958-964, Damge et al., *Expert Opin. Drug Delivery* 2008, 5, 45-68, Huynh et al., *Biomaterials* 2008, 29, 2527-2534]. Nonetheless, a mismatch between the rate of polymer degradation and insulin release might result in the similar build up of harmful waste products.

Native insulin is not suitable for direct injection because of the 30 minute delay time for action (due to self-association) and overall short lasting effect [Berman, *Diabetes Care* 1980, 3, 266-269]. Accordingly, both long and short acting insulins have been developed to treat diabetic patients, whom need both types to maintain glycemic control [Esposito and Giugliano, *Expert Opin. Biol. Ther.* 2012, 12, 209-221]. The short acting form is injected just before a meal, and the long acting form is administrated twice per day to maintain a basal concentration of insulin. Short-acting analogs are made via chemical modifications or by genetically modifying the insulin amino acid sequence (Lipsro, Aspart). These modifications reduce the hexamerization to ensure instantaneous bioavailability [Siddiqui, *Mymensingh Med J* 2007, 16, 117-121, Helms and Kelley, *Ann. Pharmacother.* 2009, 43, 658-668]. Long acting formulations were prepared by mixing the native insulin with protamine (NPH) or with a large molar excess of zinc (Lente) [Gerich, *Am. J. Med.* 2002, 113, 308-316]. However, these formulations lack sufficient homogeneity, which is manifested by inconsistent bioactivity profiles. Other long acting analogs have also been prepared by chemical conjugation with either polyethylene glycol (PEG) [Hinds et al., *Bioconjugate Chem.* 2000, 11, 195-201, Shechter et al., *Eur. J. Pharm. Biopharm.* 2008, 70, 19-28], fatty acids [Szypowska et al., *Pol. Arch. Med. Wewn.* 2011, 121, 237-246], (detimer) or bile acids[Lee et al., *Bioconjugate Chem.* 2005, 16, 615-620]. These grafted compounds increase the in vivo circulation time of insulin due to serum albumin interactions, as well as increasing hydrodynamic volume. Additional studies where insulin was conjugated to albumin or polysaccharides, showed to also increase in vivo circulation time [Shechter et al., *Bioconjugate Chem.* 2005, 16, 913-920, Baudys et al., *Bioconjugate Chem.* 1998, 9, 176-183].

Recent publications demonstrated that insulin analogs modified with hydrophobic groups, such as bile acids, fatty acids [Jonassen et al., *Pharm. Res.* 2006, 23, 49-55] and fluorinated carbons [Jonassen et al., *Pharm. Res.* 2006, 23, 49-55] create reversible, high molecular weight structures generated by the intermolecular hydrophobic interactions. Radioactive zinc was formulated with the bile-modified insulin then injected in vivo. It was shown that the system had a half-life of 24 hours, while zinc alone has a half-life of 4 hours. This data suggests that the long lasting activity of the modified insulin is due to not only to the modified insulin's increased adhesion to serum albumin but also to the hydrophobic interactions between the bile acids.

Two types of other insulins also have also been developed to demonstrate long acting properties. Glargine, an insulin with an increased isoelectric point (IP 6.7), was injected as an acidic, soluble solution that created an amorphous precipitate at the injection site [Gerich, *Curr. Med. Res. Opin.* 2004, 20, 31-37]. Zinc-stapled insulin, made via recombinant methods, has an increased number of zinc binding sites causing enhanced self-association properties [Phillips et al., *J. Biol. Chem.* 2010, 285, 11755-11759]. Both the glargine and zinc-stapled insulin analogs were shown to diffuse slowly from the subcutaneous injection site.

The objective of this work is to develop novel insulin formulations which have both long acting and glucose responsive properties without the use of a polymeric medium. In this approach, click chemistry was utilized and optimized for the chemical modification of native insulin. First alkyne moieties were selectively conjugated onto the B29 lysine residue, which generated clickable insulin. The alkyne group enabled efficient functionalization of the insulin with various azido-substituted diols. Subsequently, a specifically designed azido substituted peptide featuring various dopamine groups was conjugated to the insulin. The dopamine functional groups were then linked to hydrophobic phenylboronic acid derivatives via the formation of boronate ester. The hydrophobic insulin formulations were studied to determine both the long acting properties and glucose responsiveness at physiological conditions through the reversible formation of the boronate ester. The interaction between various diols and phenylboronic acids were studied with $^{11}$B NMR, and the modified insulin analogs and their formulations were extensively investigated for their bioactivities, and capabilities of complexing with selected boronic acids in order to generate a realistic model. Further optimization of the system is needed to achieve further implementation of these formulations.

2. Materials and Methods 2.1. Materials

Propargyl dPEG NHS ester was purchased from Quanta Biodesign; DBCO NHS ester was purchased from Click Chemistry Tools. 8-Azidoadenosine, 2,5-dioxopyrrolidin-1-yl tetradecanoate N-succinimidyl myristate was from Santa Cruz biotechnology. Recombinant human insulin was purchased from Life Technologies Corporation. 4-(N-cyclohexyl-N-(4-methoxybenzyl)sulfamoyl)phenylboronic acid (4NBA) was from Combi blocks. 6-Azido-6-deoxy-d-galactose was purchased from CarboSynth Ltd. All organic solvents and other chemicals were purchased from Sigma Aldrich (US).

2.2. Synthesis of Alkyne Modified Insulin (Al-Insulin) with Propargyl dPEG NHS Ester Native insulin (100 mg, 17.2 mol) was dissolved in a solution (12 mL) of DMSO and triethylamine (95:5 v/v). A solution of propargyl dPEG NHS ester (17.2 umol, 3.87 mg from 100 mg/mL in DMSO) was added to the above dissolved insulin at room temperature. After 30 min, the reaction was quenched with 40 mL of water and 5 mL of 1M HCl. The reaction mixture was dialyzed with a MWCO 3500 Da membrane against phosphate buffered saline (PBS) at 4° C. for 24 hours and then lyophilized. The conjugate was purified using a 1260 Infinity HPLC system (Agilent Technologies). This system consisted of 2 1260 prep pumps, a 1260 prep ALS, a 1260 DAD DL UV light detector, and a 1260 FCPS fraction collector. Samples were run on a preparative C-18 column (Atlantis, Waters 250 mm×25 mm) using acetonitrile (with 1.5% acetic acid)/DDW; gradient was applied from 5:95 to 40:60; wavelength: 220 nm. Pure insulin samples were lyophilized and characterized via LC/MS Waters system; Acquity LC equipped with a QTof MS purchased together from Waters. HPLC grade water and 0.01% formic acid in acetonitrile (Fischer Scientific) were used in a gradient over 3 minutes from 95:5 water/acetonitrile to 5:95 respectively. The flow rate was 0.6 mL/min through an Acquity UPLC BEH C18 1.7 μL, 2.1×50 mm column thermo regulated at 60° C. The sample manager (thermo regulated at 4° C.), UV-PDA detector, and binary flow manager were also part of the LC-MS, and were Acquity purchased from Waters. The software that analyzed data was MassLynx V4.1 from Waters. MaxEnt 1 was used to calculate the average molecular weight of samples in a range from 100-2000 Daltons. Typical yield was about 50%. LC-MS-TOF m/z $[M+H]^+$ 5916.00, $[M+5H]^{5+}$ 1183.20 and $[M+4H]^{4+}$ 1479.23.

2.3. Synthesis of Alkyne Modified Insulin Using DBCO NHS Ester (DBCO-Insulin)

100 mg of human insulin (17.2 umol) was dissolved in a 12 mL solution of anhydrous DMSO and TEA 95:5 v/v. The ester was dissolved in to a concentration of 1 mg/10 uL DMSO. A volume containing 1 eq. (17.2 umol) of the ester was added to the insulin solution. The reaction was carried out for 180 minutes at room temperature. The reaction was quenched with 40 mL of DDW followed by 5 mL of 1M HCl. The crude reaction was dialyzed against PBS at 4° C. for 24 hours and then lyophilized. The conjugate was purified with HPLC and analyzed via LC/MS as depicted above. LCMS showed m/z $[M+H]^+$ 6180, $[M+5H]^{5+}$ 1236.66, $[M+4H]^{4+}$ 1545.61.

2.4. Synthesis of Insulin Analogs Via Click Chemistry 15 mg of Al-insulin was dissolved in an 8 mL mixture of DMSO:PBS 2:1 v/v. 79.5 mg (150 umol) of tris[(1-bdenzyl-1H-1,2,3-triazol-4-yl)methyl]amine (TBTA) was dissolved in 1.5 mL of DMSO. 10 mg of $CuSO_4$ (40 umole) was dissolved in 1.75 mL DDW. 166.5 mg (1506 umole) of aminoguanidine hydrochloride was dissolved in 0.93 ml of DDW. The reaction was carried out using an excess of over 100 eq. azido-terminated compounds dissolved in 0.6 mL of DDW. 60 mg of (+)-sodium L-ascorbate (300 umole) was dissolved in 0.375 mL of DDW. The various solutions were added to the insulin solution in the following order: (1) 1.2 mL of the TBTA solution was pre-complexed with 0.6 mL of the $CuSO_4$ solution; the complex was then added (2) The aminoguanidine hydrochloride solution. (3) A diol compound containing solution (4) (+)-sodium L-ascorbate solution. The reaction was stirred at room temperature for 2 hours then dialyzed against PBS at 4° C. for 24 hours. Further purification was carried out using HPLC and analysis was done via LC/MS, as depicted above. 6G-Al-insulin, m/z $[M+H]^+$ 6121.00, $[M+5H]^{5+}$ 1225.31, $[M+4H]^{4+}$ 1479.89. DP1-Al-insulin, m/z $[M+H]^+$ 6294.0, $[M+5H]^{5+}$ 1259.9, $[M+4H]^{4+}$ 1574.4. DP3-Al-insulin, m/z $[M+H]^+$ 6882.0, $[M+5H]^{5+}$ 1377.13, $[M+4H]^{4+}$ 1721.2.

The second approach to modify insulin with azido diols utilized dibenzocyclooctyne (DBCO) copper-free chemistry. 1.5 mg/ml of the hormone was suspended in PBS along with 3 eq of various azido compounds; the reaction was carried out for 24 hour at 4° C. The crude product was purified via dialysis against DDW and samples were evaluated using LC-MS. 6G-DBCO-insulin, m/z $[M+H]^+$ 6383.0, $[M+5H]^{5+}$ 1277.43, $[M+4H]^{4+}$ 1596.57. DP1-DBCO-insulin: $[M+H]^+$ 6559.0, $[M+5H]^{5+}$ 1311.8, $[M+4H]^{4+}$ 1639.7. DP3-DBCO-insulin: $[M+H]^+$ 6144.0, $[M+5H]^{5+}$ 1428.8 and $[M+4H]^{4+}$ 1786.2.

2.5. Insulin Digestion with Trypsin

Digestion of the insulin sample with trypsin was carried out at 37° C. for 2 hours and at room temperature overnight (supporting information). The latter method is generally preferred as it results in considerably less autolysis of the trypsin. However, insulin is resistant to proteolysis and only the digestion at 37° C. yielded sufficient proteolytic fragments. These were analyzed using with a Tempo nanoflow HPLC and a QSTAR Elite Quadrupole-time-of-flight mass spectrometer. Peptide separation was carried out on a reversed phase C18 capillary column at a flow rate of 300 nL/min. Mass spectral data were analyzed with the assistance of the BioAnalyst software which is part of the QSTAR Elite data system. Assignments were made based on measured molecular weights as well as the respective fragment ion mass spectra when available (supporting information). This analysis was carried out at The Koch Institute Proteomics Core Facility at Massachusetts Institute of Technology (MIT).

2.6. Synthesis of C12-Nitro-PBA 3-carboxy-5-nitrophenylboronic acid (1.27 g, 6.03 mmole) and TBTU (1.94 g, 6.03 mmole) were dissolved in 40 mL DMF/pyridine (1:1) in a 200 mL round-bottom flask at 0° C. A solution of dodecyl amine (4.16 mL, 18.08 mmole) was in 20 mL DMF was then added to the reaction. The reaction was stirred in ice bath for 30 min. It was then stirred at room temperature overnight. DMF and pyridine were removed in vacuum. 100 mL EtOAc was added to dissolve the crude product. The organic layer was then extracted with 50 mL 30% citric acid twice and brine. The organic collection was dried and concentrated. A column chromatography (DCM/MeOH=10/1) was used for purification to give the final product (1.2 g, 53%) as white powder. $^1H$ NMR (400.13 MHz, DMSO-$d_6$, ppm): δ 0.84 (t, 3H, $CH_3$, J=6.4 Hz), 1.20-1.29 (m, 18H, $(CH_2)_9$), 1.52-1.55 (m, 2H, $CH_2$), 3.17 (s, 2H, $(OH)_2$), 2.25-3.30 (m, 2H, $CH_2$), 8.61-8.74 (m, 3H, PhH), 8.82 (m, 1H, NH).

2.7. Synthesis of C12-Insulin Analogs 100 mg of insulin (17.2 mol) was dissolved in a 12 mL solution of anhydrous DMSO and TEA (95:5 v/v). One molar equivalent of 5-dioxopyrrolidin-1-yl tetradecanoate was dissolved in 1 mL of DMSO:DCM 80:20 v:v and was added to the dissolved insulin. The reaction was carried out for 180 minutes at room temperature. The reaction was quenched with 40 mL of DDW followed by 5 mL of 1M HCl. The crude reaction was dialyzed in a 3500 Da cassette against Phosphate buffered saline (PBS) at 4° C. for 24 hours and then lyophilized. The conjugate was purified using HPLC and analyzed via LC/MS and the typical yield was about 50%. C12-DBCO-Insulin: m/z $[M+H]^+$ 6019.0, $[M+6H]^{6+}$ 1038.9, $[M+5H]^{5+}$ 1204.8, $[M+4H]^{4+}$ 1505.1.

2.8. Synthesis of Dopamine Containing Peptides Terminated with Azido Pentanoic Acid DP1-peptide (azido-pentanoic-DOPA-GLY-$NH_2$) and DP3 peptide (azido-pentanoic-DOPA-GLY-DOPA-GLY-DOPA-GLY-$NH_2$) were synthesized using Fmoc protected amino acids Fmoc-3,4-dihydroxy-phenylalanine, acetonitrile protected. Azido pentanoic acid was finally conjugated to the N-terminal in a procedure. The correct molecular weight was determined by MALDI-TOF mass spectrometry (ABI model Voyager DESTR using sinapinic acid or alpha cyano-4-hydroxycinnamic acid as matrix) and purity was determined by analytical HPLC (Agilent model 1100). MALDI-TOF of DP1-peptide, m/z 309.32, 756.92 (dimer). MALDI-TOF of DP3-peptide, m/z 963.22. Azido peptides were prepared at the Biopolymer Facility, located within the Koch Institute for Integrative Cancer Research at MIT.

2.9. Preparation of DP3-Insulin and Hydrophobic PBA Solid Complexes (Direct Method)

Direct complexation of DP3-Insulin was carried out at an aqueous/organic 2/1 v/v solution in order to enable co-solubility with hydrophobic phenylboronic acids. Equal molar quantities of 4NBA and DP3-Insulin (0.5 mM) were dissolved in 2:1 acetonitrile:PBS and then the pH was modified to 7.5 or 8.5 by adding calculated amount of concentrated NaOH solution. The obtained complex was immediately frozen in liquid nitrogen and then freeze dried to generate a white solid. Similarly, selected diols (glucose, fructose, 4EC, 2HA, Azido-6-glactose, DP1-peptide and DP3-peptide) were formulated via the direct method. In order to validate formation of a complex 4NBA-diols, 1TBA-solids obtained by the direct method, as well as, their organic/aqueous solutions (prior to freeze drying) were analyzed with $^{11}$B NMR and via FTIR.

2.10. Preparation of DP3-Insulin and C12-Nitro-PBA Complexes in Phosphate Buffer Saline DP3-insulin (0.026 mM) was formulated with an aliphatic modified phenylboronic acid (C12-Nitro-PBA, 0.13 mM) in aqueous solution in the presence of 3 $Zn^{2+}$ per hexamer. In the first step, DP3-Insulin was activated zinc in order to induce self-association; C12-Nitro-PBA was dissolved in similar solution and both solutions were mixed. Freshly prepared formulations were used for NMR analysis and for the in vivo study.

2.11. $^{11}$B-NMR Studies on the Complexation $^{11}$B NMR spectra were recorded on a VARIAN Inova-500 spectrometer operated at 160.3 MHz with gXH switchable broadband probe installed. Samples at a concentration of 10 mM were transferred to a 5 mm Norell natural quartz NMR tube (Sigma-Aldrich). Diols and 4-carboxyphenylboronic acids were co-dissolved in phosphate buffer, 0.1 M at pH 7.4 or 8.5 and tested at 37° C.

1TBA and 4NBA complexing efficiency with selected diols was measured in similar conditions but at a mixture of acetonitrile/PBS 2:1, according to the direct formulation procedure. Solid PBA-DIOL complexes were evaluated in DMSO. Data were analyzed with VNMR 6.1c software. Chemical shifts are reported in parts per million (ppm) on the δ scale.

2.12. FTIR Computer Analysis

Geometry optimizations were completed with Becke's three-parameter hybrid exchange functional with the Lee-Yang-Parr correlation functional (B3LYP) as implemented in *Gaussian* 09. Vibrational frequency analyses were performed to verify that the stationary points correspond to energy minima (zero imaginary vibrational frequencies). The DFT vibrational frequencies were corrected with a scaling factor of 0.9614.

2.13. FTIR Analysis of Solid Complexes

Samples tested for FTIR analysis were prepared using the direct complex method. However, instead of using a DP3-insulin and a hydrophobic PBA samples were prepared with Fructose and 1TBA. 1TBA and fructose were selected to model this process due to their distinguish FTIR spectra. Samples were prepared at organic/aqueous solution with pH of 7.4 or 8.5. Controls made with no fructose were prepared under similar conditions (direct method). Bulk 1TBA, fructose and their solid mixtures were also evaluated. FTIR spectra were measured with Alpha FTIR spectrometer (Bruker optics Inc.). KBr plates of samples were measured in the transmission mode.

2.14. Solubility of Hydrophobic PBA as Function of Glucose or Fructose Concentration. 10 mg of Hydrophobic PBA (4DBA, 1TBA and 4NBA) were suspended in 40 ml vials containing phosphate buffer saline with various concentrations of glucose or fructose (0-1000 mg/dL); samples were mixed for 6 hours at RT. The solid suspension was centrifuged and aliquots were evaluated for PBA concentration. Analytical HPLC (Agilent 1200) was used to analyze samples.

2.15 Diol-Insulin Analogs PBA Affinity Test

Column filled with 2 ml of boronic acid resin (immobilized boronic; 100 μmoles/mL purchased from Thermo Scientific; Prod #20244) was washed few times with PBS and then loaded with 1 mg of insulin analog, dissolved in PBS. The resin was washed with fresh PBS and the filtrate was collected as fractions. Insulin concentration in each fraction was quantified using a micro-BSA kit (Pierce) with respect to the tested analog calibration curve.

2.16. Solubility of Insulin Analogs in Phosphate Buffer Saline

Insulin analogs were dissolved in phosphate buffer along with $ZnCl_2$ (3 per Hexamer), EDTA 0.1% w/v and glycerol 5% v/v. Samples were agitated in room temperature at 100 rpm for 30 min. Aliquots of the solutions were taken following centrifugation (10,000 rpm, 5 min). Measurements were carried out relative to a calibration curve that was obtained for each analog using an analytical HPLC as depicted above; however, for this procedure the mobile phase was acetonitrile:DDW containing 0.1% TFA.

2.17. Dynamic Light Scattering Analysis of Insulin Analogs

Size distributions were measured using Zetasizer nano ZS dynamic light scattering (Malvern Instruments) equipped with a He—Ne laser at 633 nm. Experiments were performed in PBS, with scattering angle at 90° for the correlation function. Viscosity and refraction indices were set equal to those of PBS at 25° C. Insulin analogs were dissolved in phosphate buffer saline containing or lacking $ZnCl_2$. A sample with a final concentration of 3.5 mg/mL was filtered using a 0.2 μm cellulose filter directly into its designated cuvette. Each sample had 5 minutes of equilibration time prior to triple measurements (each containing at least 10 scans). The sample was then serially diluted to concentrations of 3, 2.5, 2, 1.5 and 1 mg/ml by adding the appropriate stock buffer solution (PBS or PBS containing $ZnCl_2$); and the sample was measured periodically. The entire process was repeated as a second set (i.e., a duplicate run of the entire experiment).

2.18. Ultracentrifuge of Insulin Analogs

The procedure was carried out and analyzed according to a previous protocol. Samples were formulated at a phosphate buffer at a final concentration of 2 mg/ml, along with 3 Zn per hexamer and m-cresol. Samples were evaluated for velocity sedimentation using interference optics and the data was analyzed using Sedfit-free software.

2.19. Cytotoxicity of DP3-DBCO-Insulin and DP1-DBCO-Insulin

HeLa cells were maintained in growth media consisting of RPMI-1640 with L-glutamine, penicillin/streptomycin, and 10% heat inactivated fetal bovine serum (Invitrogen Corp.). For cell viability experiments, cells were seeded in 96-well plates at 10,000 cells per well and allowed to settle overnight. Afterward, the media was removed and replaced with 150 μL growth media and 50 μL of sample compound, dissolved in phosphate buffered saline and filtered through a 0.02-μm Anotop filter (Whatman, Clifton, N.J. 07014). After 72 hours growth media was removed and wells were washed once with Hanks Balanced Salt Solution, with calcium and magnesium (Invitrogen, Carlsbad, Calif.). MTS assay solution (CellTiter 96® AQueous One Solution Cell Proliferation Assay, Promega Corp., Madison, Wis.), was added to each well according to provider's directions and allowed to incubate for 3 hours. The media was then transferred to a new plate before reading the absorbance at 490 nm.

2.21 In Vivo Work with STZ Induced Diabetic Mice

All procedures used in animal studies were approved by the Committee on Animal Care at MIT and were consistent with local, state, and federal regulations prior initiation of this research. STZ-induced mice were purchased from the Jackson laboratory (MA, USA) (C57BL, male, 6 weeks). Insulin formulations were freshly prepared by dissolving the appropriate insulin analog or the native form in PBS (0.1 M, pH 7.4, $ZnCl_2$:3 Zn per hexamer) to a final concentration of 0.026 mM (0.15 mg/ml for Native-insulin). The pH was adjusted to pH 7.4 in case C12-Nitro-PBA was added to the formulation. Each tested group consisted of 4 STZ-induced diabetic mice; animals initial blood glucose levels were measured by bleeding their tails and collecting 2-5 ul of blood to a glucose test strip meter (Clarity Plus; Diagnosis Inc). Animals were then subcutaneous injected with 80 ul of the formulation (1×) or 40 ul (0.5×). Blood glucose levels were tested every 30 minutes over a span of 6-7 hrs. The animals were then humanly sacrificed at the end of the experiment. Data is presented is the average value of each time point for each 4 animals.

3. Results and Discussion 3.1 Synthesis and Characterization of Alkyne Modified Insulin at B29 Lysine Residue.

Human insulin has a single lysine residue within its primary structure; it was selected for modification at this specific w-amino group. There are also two other free amino groups located on the N-termini of both chains, but the amino group of B29 is more reactive than the other two in a basic anhydrous solution, and therefore can be selectively modified. Furthermore, conjugation at this location was previously found to preserve the hormone's in vivo bioactivity [Evans et al., *Diabetes, Obes. Metab.* 2011, 13, 677-684]. Native insulin was functionalized with an alkyne by reacting it with NHS activated propargyloxy propionate (FIG. 15 (Scheme 1)). The conjugation reaction was very efficient and reached completion within 30 minutes at room temperature. Most of the organic impurities and solvent with a molecular weight less than 3500 Da were effectively removed by dialysis. After lyophilization, the modified insulin (Al-insulin) was purified with preparative HPLC. Insulin was also modified using DBCO-NHS esters and purified in a similar manner (DBCO-insulin). Both reactions were optimized for the molar equivalents of the modifying reagent. It was found that the desired modification requires a use of a single equivalent of alkyne; when two or more equivalents of NHS ester were added, the crude product mainly consisted of insulin functionalized with multiple conjugates. Purified Al-insulin and DBCO-insulin were characterized with LC-MS (supporting information). Pure insulin products with single modification was obtained with an overall yield of 30-40% following lyophilization. The modification was confirmed with amino acid sequencing of proteolytic peptides from trypsin digestion.

3.2. Study of Two 'Click-Chemistry' Methods for Secondary Conjugation of Al-Insulin and DBCO-Insulin to Diols.

Alkyne modified insulin was further modified with azido-terminated compounds. The copper-catalyzed azide-alkyne cycloaddition is a well-known "click" chemistry tool and it is widely used in bio-conjugation [Ganesh et al., *Chem.—Asian J.* 2011, 6, 2670-2694]. Initial attempts to functionalize Al-insulin without the use of a chelate resulted with multiple modifications as reflected by the LC-MS data (supporting information). Therefore the process was amended [Hong et al., *Angew. Chem., Int. Ed.* 2009, 48, 9879-9883, S9879/9871-S9879/9810] by using a co-solvent system of PBS/DMSO in order to overcome the low solubility of hydrophobic chelate (TBTA) in aqueous solution. An excess of over 100 equivalents of azido was needed. Even though this modification was successful, it is relatively tedious and inefficient, and an alternative method was explored.

Figure 15:
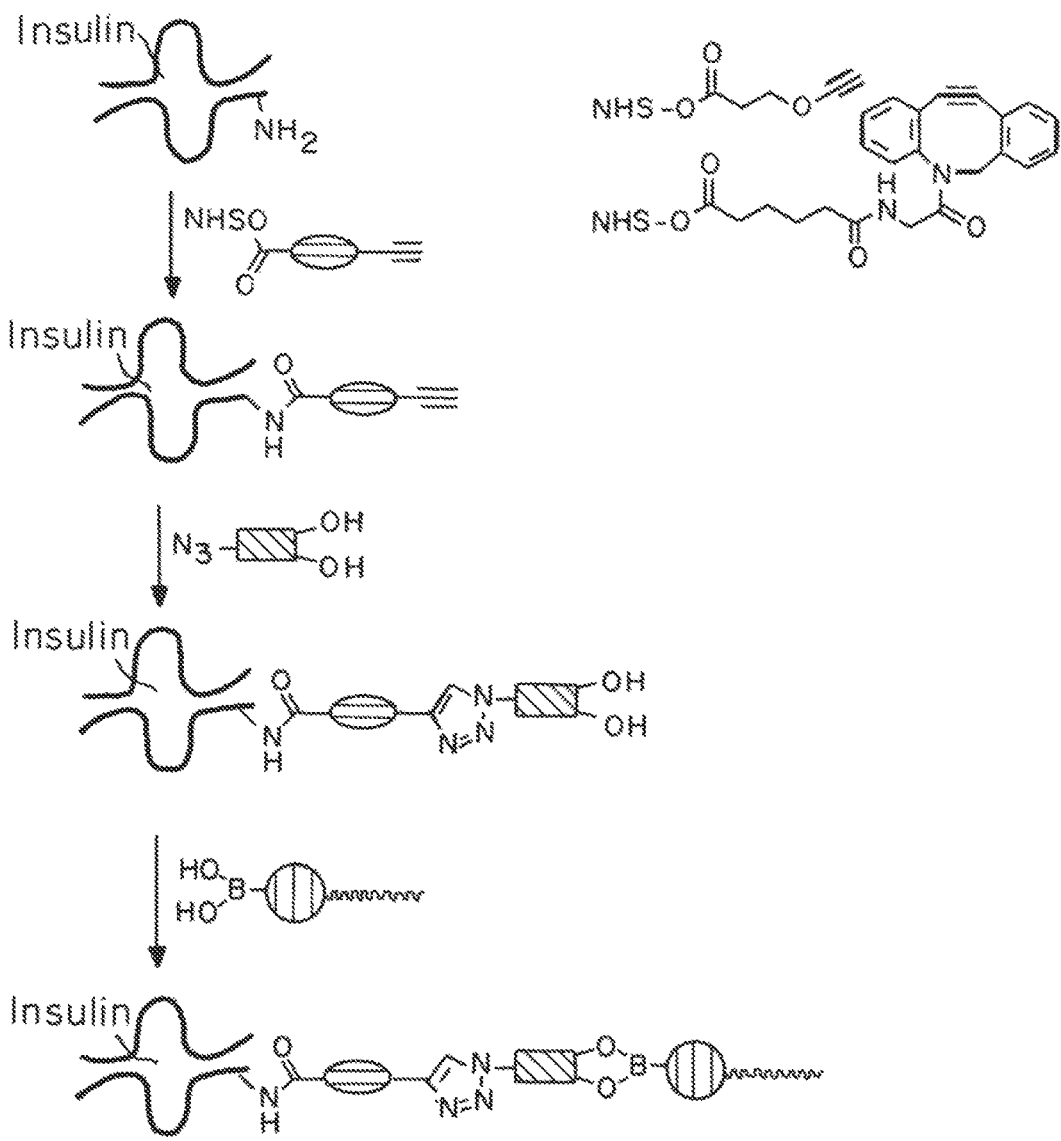
FIG. 15 is a diagram of Scheme 1, Native human recombinant insulin was chemically modified on the B29 lysine.
Figure 16A:
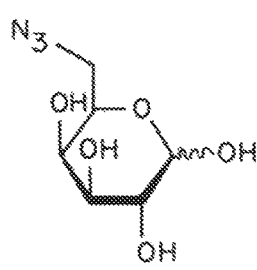
FIGS. 16A-16F are diagrams of the chemical structures of azido diols and diol compounds, which were evaluated via $^{11}$B NMR. (A) 6-azido-6-deoxy-D-galactose, (B) 1-Azido-1-deoxy-β-D-lactopyranoside, (C) α-D-Mannopyranosyl azide, (D) 8-azidoadenosine, (E) Dopamine. (F) Azido-Pentanoic-DOPA$_2$-GLY-GLY-DOPA$_2$-GLY-NH$_2$; DP3 peptide was synthesized using Fmoc protected amino acids and Fmoc-3,4-dihydroxy-phenylalanine, acetonitrile protected. 5-azido pentanoic acid was finally conjugated to the N-terminus. DP3: m/z 963.22.
Figure 16B:
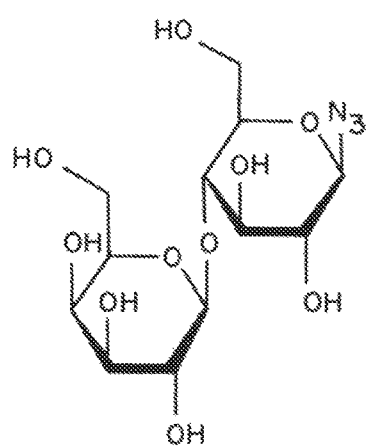
Figure 16C:
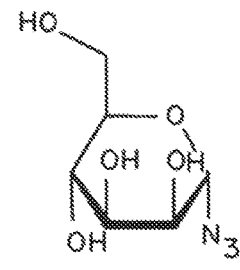
Figure 16D:
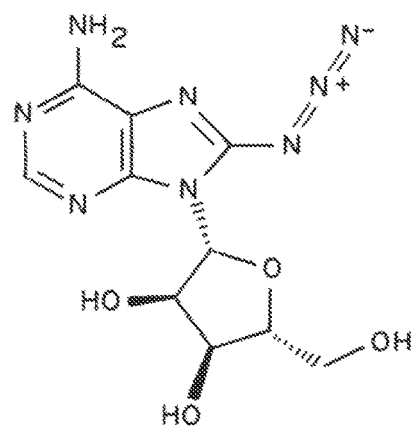
Figure 16E:
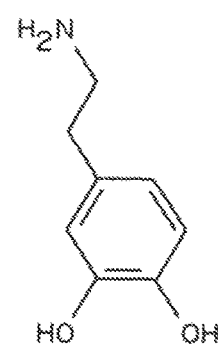
Figure 16F:
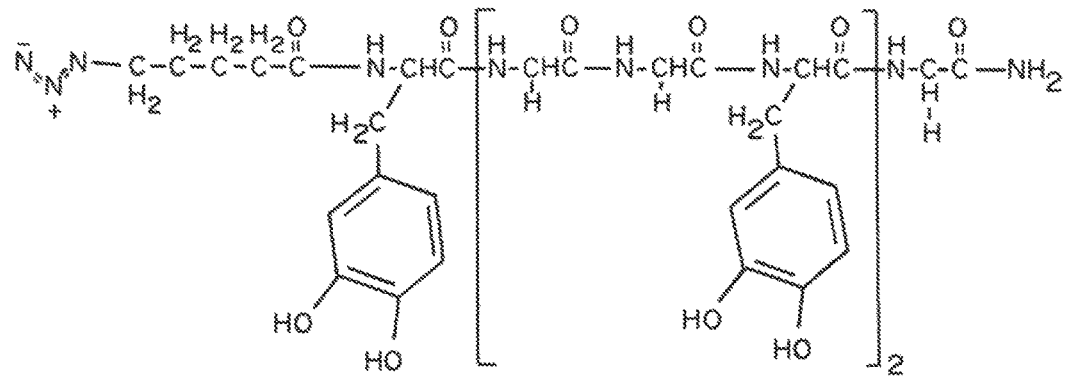

A second method used was metal-free alternative click chemistry (FIG. 15 (Scheme 1)), involving the cycloaddition between strained cycloalkyne and azide as introduced by Bertozzi and coworkers [Agard et al., *J Am Chem Soc* 2004, 126, 15046-15047], and has found many applications in biological applications [Lutz, *Angew. Chem., Int. Ed.* 2008, 47, 2182-2184], due to the simple procedure, high yield, and easy purification process. Here, the reaction was efficiently carried out, and the crude product was purified via dialysis against water. Sample purity was confirmed using LC-MS (supporting information). The solubility of functionalized DBCO-insulin was found to depend on modifications (Figure S1). The copper-free method was pursued over the copper-catalyzed reaction used above because it does not involve the use of expensive insoluble chelates. It was determined that this approach is best suitable for insulin modification.

3.3. Screening for Azido Diols Based on their Complexation Ability with PBA

PBA is known to recognize and bind to compounds containing 1,2- and 1,3-diol residues via the formation of a boronate ester [Wang et al., *Curr. Org. Chem.* 2002, 6, 1285-1317]. At aqueous conditions the boronate ester is a dynamic complex. It was hypothesized that by carefully pairing a diol with hydrophobic PBA, long-acting insulin with extended bioavailability that is released based on blood glucose levels could be generated (FIG. 15 (Scheme 1)). In order to achieve this goal, a variety of commercially available azido substituted diols were tested for their ability to complex with PBA. Various monosaccharides were shown to bind with PBA, even though the specific mechanism of interaction is still not clearly understood [Springsteen and Wang, *Tetrahedron* 2002, 58, 5291-5300]. In addition, the effect of azide group on the binding with PBA is unknown. Therefore, 4 commercially available azido diols (FIGS. 16A to 16D) were selected for testing based on their diverse structures. These compounds include azido-substituted monosaccharides (A and C), disaccharide (B), oligosaccharide (C), adenosine (D) and dopamine (E). The complexation between 4-carboxyphenylboronic acid and above materials was evaluated using $^{11}B$ NMR (FIG. 16, Table 1).

TABLE 1

$^{11}B$ NMR analysis of the complexation efficiency of 4-carboxyphenylboronic acid with selected diols. PBA concentration is 10 mM; diol concentration is with respect to used equivalence. Samples were dissolved in phosphate buffer saline 0.1M and were tested at 37° C.

| Compound | pH | Equivalence (PBA:Diol) | Complex % |
|---|---|---|---|
| Glucose | 7.4 | 1:10 | 22.8 |
|  | 7.4 | 1:2 | 11.0 |
|  | 7.4 | 1:1 | 4.0 |
|  | 8.5 | 1:2 | 49.4 |
| Frucrose | 7.4 | 1:10 | 44.9 |
|  | 7.4 | 1:2 | 34.9 |
|  | 7.4 | 1:1 | 27.4 |
|  | 8.5 | 1:2 | 67.3 |

TABLE 1-continued $^{11}$B NMR analysis of the complexation efficiency of 4-carboxyphenylboronic acid with selected diols. PBA concentration is 10 mM; diol concentration is with respect to used equivalence. Samples were dissolved in phosphate buffer saline 0.1M and were tested at 37° C.

| Compound | pH | Equivalence (PBA:Diol) | Complex % |
|---|---|---|---|
| 1-Azido-1-deoxy-beta-D-lactopyranoside | 7.4 | 1:2 | 4.0 |
|  | 8.5 | 1:2 | 8.3 |
| Alpha-D-Mannopyranosyl azide | 7.4 | 1:2 | 4.2 |
|  | 8.5 | 1:2 | 22.5 |
| 6-azido-6-deoxy-D-galactose | 7.4 | 1:2 | 17.6 |
|  | 8.5 | 1:2 | 74.9 |
| 8-Azido-Adenoside | 7.4 | 1:2 | 47.6 |
|  | 8.5 | 1:2 | 61.6 |
| Maltoheptaose | 7.4 | 1:1 | 7.5 |
|  | 8.5 | 1:1 | 4.0 |
| Dopamine | 7.4 | 1:10 | 58.1 |
|  | 7.4 | 1:2 | 38.7 |
|  | 8.5 | 1:2 | 100.0 |

The chemical shift of boron in PBA changes when it is complexed with a diol. For example, the neutral trivalent PBA shows a chemical shift at about 10 ppm, while the boronate ester is shifted to −10 ppm. Therefore, the efficiency of complexation was estimated by monitoring the ratio of these two peaks. The effect of pH on complexation and structure of diols was studied. As shown in Table 1, free glucose showed only minimal complexation at pH 7.4, with 11% at a 2:1 ratio (diol/PBA). However, the complexation was significantly increased at elevated pH. Complexation was up to 50% by increasing 1 pH unit (pH 8.5). It also showed the azido groups at the anomeric position abolished the binding ability with PBA completely. Fructose bounded better, and the complexation was 35% (pH 7.4), which was consistent with previous studies [Springsteen and Wang, *Tetrahedron* 2002, 58, 5291-5300]. Overall, at physiological pH, D showed the highest complexation (48%), followed by E (39%), and fructose (35%). However, D did not survive click reactions because of degradation.

It was previously shown that dopamine is able to associate 10 times more effectively with PBA relative to glucose [Springsteen and Wang, *Tetrahedron* 2002, 58, 5291-5300]. A short peptide comprising of multiply DOPA groups was designed to ensure full conjugation at physiological pH. Azido-Pentanoic-DOPA-[GLY-GLY-DOPA]$_2$-GLY-NH$_2$ (DP3-peptide) was characterized with HPLC and MALDI-TOF (supporting information). DP3-peptide (FIG. 16F) was clicked to DBCO-insulin and the DP3-insulin was obtained. Data regarding the cytotoxicity showed that DP3-insulin acts similarly to native insulin, and was non-toxic (supporting information)

Figure 17:
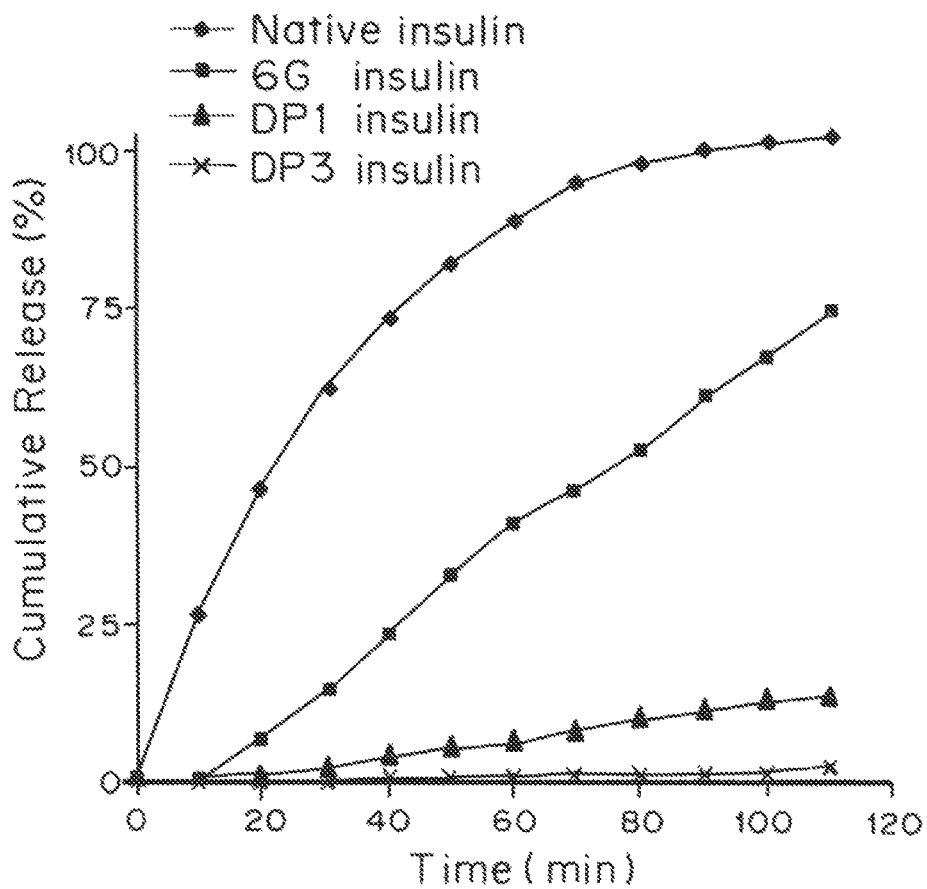
FIG. 17 is a graph showing the affinity interaction of modified insulin with immobilized boronic acid resin. The column was filled with 2 ml of boronic acid resin, loaded with 1 mg of insulin Analog. The resin was washed with fresh PBS and the filtrate was collected as fractions. Insulin concentration was quantified using a micro-BSA kit with respect to Analog calibration curve.

The affinity of modified insulin with PBAs was investigated with a PBA conjugated resin. As shown in FIG. 17, about 85% native insulin was recovered, while 6-galactose modified insulin had a recover less than 40%, DP1-insulin (peptide modified with a single dopamine group) had less than 10% recovery, and DP3-insulin (three dopamine group) had less than 5%. Diol-modified insulin showed the strongest affinity to the resin, in agreement with the $^{11}$B NMR data.

3.5. Screening of PBA Derivatives

It has been reported the pK$_a$ of PBA is important for binding with diol. It is usually assumed that the complex stability is significantly enhanced at pH above the pK$_a$ of the boronic acid [Hordern, *Drugs Today* 2006, 42, 505-517]. Various PBAs with lower pK$_a$s relative to physiological pH have been developed (i.e., o-dialkylaminomethyl phenylboronic acid). Different PBA derivatives were screened to determine optimal binding. Three PBAs (supplementary information) with different plcs and hydrophobicities were selected for complexation with DP3-insulin. Hydrophobic PBAs were selected because the expected long-acting effect they would have in insulin release, due to the resulting intermolecular hydrophobic interactions.

Figure 18:
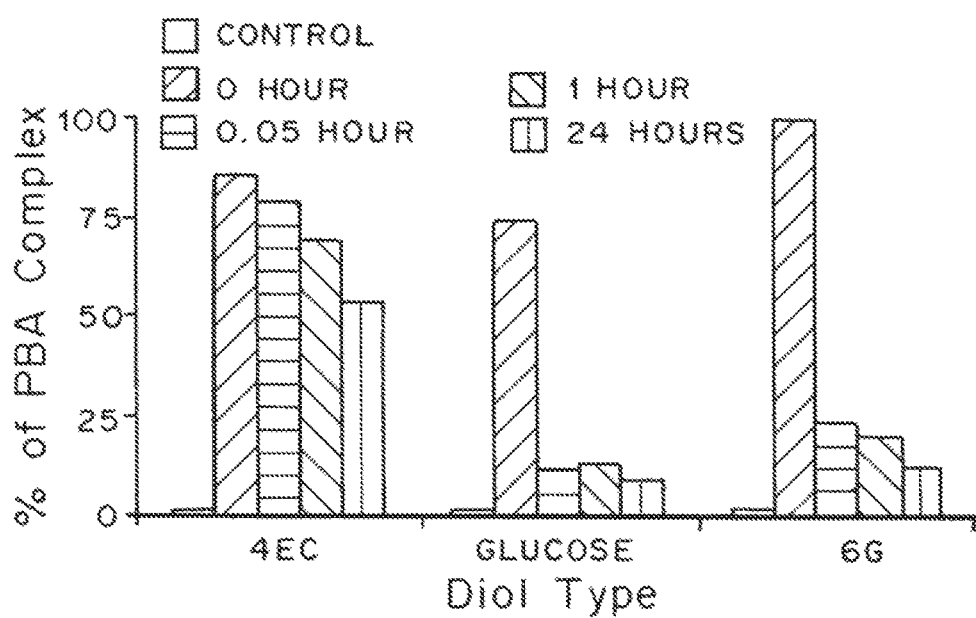
FIG. 18 is a graph showing $^{11}$B NMR analysis for the stability of 4NBA:diol complexes at phosphate buffer, 0.1 M, pH 7.4, 37° C. Solid complexes were suspended in phosphate buffer saline and were agitated for 0, 0.05, 1 and 24 hours. Solids were then separated via centrifugation and freeze dried. Samples were dissolved in DMSO-d$^6$ at a concentration of 10 mM and were tested at room temperature.
Figure 19A:
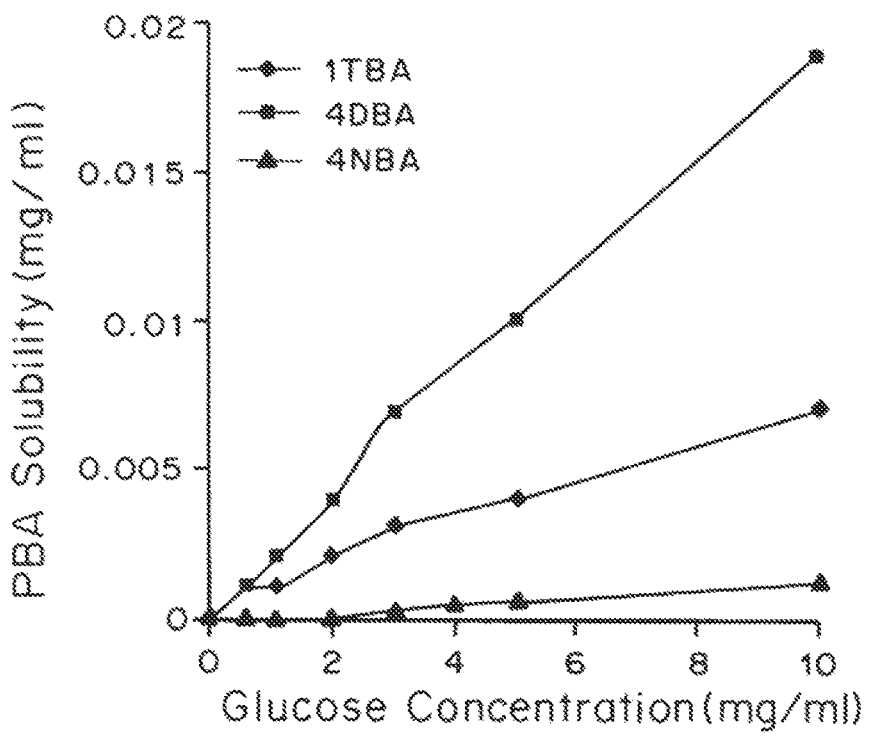
FIGS. 19A and 19B are graphs showing hydrophobic PBAs (1TBA, 4DBA and 4NBA) tested as a function of glucose (A) and fructose (B) concentrations in PBS. 10 mg of solid, hydrophobic PBA were dispersed in 50 mL of phosphate buffer saline containing various concentrations of glucose and fructose; samples were mixed for 6 hours at room temperature, centrifuged, and aliquots were quantified against a calibration curve using reverse phase HPLC.
Figure 19B:
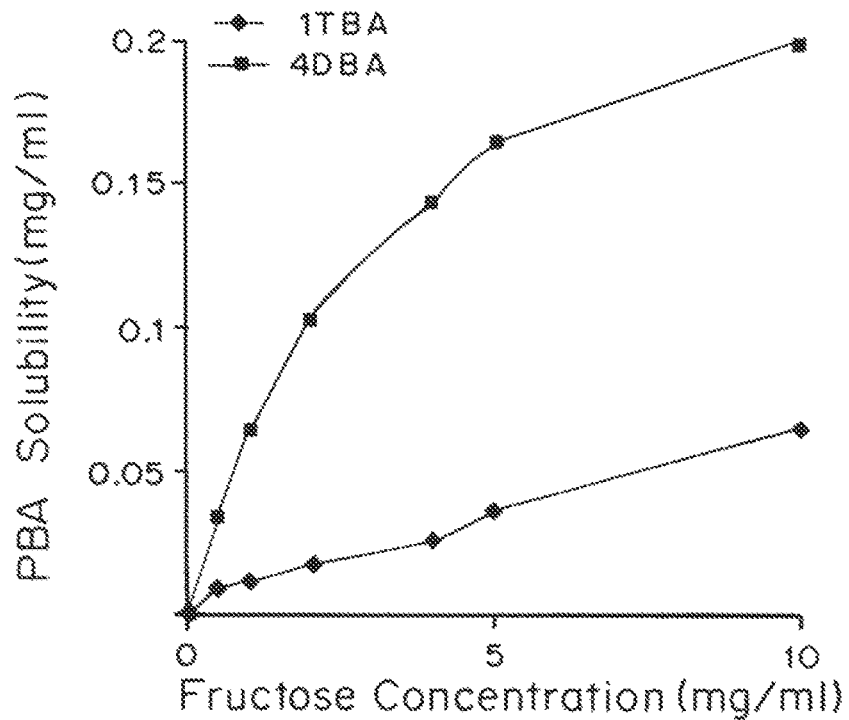

Complexation of DP3-Insulin with PBA was studied with $^{11}$B NMR between 4NBA, 1TBA and selected diols (Table 2). It was demonstrated that 4EC (a model for dopamine) complexes effectively with both 1TBA (75%) and 4NBA (87%) at a pH of 8.5. However, the complexation ratio dropped to 10% at a pH of 7.5. In addition, 4-EC complexes with fructose suspended in PBS remain above 50% of complexed form after 24 hr, while glucose remain less than 10%. (FIG. 18) Synthesized DP3-peptides demonstrated 91% of complexation with 4NBA at pH 8.5. This compound demonstrated high degree of complexation with 74% for glucose, and nearly 100% with fructose. Therefore, 4NBA was selected for further studies due to its low solubility and response range within expected diabetic glucose levels (FIG. 19).

TABLE 2

$^{11}$B NMR analysis for the complexing efficiency of 4NBA with selected diols. PBA concentration is 10 mM; diol concentration is with respect to used equivalence. Samples were dissolved in a mixture of acetonitrile and phosphate buffer saline 0.1M and were tested at room temperature.

| Compounds | pH | Equivalence (PBA:Diol) | Diol-PBA Complex % |
|---|---|---|---|
| 1TBA:4EC | 7.4 | 1:1 | 8.1 |
| 1TBA:4EC | 8.5 | 1:1 | 75.0 |
| 4NBA, 10 mM | 8.5 | — |  |
| 4NBA:4EC, 10 mM | 8.5 | 1:1 | 86.8 |
| 4NBA:4EC, 10 mM | 8.5 | 1:0.5 | 56.6 |
| 4NBA:DP1-Azido peptide, 10 mM | 8.5 | 1:1 | 80.7 |
| 4NBA:DP3-Azido peptide, 10 mM | 8.5 | 1:1 | 91.1 |

The complex formation with fructose and 1TBA was also confirmed with FTIR (supporting information). The characteristics peak at ~1400 cm$^{-1}$ associated with boronic acids was missing when the complexes were made at pH 8.5, consistent with the boronate form. In contrast, at pH 7.4, the characteristic peak had a similar pattern to those of the non-conjugated PBA because of the low complex efficiency.

Although the direct complexation approach demonstrated a high degree of efficiency with diol models, it was found to be less effective in practice. The solid formulations formed could not be suspended effectively in phosphate buffer and therefore could not be used for subcutaneous (SC) injections.

3.5. Soluble Insulin Analogs Formulation Using Zn and C12-Nitro-PBA

Figure 20A:
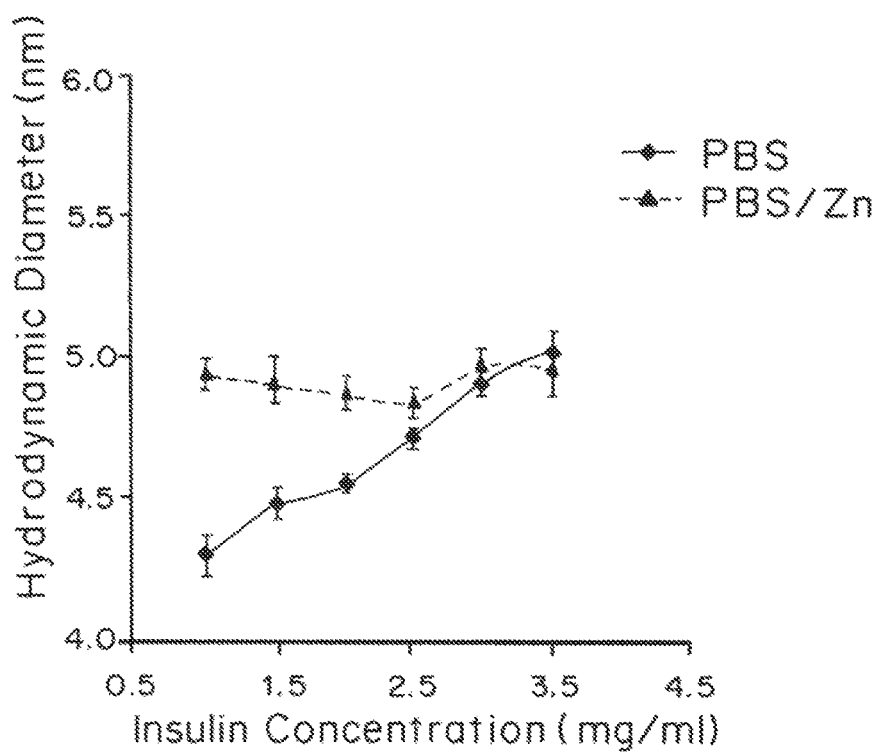
FIGS. 20A-20E are graphs showing dynamic light scattering measurements of insulin hydrodynamic diameters as a function of insulin and Zn$^{2+}$ concentration. (A) 6G-DBCO-insulin, (B) 6G-DBCO-insulin (PBS), (C) DBCO-insulin (PBS, ZnCl$_2$), (D) DP3-DBCO-insulin (PBS), (E) DP3-DBCO-insulin (PBS, ZnCl$_2$).
Figure 20B:
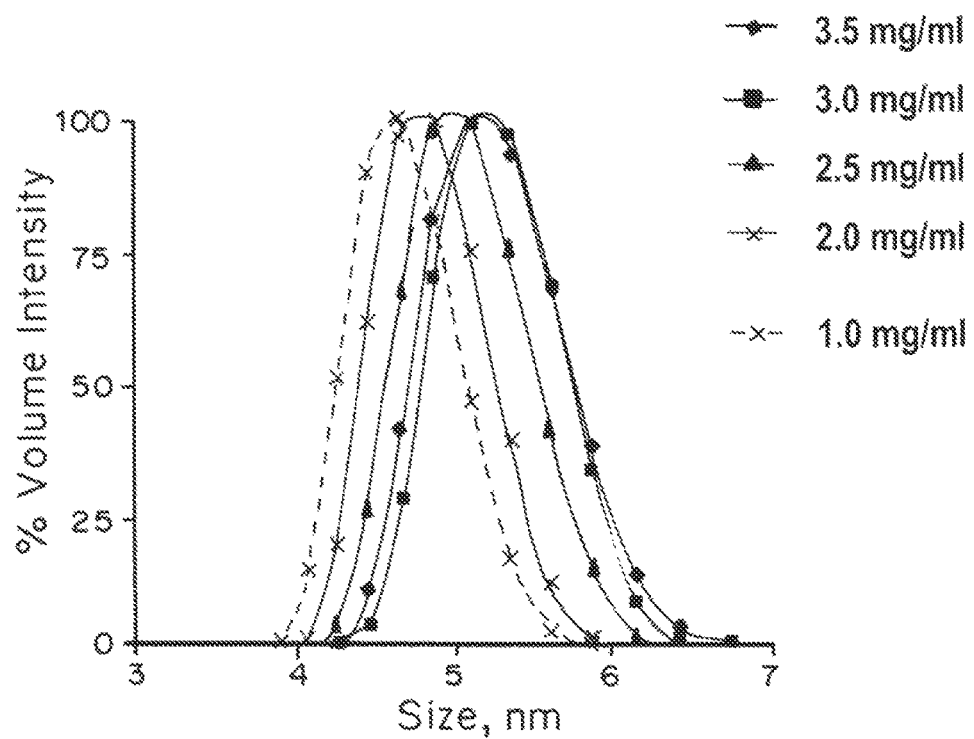
Figure 20C:
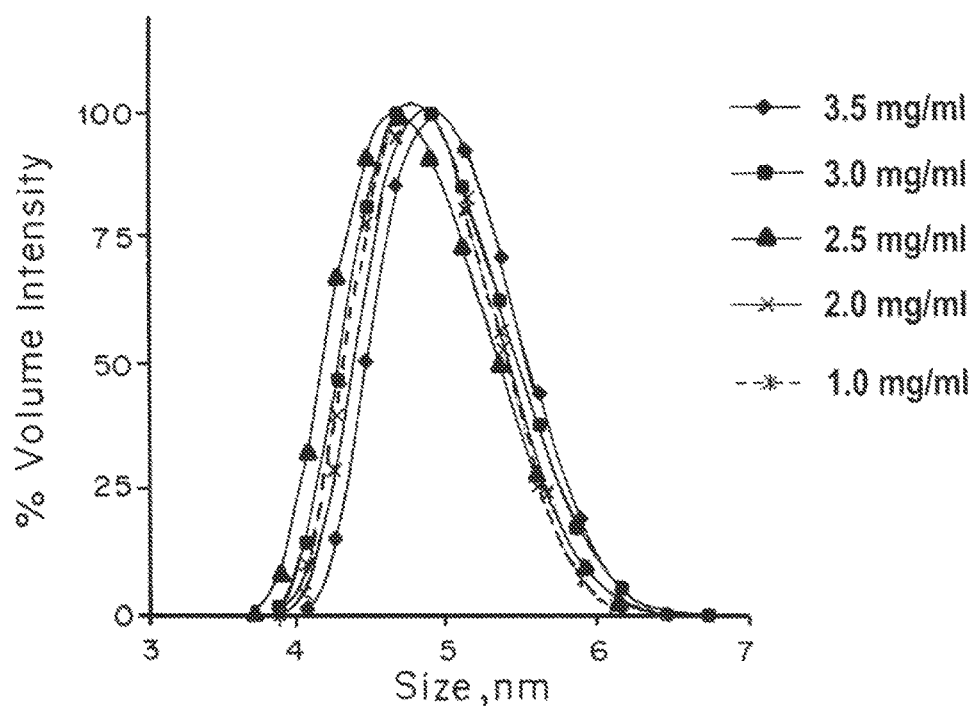
Figure 20D:
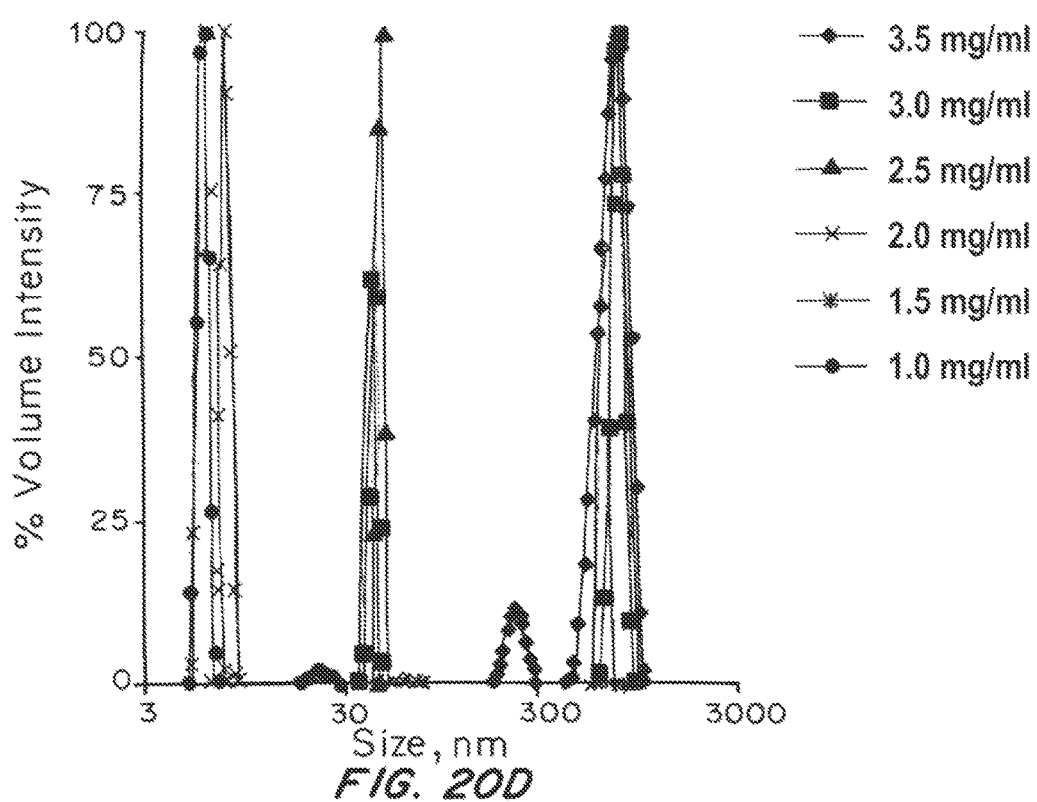
Figure 20E:
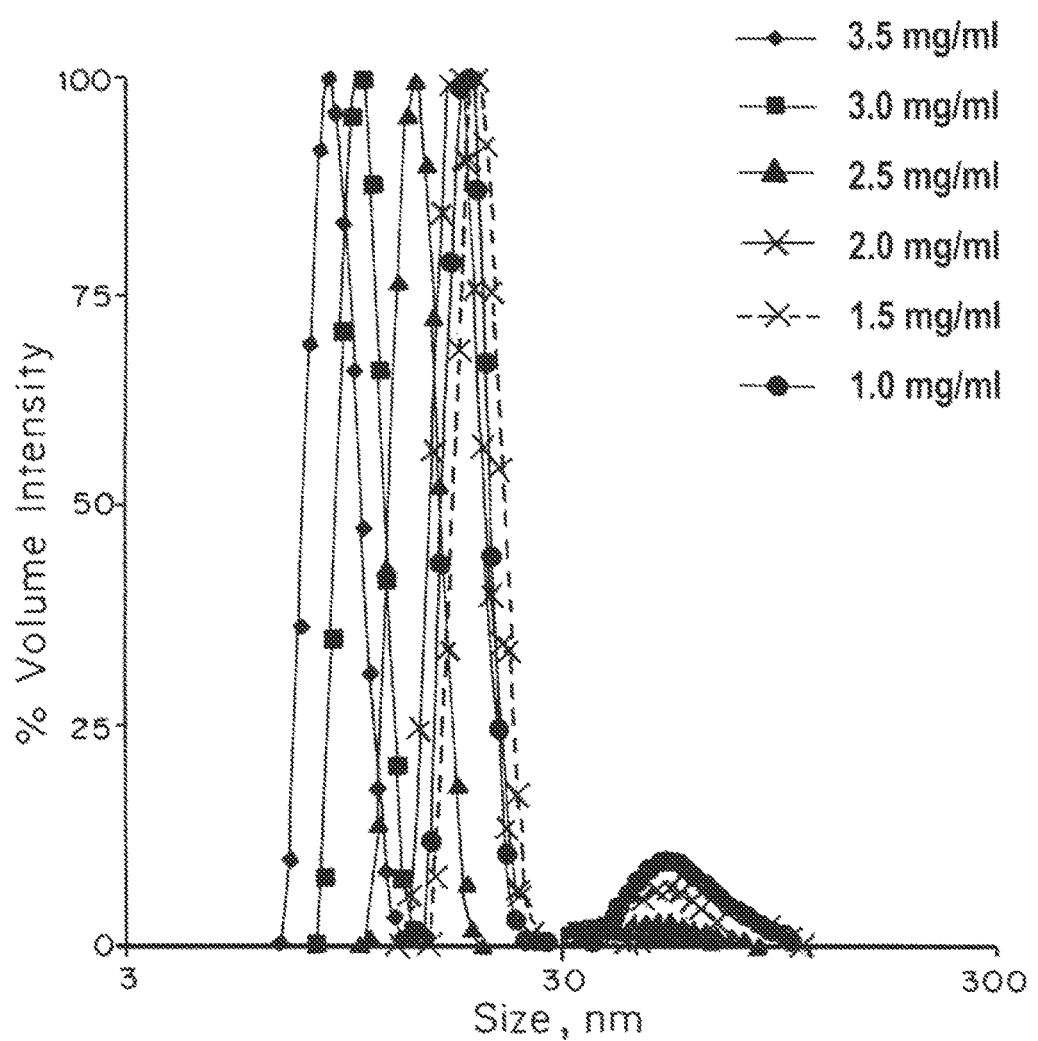

To overcome the low solubility discussed above, an alternative formulation approach was explored by using the ability of insulin to self-associate. The self-association properties of the analogs were studied using a dynamic light scattering device (DLS) [Hvidt, *Biophys. Chem.* 1991, 39, 205-213] and ultracentrifuge (UC) [Richards et al., *Pharm. Res.* 1998, 15, 1434-1441] techniques. Insulin forms a hexamer with the presence of Zn$^{2+}$ ions, as well as at high insulin concentrations (above 3 mg/ml) [Hvidt, *Biophys. Chem.* 1991, 39, 205-213]. The literature value for the hydrodynamic diameter of monomeric insulin dissolved in phosphate buffer is around 3.5 nm, while the hexamer form has a typical size close to 5.6 nm [Hvidt, *Biophys. Chem.* 1991, 39, 205-213]. Various insulin analogs were tested using the DLS method (FIG. 20). Samples were prepared by dissolving an analog in phosphate buffer with or without $ZnCl_2$ (3 $Zn^{2+}$ per hexamer). Hydrodynamic diameter measurements started at 3.5 mg/ml, and then samples were periodically diluted to 3, 2.5, 2, 1.5 and 1 mg/ml with their respective phosphate buffer solutions (with or without $Zn^2$). Insulin modified with 6-galactose showed similar properties as previously reported for native insulin (FIG. 20A). While the hydrodynamic diameter of the self-associated analogs was stable in the presence of zinc, it gradually decreased from 5 to 4.2 nm when the samples were formulated in PBS. In contrast, DP3-insulin demonstrated large clusters when formulated in PBS and were gradually decreasing in size at lower concentrations. This behavior is probably due to the bulky nature of the analog conjugate, which generates strong hydrophobic interactions. The addition of zinc to DP3 insulin formulations helped to enhance hexamerization and thus reduce the hydrodynamic diameters of the generated clusters.

Formulations of modified insulin were further analyzed with UC (supporting information). Native insulin was formulated with m-cresol and $Zn^{2+}$. Native insulin mainly exists in the hexamers form (S.D 3.3) with minor populations of monomers and trimers (S.D 2.0). DBCO-insulin showed the presence of dimers, trimers, and in addition, large molecular weight aggregates (SD 4.5), demonstrating that analogs not only preserve their capacity to self-associate, but also have the ability form large structures as well.

Figure 21:
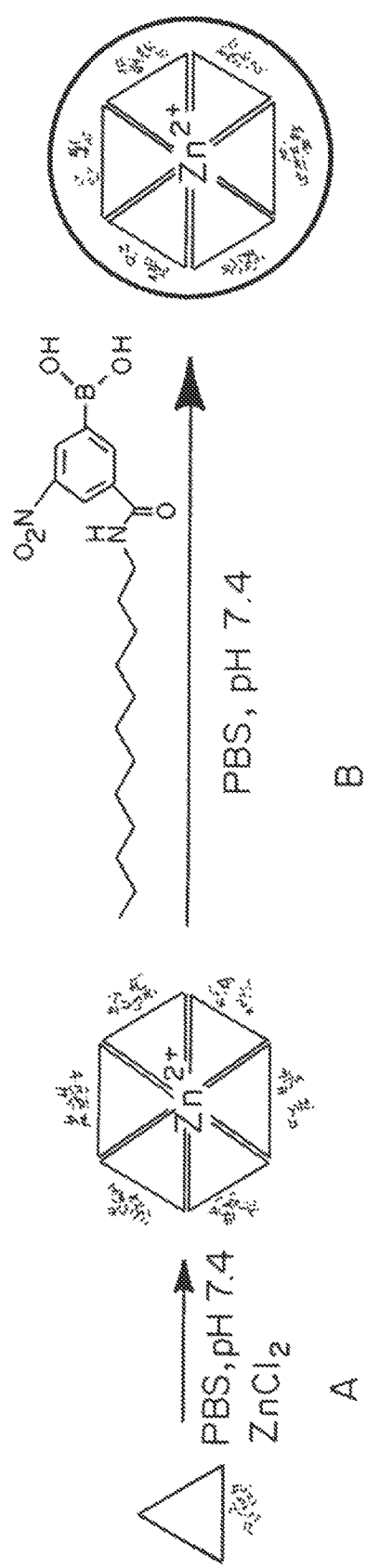
FIG. 21 is a diagram of Scheme 2, Preparation of long-acting insulin formulations via hydrophobic interactions and PBA-diol interactions. For Reaction A, DP3-insulin is dissolved with 2 Zn$^2$ per hexamer to induce self-association. For Reaction B, DP3-Insulin Hexamers are conjugated with hydrophobic PBAs to generate self-associated insulin structures that have a hydrophobic outer layer.

DP3-insulin was formulated with an aliphatic modified PBA (C12-nitro-PBA) in aqueous solution in the presence of $Zn^{2+}$ (FIG. 21 (Scheme 2)). C12-nitro-PBA was synthesized because it has low $pK_a$ of about 6.5. The low $pK_a$ of the compound has increased solubility and optimal binding affinity with the DP3-insulin under physiological conditions. The complex formed is expected to induce intermolecular hydrophobic interactions between self-assonating insulins. Accordingly, DP3-insulin was formulated with $Zn^{2+}$ to induce self-association, and then mixed with C12-nitro-PBA in order to induce complexing via hydrophobic interaction.
3.6. In Vivo Testing of the Soluble Insulin Formulation Hydrophobic insulin formulations were freshly prepared by dissolving DP3-insulin in phosphate buffer saline containing three $Zn^{2+}$ ions per hexamer. $C_{12}$-nitro-PBA was dissolved in a similar solution and the complex was formed upon mixing at room temperature (supporting information). Controls that contain C12-insulin, native insulin and DP3-insulin but no PBA were prepared similarly. Each group tested consisted of 4 STZ-induced diabetic mice that were subcutaneous injected with either 80 μl (1×) or 40 μl (0.5×) of the formulation. Blood glucose levels were monitored every 30 minutes over at least 6 hrs. The glucose level data that is presented here is an average of measurements taken from 4 different animals.

Figure 22A:
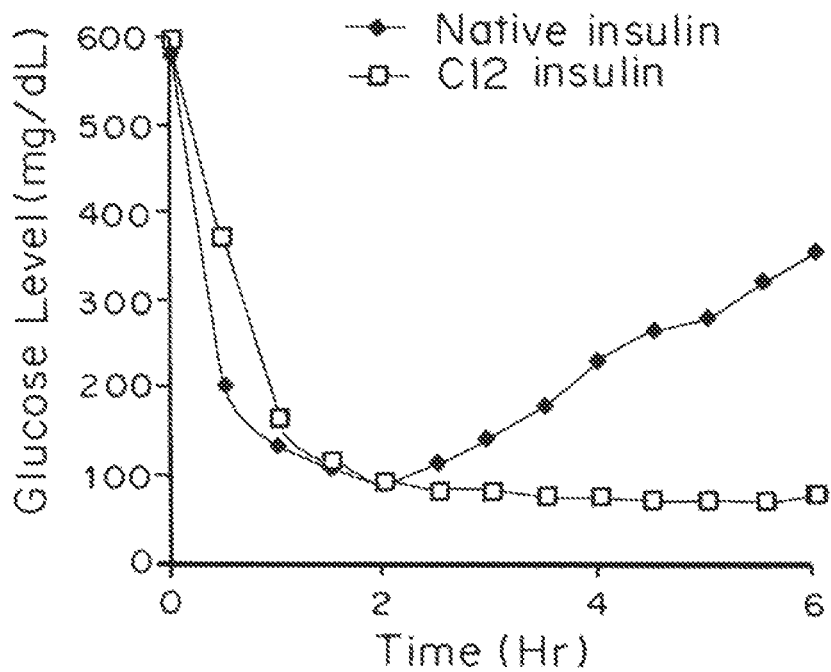
FIGS. 22A-22C are graphs showing in vivo insulin data for SC injections of STZ induced mice. (A) C12-insulin versus native insulin X1 dose, (B) DP3 insulin versus DP3-insulin/C12-N-PBA versus native insulin X1 dose, (C) DP3-insulin versus DP3-insulin/C12-N-PBA×0.5 dose.
Figure 22B:
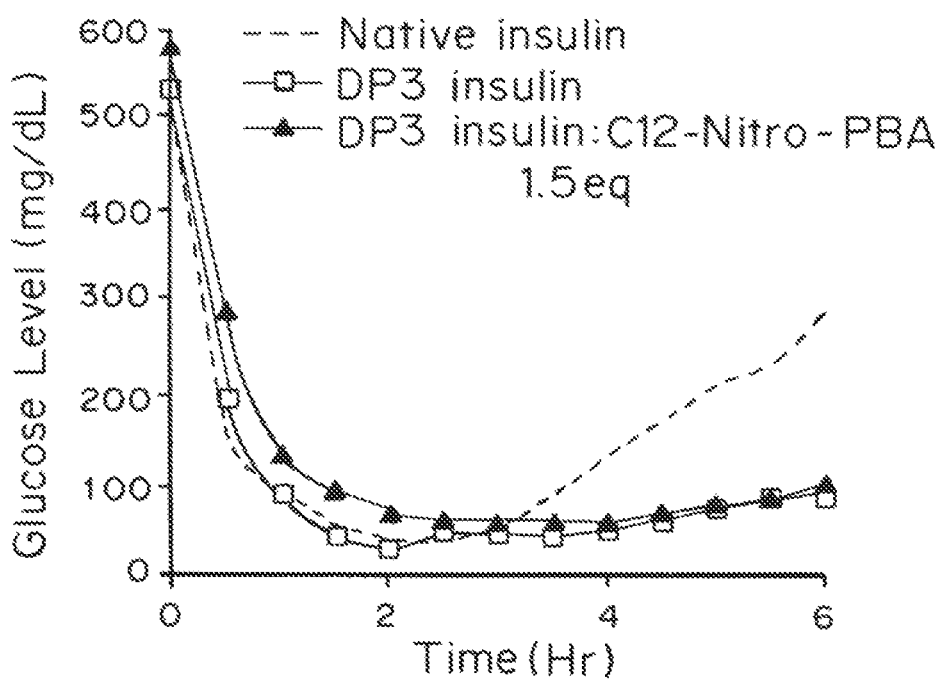

As shown in FIG. 22A, C12-insulin, prepared by conjugating insulin to an aliphatic chain, demonstrated the expected [Hordern, *Drugs Today* 2006, 42, 505-517], long acting properties relative to native insulin. Similarly, DP3-insulin (B) maintained low glucose level for least six hours, while the native insulin control shifts mice glucose levels back to a high glycemic index in less than 2 hours. Complexing DP3-insulin with C12-Nitro-PBA and $Zn^{2+}$ was expected to generate hydrophobic interactions (FIG. 21 (Scheme 2)), which would extend the formulation release time out of the injection site. It is seen in FIG. 22B that while the free DP3-insulin reduced glucose level quickly (steep curve), and got it to a minimum after about 2 hours, the DP3-insulin/C12-Nitro-PBA complex showed gradual decreases in glucose level over 3 hours. Since the DP3-insulin has increased hydrophobic interactions, it acted as a long acting analog and therefore differences in glucose levels caused by both groups after 3 hours could not be distinguished.

Figure 22C:
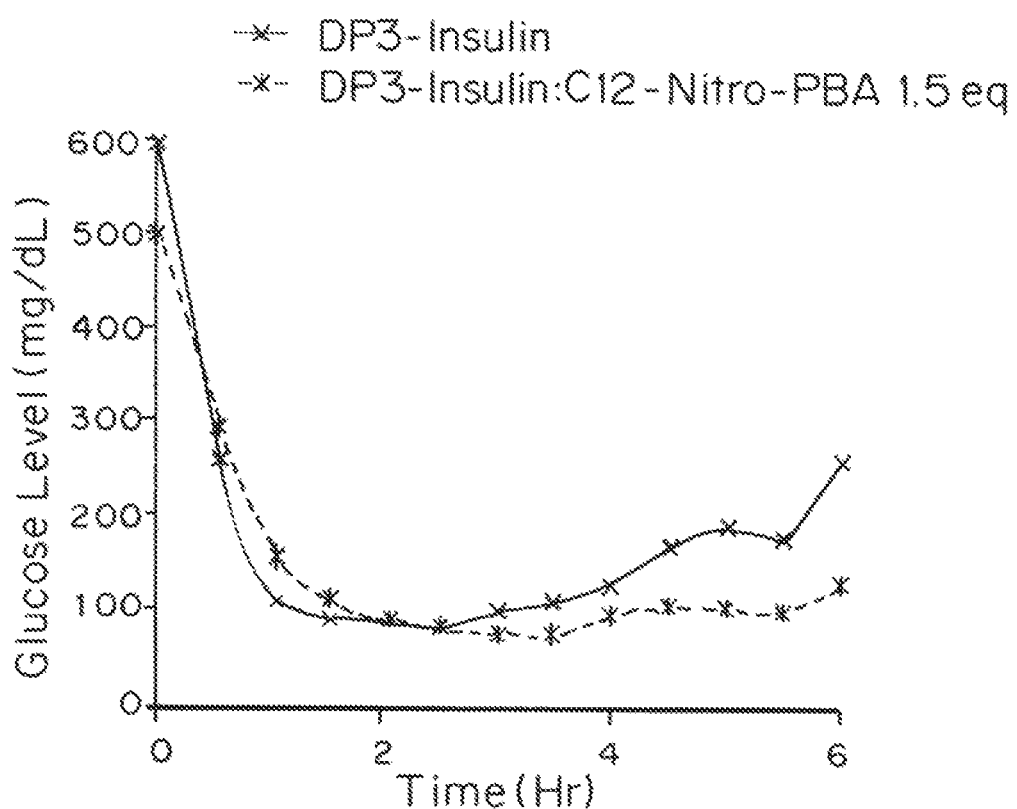
Figure 23A:
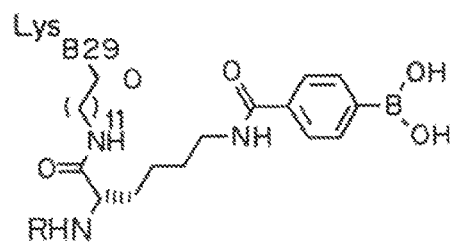
FIGS. 23A-23G are diagrams of representative structures of derivatized insulin. Core structures A-C have a phenylboronic acid (PBA) moiety, which could bind with glucose to change the properties of insulin. Core structures D-F have a PBA group and a glucamine, which can self-associate to form aggregates. The R group in red can be appended by different functional groups and substituents, shown in G, which provide the diversity of the whole library.
Figure 23B:
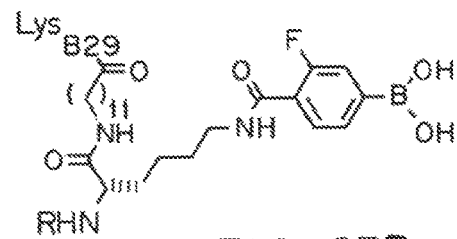
Figure 23C:
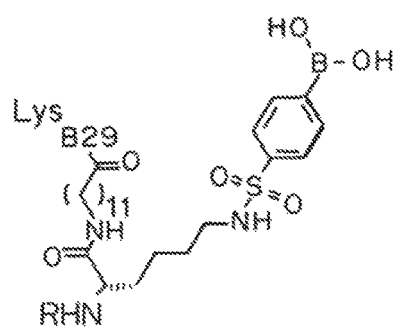
Figure 23D:
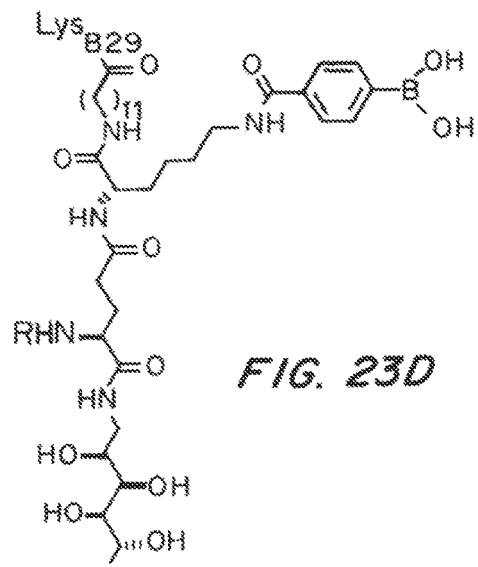
Figure 23E:
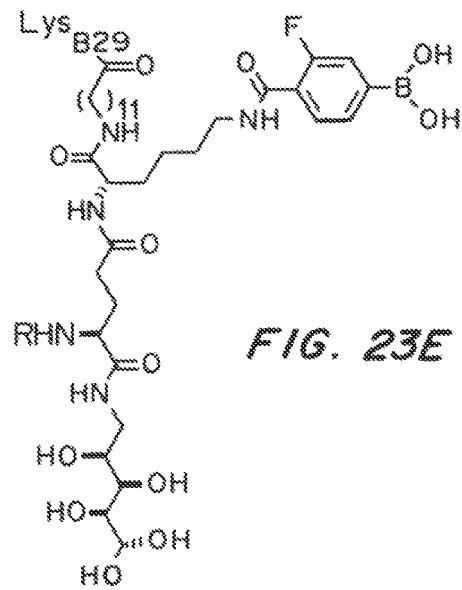
Figure 23F:
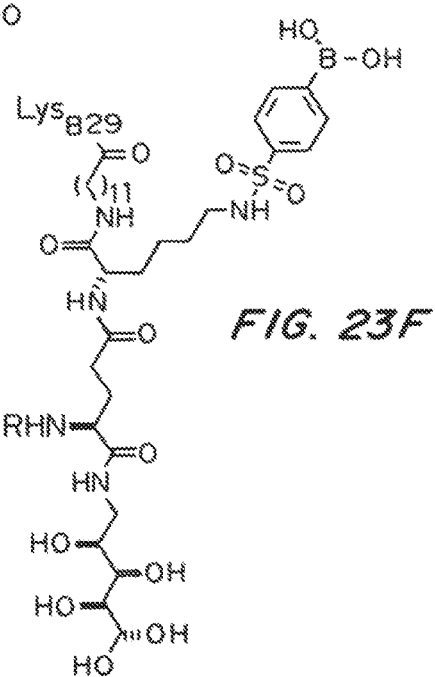
Figure 23G:
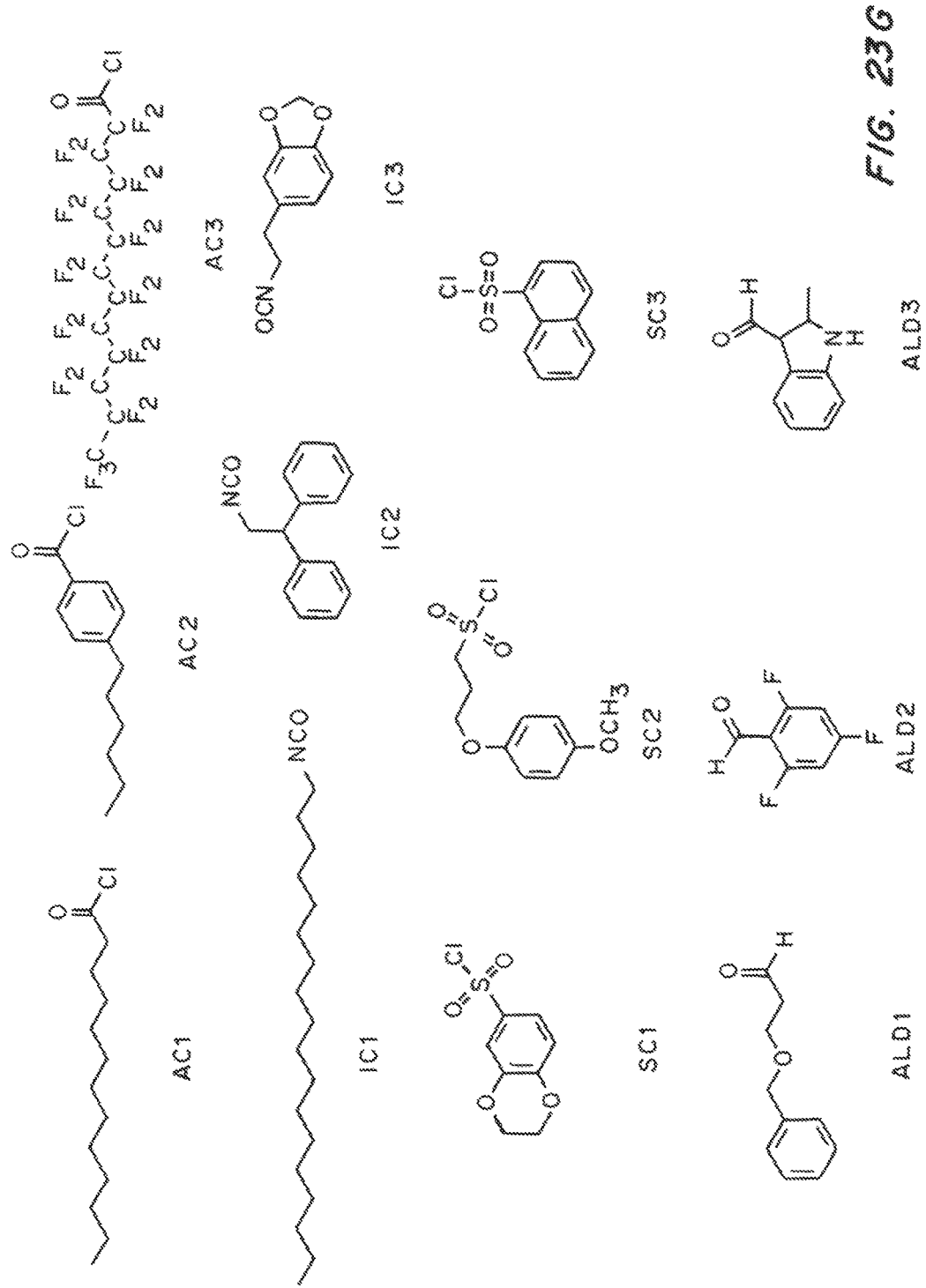

Accordingly, lower doses (0.5×) of the formulations were injected in additional groups of STZ-induced mice (FIG. 22C). While the DP3-insulin demonstrated a similar steep decrease in glucose level followed by a gradual increase (after 2 hours) towards the original glucose value, the DP3-Insulin/C12-Nitro complex continuously lowers glucose levels for more than 6 hours. Again, differences in the initial profiles of glucose level decreasing were apparent between the free DP3-insulin and its hydrophobic formulation. It is believed that the above differences between the complexed and the free forms of insulin are related to the hydrophobic interactions that resulted in slower diffusivity of the DP3-insulin from the tissue.

System glucose responsiveness can be optimized accordingly to address physiological glucose levels and the kinetics of insulin release. In order to optimize glucose responsiveness, further study is required; reversible aggregates are generated by self-associating diol-insulins encapsulated by interacting aliphatic phenylboronic acids. Destabilizing these aggregates should occur according to the dynamic alteration within blood glucose levels typical in diabetic patients (2-6 mg/dL). It is postulated that the insulin diffusion rate out of a subcutaneous injection site is a balance between complexing forces to hydrophobic interactions. PBA can complex with either glucose or insulin analogs with respect to their relative concentrations and with respect to the diol structures. The hydrophobic interaction between insulin clusters is a function of the length of the aliphatic chain, the efficiency of the conjugation to insulin, and the nature of self-associating clusters (hexamers, dimers or other forms). A study estimating the influence of tunable parameters such as the length of the aliphatic chain, the pKa of the boronic acid, the type of functionalized diols, and the number of diols per insulin can be used to engineer the system that meets the physiological window. Such studies should include developing a designated animal protocol that can help to characterize these parameters.
4. Conclusions In this study we have designed novel long acting insulins with glucose responsive properties by chemically modifying native insulin in a three-step process. Insulin was selectively modified on the B29 lysine with an alkyne. The highly efficient click chemistry allowed for fast screening of many diol structures; catechols were specifically selected for screening because of their previously shown strong affinity for complexing with PBA. Hydrophobic PBA was used for the formulations to create a long acting insulin analog. However, direct complexing between modified insulin and PBA is hindered by limited solubility and thus unsuitable for injection. This problem was solved by formulating the insulin with zinc and using a PBA with a pKa below physiological pH. The resulting hydrophobic insulin formulation was a homogeneously clear and injectable solution, and was shown to have a long acting effect with respect to non-complexed analog.

This study demonstrated the potential to make glucose responsive insulin based on PBA-diol interactions. The strength of the diol-PBA interactions, the hydrophobicity of the complex, and many other factors can be manipulated to achieve this effect. This strategy allows for rapid screening of a library of diols and PBAs, an important platform for this technology.

Example 4

Synthesis of Long-Acting Oligomer-Derivatized Insulin

This example describes a system for combinatorially generating oligomeric conjugates, attaching them to siRNA, and evaluating immunogenicity and delivery in vitro and in vivo. Using a defined set of thirteen synthetic monomers, a library of 2,197 trimeric conjugates can be made which possess unique delivery properties. This system is a high-yield and efficient oligomerization strategy that provides effective synthesis, purification, and characterization of synthetic conjugates (FIG. 24).

Figure 24A:
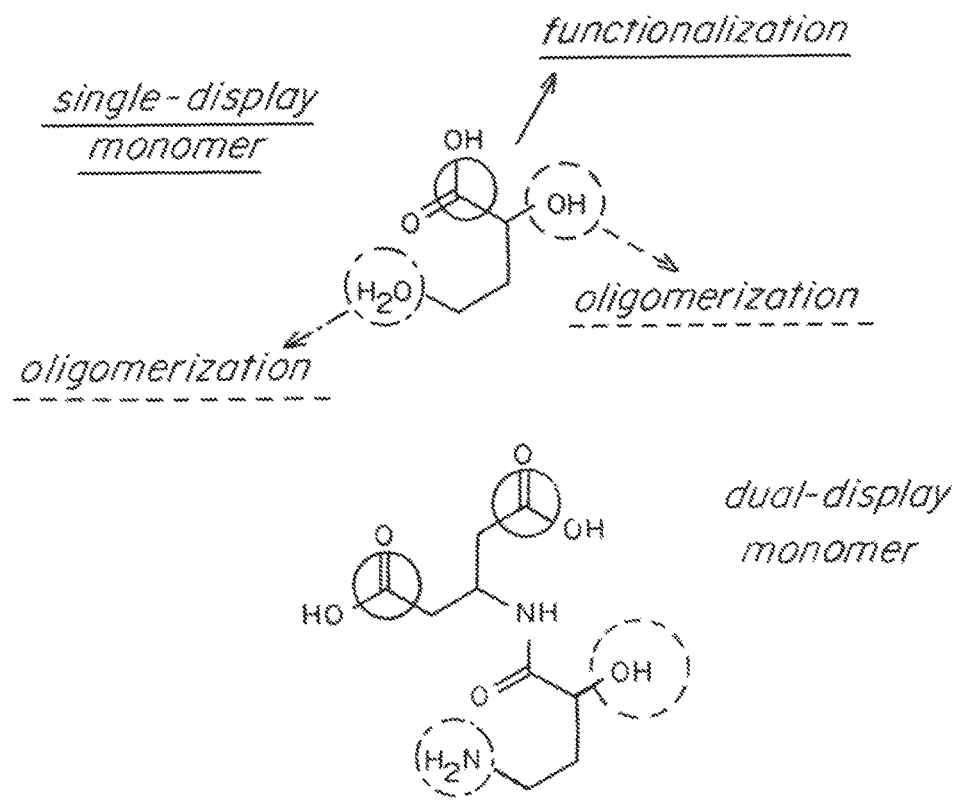
FIGS. 24A-24E are diagrams showing examples of monomer design, oligomer synthesis, and conjugation of oligomers to siRNA. (a) Amine, alcohol, and carboxylic acid moieties are used for monomer functionalization and controlled oligomerzation. Amine and alcohol moieties can be used for oligomerization, while carboxylic acid moieties are used for functionalization of the monomers. (b) Examples of delivery-relevant functionalities for monomer functionalization. (c) Representative structures of functionalized monomers. (d) Synthetic strategy used in oligomeric synthesis. (e) Successful conlugation of oligomeric sequencesto dibenzocyclooctyne siRNA utilizing copper-free Huisgen cycloaddition.
Figure 24C:
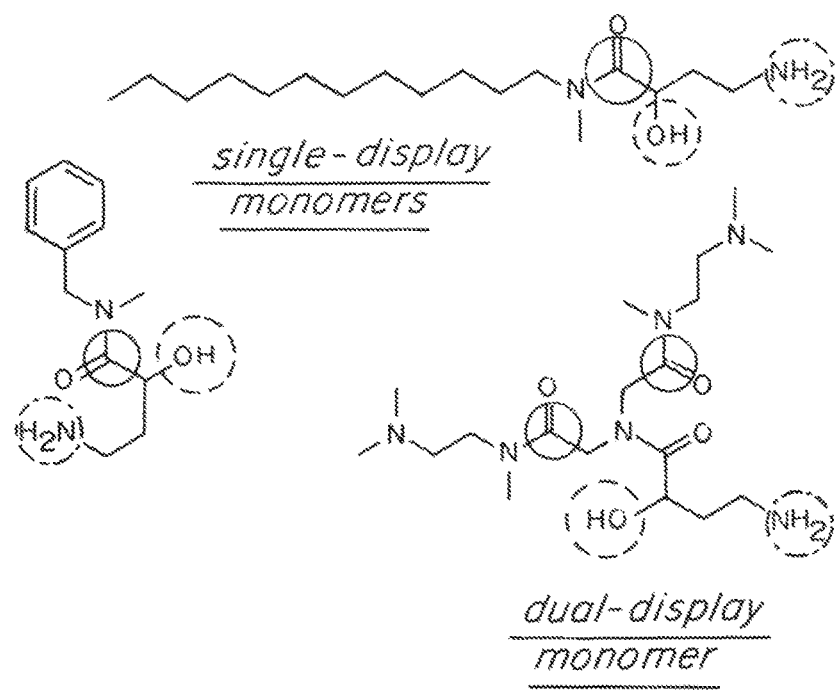
Figure 24B:
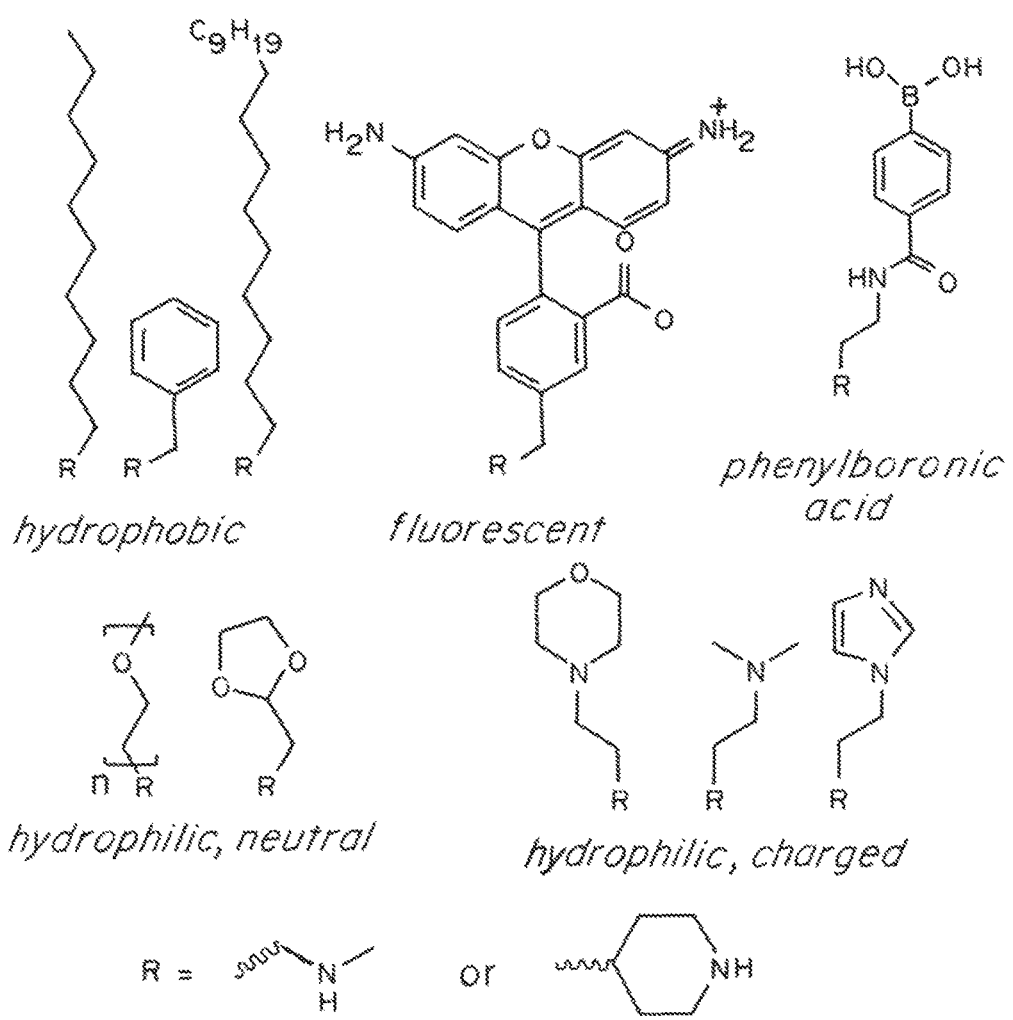
Figure 24D:
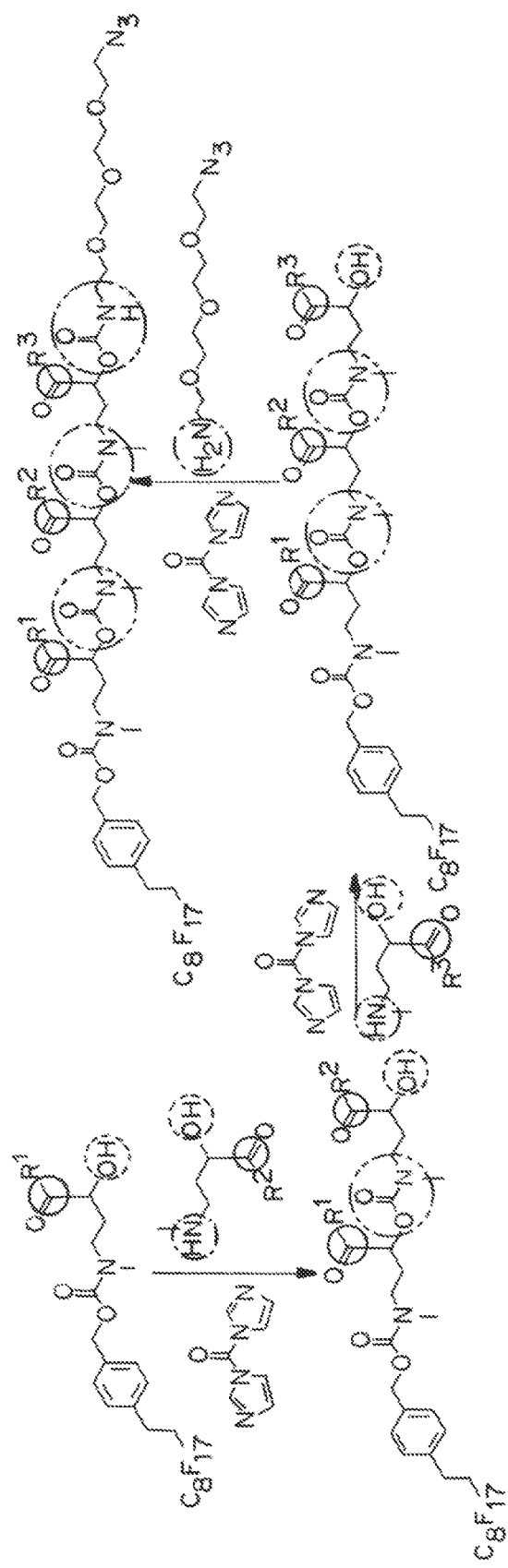

Three different chemical moieties are required on each monomer building block to ensure orthogonality between monomer functionalization and control over oligomerization. The presence of amine, alcohol, and carboxylic acid on each monomer building block allowed for attachment of delivery-biasing functionalities and oligomerization (FIGS. 24A-24C). Amidation of the carboxylic acid with delivery-biasing functionalities leaves free the alcohol and amine moieties on each monomer, which can be used for carbamate oligomerization (FIG. 24C). Carbamates are stable, non-degradable functionalities that can be synthesized using high-yielding reactions. Carbamate oligomerization using carbonyldiimidazole (CDI) is preferred because of its effectiveness (FIG. 24C). The reagent carbonyldiimidazole effectively coupled individual monomers in a controlled manner with near complete conversion as monitored by both LCMS and NMR analysis. A fluorous tag purification strategy was used, which provided isolated synthesized trimmers of 90% purity or better.

Based on nanoparticle formulations, it was discovered that certain functional groups are delivery-relevant (Table 3 and FIGS. 24A-24C). These chemical functional groups can be used to bias synthetic conjugates and ensure efficacious delivery. Acyl hydrocarbon chains have demonstrated utility in liposomal formulations and are credited with playing a major role in cellular internalization as well as endosomal membrane disruption [7, 14, 18, 21]. The inclusion of amine bases has been a cornerstone of a number of formulations for both DNA and siRNA delivery. The high pKa of most amine bases, such as tertiary and secondary amines, allows them to carry a positive charge at physiological pH, facilitating condensation with oligonucleotides, association with cellular membrane, and aiding endosomal escape [2, 7, 14, 18, 20, 21].

TABLE 3

Implicated delivery role of different functionalities.

| Functionality | Role in Delivery |
|---|---|
| hydrophobic, lipophilic | membrane association and disruption |
| amines | nucleic acid condensation, membrane association, endosomal escape |
| hydrophilic | systemic stability, cellular uptake |

It was realized from mechanistic studies that formulations with amines that have pKa's in the physiological range access different internalization pathways in vivo and have reduced toxicity than high pKa amines. Neutral and hydrophilic moieties such as PEG increase the systemic stability of nanoparticles and play a role in uptake [44]. Using these realizations as a framework, the system here functionalizes the monomers with thirteen nonpolar cyclic and acyclic hydrocarbon side chains, tertiary amines, cyclic amines with physiological pKa's, and both cyclic and acyclic neutral hydrophilic moieties. In addition, the inclusion of a fluorescent monomer can create conjugates that can be used as imaging agents of delivery.

Figure 24E:
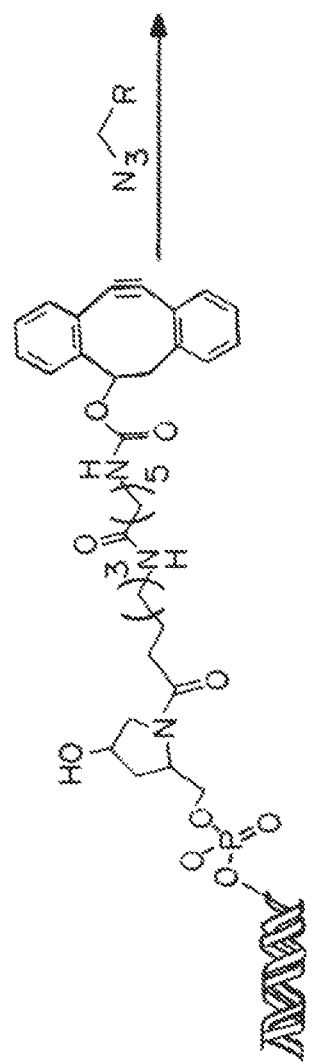
Figure 24E:
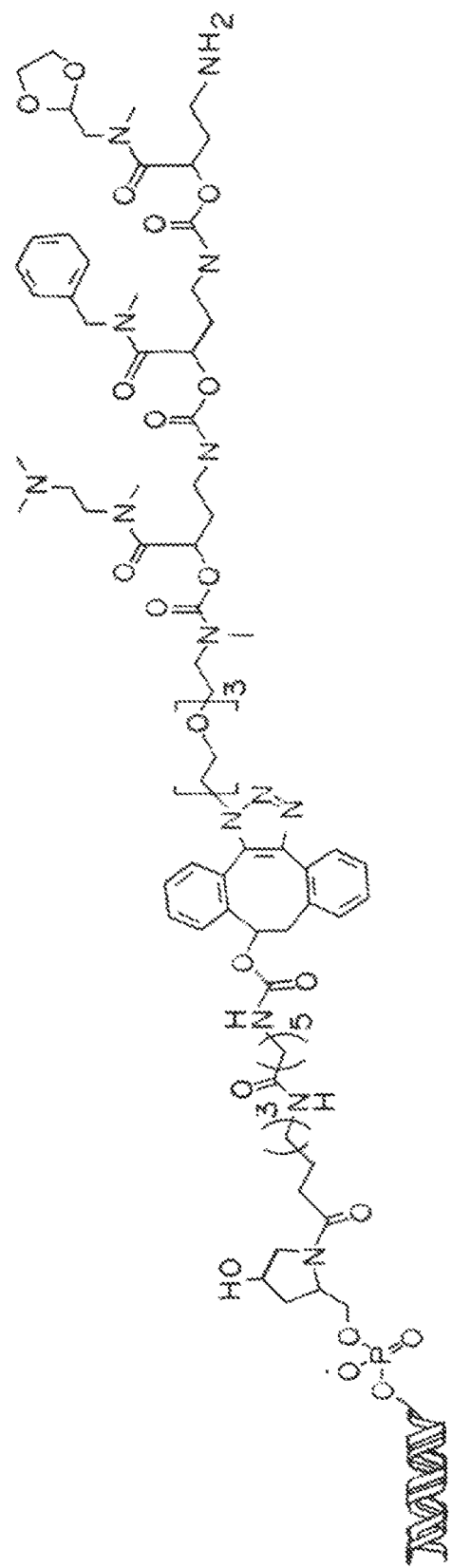

Previous studies identified the 3' end of the sense strand as an ideal location for the modification of siRNA without adversely affecting activity [11-13]. It was discovered that copper-free Huisgen cycloaddition, the coupling between cyclooctyne and azide to form stable triazine conjugation, is a high yielding and attractive method for oligomer-siRNA attachment (FIG. 24E). The alkyne-azide pair represents two chemical moieties that are inert to other chemistries making their implementation orthogonal to other reactios used for monomer functionalization and oligomerization. Amidation of siRNA bearing the 3' sense strand pyrrolidine linker with dibenzo-cyclooctyne will yield an alkyne-bearing siRNA that should easily react with azide-bearing conjugates. The only major drawback to this conjugation approach is the need to synthesize the dibenzo-cyclooctyne reagent. In a typical experiment, single-stranded dibenzo-cyclooctyne modified siRNA was reacted with azide-functionalized oligomer at two different ratios of oligomer to siRNA under RNAse-free conditions with acetonitrile as a co-solvent. The reaction mixtures were then characterized for coupling by using a gel-shift mobility assay. Successful conjugation was evident by the lowered mobility of the siRNA in the gel.

The ability of synthetic oligomers to impact delivery without adversely affecting the cellular mechanisms behind siRNA processing is dependent on conjugate size and the representation of the delivery-biasing elements. For this reason, conjugates preferably will have molecular weights much larger than small molecules but slightly smaller than the siRNA molecules themselves. To make full use of this mass range and maximize the representation of the delivery-facilitating functionalities, trimeric conjugates that contain monomers with single-modified and dual-modified sidechains are preferred (FIGS. 24A-24C).

Figure 25:
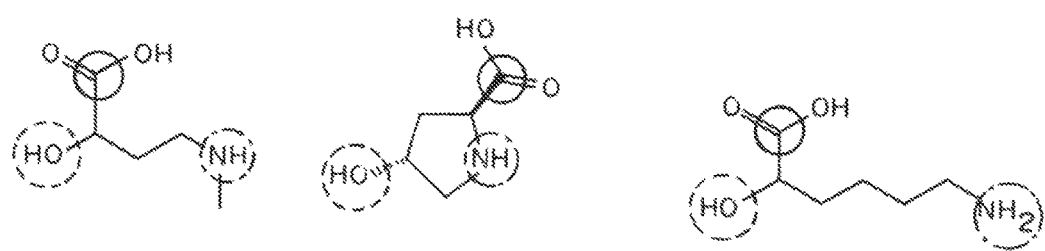
FIG. 25 is a diagram of alternative monomer backbone frameworks.
Figure 26:
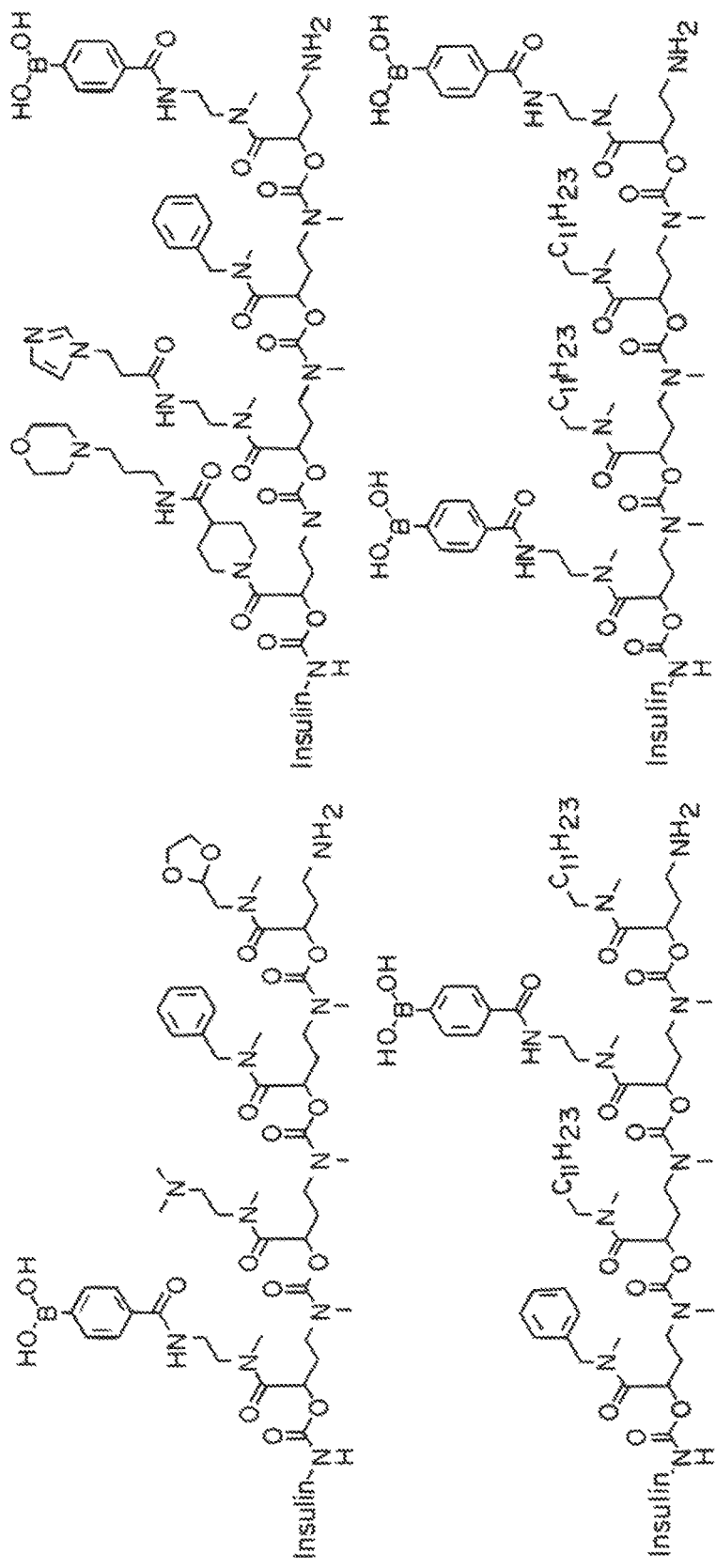
FIG. 26 is a diagram of representative oligomeric structures for conjugation to insulin.

A variety of monomer backbones (also referred to monomer building blocks) can be used to provide for more or fewer side chains and to account for reactivity differences between monomers. Some examples of alternatives are shown in FIG. 25.

The oligomer conjugates can be evaluated and optimized for efficacious siRNA delivery. For example, conjugates that display greater than 50% protein knockdown in vitro (using mouse cancer cell lines) can be tested in mice for biodistribution and endogenous gene silencing in the liver and lung. Immunogenicity can be determined by monitoring mouse cytokine levels. Oligomers displaying combinations of delivery-based functionalities will exhibit increased siRNA delivery in vitro and in vivo. Oligomer conjugates of most interest will exhibit low immunogenicity and greater than 90% protein knockdown in vivo when administered at 1 mg/kg body weight. The mechanism of oligomer-mediated siRNA delivery can be assessed in appropriate cells, such as primary mouse hepatocyte and primary mouse lung epithelial cells, by testing one or more of four different internalizations routes: clathrin-mediated endocytosis, caveolae-mediated endocytosis, charge-based cell penetration, and serum protein-mediated uptake. The oligomer conjugates can be make use of more than one delivery route, which can aid in improved and efficient delivery.

The oligomer conjugates can also be evaluated for numerous properties, such as pKa and hydrophobicity. Correlation of these properties to the effectiveness of the oligomer conjugates can be used to guide optimization of the oligomer conjugates. For example, the properties and oligomer conjugate activity can be subjected to principal component analysis (PCA) to illuminate design principles [15, 16].

The oligomer conjugates represent new means of effectively delivering siRNA to cells and tissues as well as new tools for siRNA research and development of siRNA-based therapies.

Therapeutic intervention with small-interfering RNA (siRNA) is a promising strategy for the silencing of disease-associated genes [1, 2]. Exogenous siRNA sequences can utilize the cellular mechanism of RNA interference (RNAi) to catalyze the destruction of complementary protein-encoding RNA sequences, resulting in sequence-specific gene silencing [3-6]. The prevalence of disease targets considered "undruggable" using small molecules or protein-based therapies underscores the importance of pursuing siRNA-based approaches to improve clinical outcomes for a wide range of diseases [1].

A major obstacle to implementation of siRNA therapy is systemic delivery of the oligonucleotide in vivo [7]. Polymeric or liposomal approaches have progressed towards resolving this challenge but require excess delivery material relative to siRNA, leading to issues associated with toxicity and practicality [7-14]. An alternative approach involves one-to-one modification of siRNA with chemical or biological entities that can facilitate delivery. This approach overcomes the use of excess delivery material, making it an attractive strategy to facilitate cellular delivery while minimizing unfavorable biological responses [8-10]. Conjugation of biological motifs to siRNA has achieved mixed results with limitations to clinical implementation, while small chemical entities have to date proven inefficacious [8,11,12]. Cholesterol-conjugates siRNA is the most efficacious small molecule formulation, but this approach requires doses that are intractable for therapeutic use [11-13]. Cell-penetrating peptides are efficacious in assisting delivery of payloads, but are considerably immunogenic due to the use of non-human peptides sequences [8]. To date, there are no reported investigations whether a fully synthetic, peptide-mimetic conjugate system can capture the delivery potential of large polymeric molecules while displaying low immunogenicity at therapeutically relevant doses.

Previous approaches for conjugate-mediated siRNA delivery have relied upon existing chemical or biological motifs to facilitate cellular internalization. Nanoparticle formulations are an efficacious siRNA delivery agents, but there has been no investigation into whether the chemical functionalities that facilitate efficient delivery can be translated into smaller distinct chemical entities that can serve as covalently attached conjugates.

The system described here uses these delivery-biasing chemical moieties in a synthetic oligomeric approach to develop siRNA delivery conjugates. To accommodate the numerous chemical functionalities that have been implicated in successful delivery, a defined set of delivery-biased building blocks were devised to serve as monomers, with the monomers used to build trimeric oligomers. The combinatorial pairing of delivery-relevant functionalities can generate thousands of uniqu oligomers with promising delivery potential. This approach makes generation of efficient delivery of siRNA easier and allows analysis of the structure-function relationships of the oligomers to elucidate the most salient molecular properties for efficacious delivery. This approach is the first time multiple delivery-relevant functionalities have been brought together in an oligomeric framework to identify optimal delivery agents while illuminating properties that govern delivery. Beyond their use for treatment of patients, the development of synthetic delivery conjugates are also useful tools for siRNA research and to provide understanding of chemical properties required to overcome cellular barriers.

Type 1 diabetic patients must adhere to a daily regimen of blood glucose monitoring and insulin injections to manage the disease. This management is often complicated by insufficient patient compliance [46] which leads to deregulation of their plasma glucose that can result in heart disease, hypertension, kidney failure, blindness and coma [47]. An injectable, self-regulating insulin release formulation is a promising approach to mitigate the complications resulting from poor patient compliance and improve overall life quality. Here, we propose a conjugate approach to improving the pharmacokinetic profile of insulin by achieving a controlled, self-regulating release formulation.

Native insulin injections are characterized by a lag in their therapeutic effect (30 minute delay due to self-association) and an overall short duration effect [48]. Efforts to improve these properties have resulted in both long- and short-acting insulins to treat diabetic patients, who now use both types of to maintain glycemic control [49]. Short-acting insulin is utilized prior to a meal, with long-acting insulin administered twice per day to maintain appropriate basal insulin levels in the body. Short-acting analogs are products of either covalent modification or by genetically modifying the insulin amino acid sequence (Lipsro, Aspart). These modifications reduce the hexamerization state of the insulin, increasing its bioavailability [50, 51]. Conversely, long-acting formulations promote aggregated states and have been achieved by conjugation of native insulin with protamine (NPH) or a large molar excess of zinc (Lente) [52]. Other long-acting analogs have been prepared by covalent modification with polyethylene glycol (PEG) [53, 54], fatty acids [55], (detimer) or bile acids [56]. These analogs achieve higher in vivo circulation times due to serum albumin interactions. Additionally, direct conjugation of insulin to albumin or polysaccharide chains have shown an increased circulation times [57, 58]. Finally, two other analogs are now being implemented as long-acting insulins: 1) glargine, an insulin with an increased isoelectric point (IP 6.7), is injected as an acid-soluble solution and creates an amorphous precipitate at the injection site [59], and 2) zinc-stapled insulin has an increased number of zinc binding sites causing, enhancing self-association properties [60]. Both the glargine and zinc-stapled insulin analogs were shown to diffuse slowly from the subcutaneous injection site.

Our approach is to develop a self-regulated, glucose-responsive insulin formulation through covalent modification of insulin with glucose-binding oligomeric conjugates. The introduction of phenyl-boronic acid (PBA) moieties is a well-established strategy for ensuring glucose association. The oligomeric conjugates described above are an idea platform to combinatorially determine how differing chemical functionalities alter insulin bioavailability. Our oligomers already incorporate hydrophobic, hydrophilic, and charged functionalities which previously have been demonstrated to alter insulin properties. The addition of glucose-binding moieties to our conjugates will provide a mechanism to regulate potential aggregation and serum-binding properties that oligomeric conjuates can mediate.

REFERENCES

1. Dorsett, Y.: Tuschl, T., siRNAs: applications in functional genomics and potential as therapeutics. *Nat Rev Drug Discov* 2004, 3 (4), 3-18-29.
2. Davis, M. E.; Zuckerman, J. E.; Choi, C. H.; Seligson D.; Tolcher, A.; Alabi, C. A.; Yen, Y.; Heidel, J. D.; Ribas, A., Evidence of RNAi in humans from systemically administered siRNA via targeted nanoparticles. *Nature* 464 (7291), 1067-70,
3. Caplen, N. J.; Parrish, S.; Imani, F.; Fire, A.; Morgan, R. A., Specific inhibition of gene expression by small double-stranded RNAs in invertebrate and vertebrate systems. *Pro Natl Acad Sci USA* 2001, 98 (17), 9742-7.
4. Elbashir, S. M.; Harborth, J.; Lendeckel, W.; Yalcin, A.; Weber, K.;
Tuschl, T., Duplexes of 21-nucleotide RNAs mediate RNA interference in cultured mammalian cells. *Nature* 2001, 411 (6836), 494-8.
5. Hannon, G. J.; Rossi, J. J.; Unlocking the potential of the human genome with RNA interference. *Nature* 2004, 431 (7006), 371-8.
6. McManus, M. T.; Sharp, P. A., Gene silencing in mammals by small interfering RNAs. *Nat Rev Genet* 2002, 3 (10), 737-47.
7. Whitehead, K. A.; Langer, R.; Anderson, D. G., Knocking down barriers: advances in siRNA delivery. *Nat Rev Drug Discov* 2009, 8 (2), 129-38.
8. Jeong, J. H.; Mok, H.; Oh, Y. K.; Park, T. G., siRNA conjugate delivery systems. *Bioconjug Chem* 2009, 20 (1), 5-14.
9. Stanton, M. G.; Colletti, S. L., Medicinal Chemistry of siRNA Delivery. *J Med Chem.*
10. Vaishnaw, A. K.; Gollob, J.; Gamba-Vitalo, C.; Hutabarat, R.; Sah, D.; Meyers, R.; de Fougerolles, T.; Maraganore, J., A status report on RNAi therapeutics. *Silence* 1 (I), 14.
11. Lorenz, C.; Hadwiger, P.; John, M.; Vornlocher, H. P.; Unverzagt, c., Steroid and lipid conjugates of siRNAs to enhance cellular uptake and gene silencing in liver cells. *Bioorg Med Chem Lett* 2004, 14 (19), 4975-7.
12. Soutschek, J.; Akinc, A.; Bramlage, B.; Charisse, K.; Constien, R.; Donoghue, M.; Elbashir, S.; Geick, A.; Hadwiger, P.; Harborth, J.; John, M.; Kesavan, V.; Lavine, G.; Pandey, R. K.; Racie, T.; Rajeev, K. G.; Rohl, I.; Toudjarska, I.; Wang, G.; Wuschko, S.; Bumcrot, D.; Koteliansky, V.; Limmer, S.; Manoharan, M.; Vornlocher, H. P., Therapeutic silencing of an endogenous gene by systemic administration of modified siRNAs. *Nature* 2004, 432 (7014), 173-8.
13. Wolfrum, C.; Shi, S.; Jayaprakash, K. N.; Jayaraman, M.; Wang, G.; Pandey, R. K.; Rajeev, K. G.; Nakayama, T.; Charrise, K.; Ndungo, E, M.; Zimmermann, T.; Koteliansky, V.; Manoharan, M.; Stoffel, M., Mechanisms and optimization of in vivo delivery of lipophilic siRNAs. *Nat Biotechnol* 2007, 25 (10), 1149-57.
14. Schroeder, A.; Levins, C. G.; Cortez, C.; Langer, R.; Anderson. D. G., Lipid-based nanotherapeutics for siRNA delivery. *J Intern Med* 267 (I), 9-21
15. Leonard, J. T.; Roy, K., QSAR by LFER model of HIV protease inhibitor mannitol derivatives using FA-MLR, PCRA, and PLS techniques. *Bioorg Med Chem* 2006, 14 (4), 1039-46.
16. XU, Q.; Ni, S.; Wu, F.; Liu, F.; Ye, X.; Mougin, B.; Meng, Xc; Du, X., Investigation of Variation in Gene Expression Profiling of Human Blood by Extended Principle Component Analysis. *PLoS One* 6 (10), e26905.
17. Akinc, A.; Querbes, W.; De, S.; Qin, J.; Frank-Kamenetsky, M.; Jayaprakash, K. N.; Jayaraman, M.; Rajeev, K. G.; Cantley, W. L.; Dorkin, J. R.; Butler, J. S.; Qin, L.; Raeie, T.; Sprague, A.; Fava, E.; Zeigerer, A.; Hope, M. J.; Zenal, M.; Sah, D. W.; Fitzgerald, K.; Tracy, M. A; Manoharan, M.; Koteliansky, V.; Fougerolles, A.; Maier, M. A., Targeted delivery of RNAi therapeutics with endogenous and exogenous ligand-based mechanisms. *Mol Ther* 18 (7), 1357-64.
18. Akinc, A.; Zumbuehl, A; Goldberg, M.; Leshchiner, E. S.; Busini, V.; Hossain, N.; Bacallado, S. A.; Nguyen, D. N.; Fuller, J.; Alvarez, R.; Borodovsky, A; Borland, T.; Constien. R.; de Fougerolles. A.; Dorkin, J. R.; Narayanannair Jayaprakash, K.; Jayaraman, M.; John, M.; Koteliansky, V.; Manoharan, M.; Nechev, L.; Qin, J.; Racie, T.; Raitcheva, D.; Rajeev, K. G.; Sah, D. W.; Soutschek, J.; Toudjarska, I.; Vomlocher, H. P.; Zimmermann, T. S.; Langer, R.; Anderson, D. G., A combinatorial library of lipid-like materials for delivery of RNAi therapeutics. *Nat Biotechnol* 2008, 26 (5), 561-9.
19. Love, K. T.; Mahon, K. P.; Levins, C. G.; Whitehead, K. A.; Querbes, W.; Dorkin, J. R.; Qin, J.; Cantley, W.; Qin, L. L.; Racie, T.; Frank-Kamenetsky, M.; Yip, K. N.; Alvarez, R.; Sah, D. W.; de Fougerolles, A.; Fitzgerald, K.; Koteliansky, V.; Akinc, A.; Langer, R.; Anderson, D. G., Lipid-like materials for low-dose, in vivo gene silencing. *Proc Natl Acad Sci USA* 107 (5), 1864-9.
20. Mahon, K. P.; Love, K. T.; Whitehead, K. A.; Qin J.; Akinc, A.; Leshchiner, E.; Leshchiner, I.; Langer, R.; Anderson, D. G., Combinatorial approach to determine functional group effects on lipidoid-mediated siRNA delivery. *Bioconjug Chem* 21 (8), 1448-54.
21. Semple, S. C.; Akinc, A.; Chen, J.; Sandhu, A. P.; Mui, B. I.; Cho, C. K.; Sah, D. W.; Stebbing, D.; Crosley, E. J.; Yaworski, E.; Hafez, I. M.; Dorkin, J. R.; Qin, J.; Lam, K.; Rajeev, K. G.; Wong, K. F.; Jeffs, L. B.; Nechev, L.; Eisenhardt, M. L.; Jayararnan, M.; Kazem, M.; Maier, M. A.; Srinivasulu, M.; Weinstein, M. J.; Chen, Q.; Alvarez, R.; Barros, S. A.; De, S.; Klimuk, S. K.; Borland, T.; Kosovrasti, V.; Cantley, W. L.; Tam, Y. K.; Manoharan, M.; Ciufolini, M. A.; Tracy, M. A.; de Fougerolles, A.; MacLachlan, I.; Cullis, P. R; Madden, T. D.; Hope, M. J., Rational design of cationic lipids for siRNA delivery. *Nat Biotechnol* 28 (2), 172-6.
22. Rozema, D. B.; Lewis, D. L.; Wakefield, D. H.; Wong, S. c.; Klein, J. J.; Roesch, P. L.; Bertin, S. L.; Reppen, T. W.; Chu, Q.; Blokhin, A. V.; Hagstrom, J. E.; Wolff, J. A., Dynamic PolyConjugates for targeted in vivo delivery of siRNA to hepatocytes. *Proc Nat. Acad Sci USA* 2007, 104 (32), 12982-7.
23. Astriab-Fisher, A.; Sergueev, D.; Fisher, M.; Shaw, B. R.; Juliano, R. L., Conjugates of antisense oligonucleotides with the Tat and antennapedia cell-penetrating peptides: effects on cellular uptake; binding to target sequences, and biologic actions. *Pharm Res* 2002, 19 (6), 744-54.
24. Astriab-Fisher, A.; Sergueev, D. S.; Fisher, M.; Shaw, B. R; Juliano, R. 1., Antisense inhibition of P-glycoprotein expression using peptide-oligonucleotide conjugates. *Biochem Pharmacol* 2000, 60 (I), 83-90.
25. Chiu, Y. L.; Ali, A.; Chu, C. Y.; Cao, H.; Rana, T. M., Visualizing a correlation between siRNA localization, cellular uptake, and RNAi in living cells. *Chem Biol* 2004, 11 (8), 1165-75.

26. Davidson, T. J.; Harel, S.; Arboleda, V. A.; Prunell, G. F.; Shelanski, M. L.; Greene, L. A.; Troy, C. M., Highly efficient small interfering RNA delivery to primary mammalian neurons induces MicroRNA-like effects before mRNA degradation. *J Neurosci* 2004, 24 (45), 10040-6.

27. Kim, D. H.; Behlke, M. A.; Rose, S. D.; Chang, M. S.; Choi, S.; Rossi, J. J., Synthetic dsRNA Dicer substrates enhance RNAi potency and efficacy. *Nat Biotechnol* 2005, 23 (2), 222-6.

28. Lindgren, M.; Hallbrink, M.; Prochiantz, A.; Langel, U., Cell-penetrating peptides. *Trends Pharmacol Sci* 2000, 21 (3), 99-103.

29. Moschos, S. A.; Jones, S. W.; Perry, M. M.; Williams, A. E.; Etjefalt, J. S.; Turner, J. J.; Barnes, P. J.; Sproat, B. S.; Gait, M. J.; Lindsay, M. A., Lung delivery studies using siRNA conjugated to TAT(48-60) and penetratin reveal peptide induced reduction in gene expression and induction of innate immunity. *Bioconjug Chem* 2007, 18 (5), 1450-9.

30. Muratovska, A.; Eccles, M. R., Conjugate for efficient delivery of short interfering RNA (siRNA) into mammalian cells. *FEBS Lett* 2004, 558 (1-3), 63-8.

31. Pooga, M.; Hallbrink, M.; Zorko, M.; Langel, U., Cell penetration by transportan. *FASEB J* 1998, 12 (I), 67-77.

32. Prochiantz, A., [Messenger proteins] *J Soc Biol* 2000, 194 (3-4), 119-23.

33. Tripathi, S.; Cbaubey, B.; Ganguly, S.; Harris, D.; Casale, R. A.; Pandey, V. N., Anti-HIV-I activity of anti-TAR polyamide nucleic acid conjugated with various membrane transducing peptides. *Nucleic Acids Res* 2005, 33 (13), 4345-56.

34. Turner, J. J.; Arzumanov, A. A.; Gait, M. J., Synthesis, cellular uptake and HIV-I Tat-dependent trans-activation inhibition activity of oligonucleotide analogues disulphide-conjugated to cell-penetrating peptides. *Nucleic Acids Res* 2005, 33 (I), 27-42.

35. Turner, J. J.; Ivanova, G. D.; Verbeure, B.; Williams, D.; Arzumanov, A. A.; Abes, S.; Lebleu, B.; Gait, M. J., Cell-penetrating peptide conjugates of peptide nucleic acids (PNA) as inhibitors of HIV-1 Tat-dependent trans-activation in cells. *Nucleic Acids Res* 2005, 33 (21), 6837-49.

36. Vives, E.; Brodin, P.; Lebleu, B., A truncated HIV-I Tat protein basic domain rapidly translocates through the plasma membrane and accumulates in the cell nucleus. *J Biol Chem* 1997, 272 (25), 16010-7.

37. Cesarone, G.; Edupuganti, O. P.; Chen, C. P.; Wickstrom, E., Insulin receptor substrate 1 knockdown in human MCF7 ER+ breast cancer cells by nuclease-resistant IRS 1 siRNA conjugated to a disulfide-bridged D-peptide analogue of insulin-like growth factor I. *Bioconjug Chem* 2007, 18 (6), 1831-40.

38. Ikeda, Y.; Taira, K., Ligand-targeted delivery of therapeutic siRNA. *Pharm Res* 2006, 23 (8), 1631-40.

39. Wu, G.; Yang, W.; Barth, R. F.; Kawabata, S.; Swindall, M.; Bandyopadhyaya, A. K.; Tjarks, W.; Khorsandi, B.; Blue, T. E.; Ferketich, A. K.; Yang, M.; Christoforidis, G. A.; Sferra, T. J.; Binns, P. J.; Riley, K. J.; Ciesielski, M. J.; Fenstennaker, R. A., Molecular targeting and treatment of an epidermal growth factor receptor-positive glioma using boronated cetuximab. *Clin Cancer Res* 2007, 13 (4), 1260-8.

40. Chu, T. C.; Twu, K. Y; Ellington, A. D.; Levy, M., Aptamer mediated siRNA delivery. *Nucleic Acids Res* 2006, 34 (10), e73.

41. Hicke, B. J.; Stephens, A. W., Escort aptamers: a delivery service for diagnosis and therapy. *J Clin Invest* 2000, 106 (8), 923-8.

42. Xia, C. F.; Zhang, Y.; Boado, R. J.; Pardridge, W. M., Intravenous siRNA of brain cancer with receptor targeting and avidin-biotin technology. *Pharm Res* 2007, 24 (12), 2309-16.

43. Zhang, Y.; Zhang, Y. F.; Bryant, J.; Charles, A.; Boado, R. J.; Pardridge, W. M., Intravenous RNA interference gene therapy targeting the human epidermal growth factor receptor prolongs survival in intracranial brain cancer. *Clin Cancer Res* 2004, 10 (11), 3667-77.

44. Harris, J. M.; Martin, N. E.; Modi, M., Pegylation: a novel process for modifying pharmacokinetics. *Clin Pharmacokinet* 2001, 40 (7), 539-51.

45. Yamada, T.; Peng, C. G.; Matsuda, S.; Addepalli, H.; Jayaprakash, K. N.; Alam, M. R.: Mills, K.; Maier, M. A.; Charisse, K.; Sekine, M.; Manoharan, M.; Rajeev, K. G., Versatile site-specific conjugation of small molecules to siRNA using click chemistry. *J Org Chem* 76 (5), 1198-211.

46. Cramer, J. A.; Pugh, M. J., The influence of insulin use on glycemic control: How well do adults follow prescriptions for insulin? *Diabetes Care* 2005, 28 (Copyright (C) 2012 U.S. National Library of Medicine.), 78-83.

47. Browning, J. D.; Szczepaniak, L. S.; Dobbins, R.; Nuremberg, P.; Horton, J. D.; Cohen, J. C.; Grundy. S. M.; Hobbs, H. H., Prevalence of hepatic steatosis in an urban population in the United States: Impact of ethnicity. *Hepatology* 2004, 40 (6), 1387-1395.

48. Berman, M., Insulin kinetics, models, and delivery schedules. *Diabetes Care* 1980, 3 (Copyright (C) 2012 American Chemical Society (ACS). All Rights Reserved.), 266-9.

49. Esposito, K.; Giugliano, D., Current insulin analogues in the treatment of diabetes: emphasis on type 2 diabetes. *Expert Opin. Biol. Ther.* 2012, 12 (Copyright (C) 2012 American Chemical Society (ACS). All Rights Reserved.), 209-221.

50. Siddiqui, N. I., Insulin analogues: new dimension of management of diabetes mellitus. *Mymensingh Med J* 2007, 16 (Copyright (C) 2012 U.S. National Library of Medicine.), 117-21.

51. Helms, K. L.; Kelley, K. W.; Insulin glulisine: an evaluation of its pharmacodynamic properties and clinical application. *Ann. Pharmacother.* 2009, 43 (Copyright (C) 2012 American Chemical Society (ACS). All Rights Reserved.), 658-668.

52. Gerich, J. E., Novel insulins: expanding options in diabetes management. *Am. J. Med.* 2002, 113 (Copyright (C) 2012 American Chemical Society (ACS). All Rights Reserved.), 308-316.

53. Hinds, K.; Koh, J. J.; Joss, L.; Liu, F.; Baudys, M.; Kim, S. W., Synthesis and Characterization of Poly(ethylene glycol)-Insulin Conjugates. *Bioconjugate Chem.* 2000, 11 (Copyright (C) 2012 American Chemical Society (ACS). All Rights Reserved.), 195-201.

54. Shechter, Y.; Mironchik, M.; Rubinraut, S.; Tsubery, H.; Sasson, K.; Marcus, Y.; Fridkin, M., Reversible pegylation of insulin facilitates its prolonged action in vivo. *Eur. J. Pharm. Biopharm.* 2008, 70 (Copyright (C) 2012 American Chemical Society (ACS). All Rights Reserved.), 19-28.

55. Szypowska, A.; Golicki, D.; Groele, L.; Pankowska, E., Long-acting insulin analogue detemir compared with NPH Insulin in type 1 diabetes. A systematic review and meta-analysis. *Pol. Arch. Med. Wewn*, 2011, 121 (Copyright (C) 2012 American Chemical Society (ACS). All Rights Reserved.), 237-246.
56. Lee, S.; Kim, K.; Xumar, T. S; Lee, J.; Kim, S. K.; Lee, D. Y.; Lee, Y.-k.; Byun, Y., Synthesis and biological properties of insulin-deoxycholic acid chemical conjugates. *Bioconjugate Chem.* 2005, 16 (Copyright (C) 2012 American Chemical Society (ACS). All Rights Reserved.), 615-620.
57. Shechter, Y.; Mironchik, M.; Rubinraut, S.; Saul, A.; Tsubery, H.; Fridkin, M., Albumin-insulin conjugate releasing insulin slowly under physiological conditions: a new concept for long-acting insulin. *Bioconjugate Chem.* 2005, 16 (Copyright (C) 2012 American Chemical Society (ACS). All Rights Reserved.), 913-920.
58. Baudys, M.; Letourneur, D.; Liu, F.; Mix, D.; Jozefonvicz, J.; Kim, S. W., Extending Insulin Action in Vivo by Conjugation to Carboxymethyl Dextran. *Bioconjugate Chem.* 1998, 9 (Copyright (C) 2012 American Chemical Society (ACS). All Rights Reserved.), 176-183.
59. Gerich, J. E., Insulin glargine: long-acting basal insulin analog for improved metabolic control. *Curr. Med. Res. Opin.* 2004, 20 (Copyright (C) 2012 American Chemical Society (ACS). All Rights Reserved.), 31-37.
60. Phillips, N. B.; Wan, Z.-I.; Whittaker, L.; Hu, S.-Q.; Huang, K.; Hua, Q.-x.; Whittaker, J.; Ismail-Beigi, F.; Weiss, M. A., Supramolecular Protein Engineering: Design of Zinc-stapled Insulin Hexamers as a Long Acting Depot. *J. Biol. Chem.* 2010, 285 (Copyright (C) 2012 American Chemical Society (ACS). All Rights Reserved.), 11755-11759.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An insulin conjugate having the formula:

$X_1$-$X_2$ wherein $X_1$ is insulin, an insulin analog, glucagon, GLP-1, or a GLP-1 agonist,
$X_2$ is:
(i) —CO—$(CH_2)_j$—NH—CO—$CR_1R_2$,
wherein j is an integer from 3-25
$R_1$ is —NH—$R_{12}$ or —NH—CO—$CH_2$—$CH_2$—$CNR_{12}$—$C(O)R_{32}$, where $R_{32}$ is glucamine, gluconic acid, glucosamine, fructosamine, galactosamine, mannosamine, or other hexosamines,
$R_{12}$ is selected from the group consisting of hydrogen, —$SO_2$alkyl, —$SO_2$cycloalkyl, —$SO_2$heterocycloalkyl, —$SO_2$aryl, —$SO_2$heteroaryl, —COalkyl, —COcycloalkyl, —COheterocycloalkyl, —COaryl, —COheteroaryl, —CONHalkyl, —CONHcycloalkyl, —CONHheterocycloalkyl, —CONHaryl, —CONHheteroaryl,
wherein alkyl, cycloalkyl, heterocycloalkyl, aryl, and heteroaryl groups are substituted or unsubstituted,
$R_2$ is —$(CH_2)_n$—NH—CO—$R_{11}$ or —$(CH_2)_n$—NH—$SO_2R_{11}$, n is an integer from 3-25, and
$R_{11}$ is an organic borate group;
(ii) an oligomer comprising a plurality of monomers, wherein the monomers comprise a side chain, wherein the side chain comprises one or more organic borate groups, hydrophobic groups, hydrophilic neutral groups, hydrophilic charged groups, diol groups, fluorescent groups, and combinations thereof, wherein at least one of the side chains comprises an organic borate group;
(iii) —CO—$R_6$—$R_7$,
wherein $R_6$ is a linker or is not present,
wherein $R_7$ is a diol-containing group complexed to a hydrophobic organic borate group, wherein the diol-containing group comprises one or more diols, wherein the hydrophobic organic borate group comprises one or more organic borate groups covalently linked to a hydrophobic group, wherein at least one diol and one hydrophobic organic borate group form a boronic ester; or
(iv) —CO—$R_8$, wherein $R_8$ is:
(a) -alkenyl-$R_9$, wherein $R_9$ is a phenylboronic acid group, wherein the alkenyl group can be substituted or unsubstituted, wherein the number of carbons in the alkenyl group is from 3 to 25,
(b) —$R_{13}$, wherein $R_{13}$ is a bile acid, wherein one or more hydroxyls on the bile acid are derivatized with an organic borate group, or
(c) —$(CH_2)_r$—NH—CO—$CHR_{14}$—NH—CO—$(CH_2)_s$, wherein r is an integer from 3-25, wherein s is an integer from 3-25, wherein $R_{14}$ is an amine-containing group comprising an organic borate group.

2. The derivatized insulin of claim 1, wherein n is 4.

3. The derivatized insulin of claim 1, wherein each monomer residue of the oligomer is —CO—O—$R_3$—, wherein $R_3$ is:
—$CR_4$—$(CH_2)_m$—NH— or pyrrolidine substituted with $R_4$, wherein m is an integer from 0-25,
wherein $R_4$ is —CO—NH—$R_5$ or —CO—NH—C(CH—CO—NH—$R_5)_2$,
wherein each $R_5$ is independently:
(a) an organic borate group,
(b) $C_{8-18}$ alkyl,
(c) —$CH_2$-phenyl,
(d) —$(CH_2$—$CH_2$—O$)_p$—H or —$(CH_2$—$CH_2$—O$)_p$—$CH_3$, wherein p is an integer from 1-500,
(e) —$CH_2$-dioxane,
(f) —$CH_2$—$CH_2$-oxazane,
(g) —$CH_2$—$CH_2$—N($CH_2$—$CH_3)_2$,
(h) —$CH_2$—$CH_2$-pyrazole,
(i) a fluorescent group,
(j) -piperidine-phenyl,
(k) -piperidine-oxazane,
(l) -piperidine-$CH_2$—$CH_2$—N($CH_2$—$CH_3)_2$,
(m) -piperidine-$CH_2$—$CH_2$-pyrazole,
(n) -dimethylaminobenzyl, or
(o) -pyridine,
wherein at least one $R_s$ is a phenylboronic acid group.

4. An insulin conjugate having the formula:

$X_1$-$X_2$ wherein $X_1$ is insulin, an insulin analog, glucagon, GLP-1, or a GLP-1 agonist,
$X_2$ is:
(i) —CO—$(CH_2)_j$—NH—CO—$CR_1R_2$,
wherein j is an integer from 3-25

$R_1$ is —NH—$R_{12}$ or —NH—CO—$CH_2$—$CH_2$—$CNR_{12}$—C(O)$R_{32}$, where $R_{32}$ is glucamine, gluconic acid, glucosamine, fructosamine, galactosamine, mannosamine, or other hexosamines, $R_{12}$ is selected from the group consisting of hydrogen, —$SO_2$alkyl, —$SO_2$cycloalkyl, —$SO_2$heterocycloalkyl, —$SO_2$aryl, —$SO_2$heteroaryl, —COalkyl, —COcycloalkyl, —COheterocycloalkyl, —COaryl, —COheteroaryl, —CONHalkyl, —CONHcycloalkyl, —CONHheterocycloalkyl, —CONHaryl, —CONHheteroaryl, wherein alkyl, cycloalkyl, heterocycloalkyl, aryl, and heteroaryl groups are substituted or unsubstituted, $R_2$ is —$(CH_2)_n$—NH—CO—$R_{11}$ or —$(CH_2)_n$—NH—$SO_2R_{11}$, n is an integer from 3-25, and $R_{11}$ is an organic borate group;

(ii) an oligomer comprising a plurality of monomers, wherein the monomers comprise a side chain, wherein the side chain comprises one or more organic borate groups, hydrophobic groups, hydrophilic neutral groups, hydrophilic charged groups, diol groups, fluorescent groups, and combinations thereof, wherein at least one of the side chains comprises an organic borate group;

(iii) —CO—$R_6$—$R_7$, wherein $R_6$ is a linker or is not present, wherein $R_7$ is a diol-containing group complexed to a hydrophobic organic borate group, wherein the diol-containing group comprises one or more diols, wherein the hydrophobic organic borate group comprises one or more organic borate groups covalently linked to a hydrophobic group, wherein at least one diol and one hydrophobic organic borate group form a boronic ester; or (iv) —CO—$R_8$, wherein $R_8$ is:

(a) -alkenyl-$R_9$, wherein $R_9$ is a phenylboronic acid group, wherein the alkenyl group can be substituted or unsubstituted, wherein the number of carbons in the alkenyl group is from 3 to 25, (b) —$R_{13}$, wherein $R_{13}$ is a bile acid, wherein one or more hydroxyls on the bile acid are derivatized with an organic borate group, or (c) —$(CH_2)_r$—NH—CO—$CHR_{14}$—NH—CO—$(CH_2)_s$, wherein r is an integer from 3-25, wherein s is an integer from 3-25, wherein $R_{14}$ is an amine-containing group comprising an organic borate group, wherein the diol-containing group is -(DOPA-Gly)$_i$—$NH_2$, wherein i is an integer from 1-5.

5. The derivatized insulin of claim 1, wherein the diol-containing group is 6-methyl-6-deoxy-D-galactose, 1-deoxy-β-D-lactopyranoside, α-D-Mannopyranosyl, or adenosine.

6. An insulin conjugate having the formula:

$X_1$-$X_2$ wherein $X_1$ is insulin, an insulin analog, glucagon, GLP-1, or a GLP-1 agonist, $X_2$ is:

(i) —CO—$(CH_2)_j$—NH—CO—$CR_1R_2$, wherein j is an integer from 3-25

$R_1$ is —NH—$R_{12}$ or —NH—CO—$CH_2$—$CH_2$—$CNR_{12}$—C(O)$R_{32}$, where $R_{32}$ is glucamine, gluconic acid, glucosamine, fructosamine, galactosamine, mannosamine, or other hexosamines, $R_{12}$ is selected from the group consisting of hydrogen, —$SO_2$alkyl, —$SO_2$cycloalkyl, —$SO_2$heterocycloalkyl, —$SO_2$aryl, —$SO_2$heteroaryl, —COalkyl, —COcycloalkyl, —COheterocycloalkyl, —COaryl, —COheteroaryl, —CONHalkyl, —CONHcycloalkyl, —CONHheterocycloalkyl, —CONHaryl, —CONHheteroaryl, wherein alkyl, cycloalkyl, heterocycloalkyl, aryl, and heteroaryl groups are substituted or unsubstituted, $R_2$ is —$(CH_2)_n$—NH—CO—$R_{11}$ or —$(CH_2)_n$—NH—$SO_2R_{11}$, n is an integer from 3-25, and $R_{11}$ is an organic borate group;

(ii) an oligomer comprising a plurality of monomers, wherein the monomers comprise a side chain, wherein the side chain comprises one or more organic borate groups, hydrophobic groups, hydrophilic neutral groups, hydrophilic charged groups, diol groups, fluorescent groups, and combinations thereof, wherein at least one of the side chains comprises an organic borate group;

(iii) —CO—$R_6$—$R_7$, wherein $R_6$ is a linker or is not present, wherein $R_7$ is a diol-containing group complexed to a hydrophobic organic borate group, wherein the diol-containing group comprises one or more diols, wherein the hydrophobic organic borate group comprises one or more organic borate groups covalently linked to a hydrophobic group, wherein at least one diol and one hydrophobic organic borate group form a boronic ester; or (iv) —CO—$R_8$, wherein $R_8$ is:

(a) -alkenyl-$R_9$, wherein $R_9$ is a phenylboronic acid group, wherein the alkenyl group can be substituted or unsubstituted, wherein the number of carbons in the alkenyl group is from 3 to 25, (b) —$R_{13}$, wherein $R_{13}$ is a bile acid, wherein one or more hydroxyls on the bile acid are derivatized with an organic borate group, or (c) —$(CH_2)_r$—NH—CO—$CHR_{14}$—NH—CO—$(CH_2)_s$, wherein r is an integer from 3-25, wherein s is an integer from 3-25, wherein $R_{14}$ is an amine-containing group comprising an organic borate group, wherein $R_6$ is —$(CH_2)_h$—$R_{31}$—, wherein h is an integer from 3-25, wherein $R_{31}$ is O-triazole- or CO—NH—$CH_2$—CO-dibenzo-cyclocta-triazole-.

7. An insulin conjugate having the formula:

$X_1$-$X_2$ wherein $X_1$ is insulin, an insulin analog, glucagon, GLP-1, or a GLP-1 agonist, $X_2$ is:

—CO—$(CH_2)_j$—NH—CO—$CR_1R_2$, wherein j is an integer from 3-25

$R_1$ is —NH—$R_{12}$ or —NH—CO—$CH_2$—$CH_2$—$CNR_{12}$—C(O)$R_{32}$, where $R_{32}$ is glucamine, gluconic acid, glucosamine, fructosamine, galactosamine, mannosamine, or other hexosamines, $R_{12}$ is selected from the group consisting of hydrogen, —$SO_2$alkyl, —$SO_2$cycloalkyl, —$SO_2$heterocycloalkyl, —$SO_2$aryl, —$SO_2$heteroaryl, —COalkyl, —COcycloalkyl, —COheterocycloalkyl, —COaryl, —COheteroaryl, —CONHalkyl, —CONHcycloalkyl, —CONHheterocycloalkyl, —CONHaryl, —CONHheteroaryl, wherein alkyl, cycloalkyl, heterocycloalkyl, aryl, and heteroaryl groups are substituted or unsubstituted, $R_2$ is —$(CH_2)_n$—NH—CO—$R_{11}$ or —$(CH_2)_n$—NH—$SO_2R_{11}$, n is an integer from 3-25, and $R_{11}$ is an organic borate group;

(ii) an oligomer comprising a plurality of monomers, wherein the monomers comprise a side chain, wherein the side chain comprises one or more organic borate groups, hydrophobic groups, hydrophilic neutral groups, hydrophilic charged groups, diol groups, fluorescent groups, and combinations thereof, wherein at least one of the side chains comprises an organic borate group;

(iii) —CO—$R_6$—$R_7$ wherein $R_6$ is a linker or is not present, wherein $R_7$ is a diol-containing group complexed to a hydrophobic organic borate group, wherein the diol-containing group comprises one or more diols, wherein the hydrophobic organic borate group comprises one or more organic borate groups covalently linked to a hydrophobic group, wherein at least one diol and one hydrophobic organic borate group form a boronic ester, or (iv) —CO—$R_8$, wherein $R_8$ is:

(a) -alkenyl-$R_9$, wherein $R_9$ is a phenylboronic acid group, wherein the alkenyl group can be substituted or unsubstituted, wherein the number of carbons in the alkenyl group is from 3 to 25, (b) —$R_{13}$, wherein $R_{13}$ is a bile acid, wherein one or more hydroxyls on the bile acid are derivatized with an organic borate group, or (c) —$(CH_2)_r$—NH—CO—$CHR_{14}$—NH—CO—$(CH_2)_s$, wherein r is an integer from 3-25, wherein s is an integer from 3-25, wherein $R_{14}$ is an amine-containing group comprising an organic borate group, wherein the hydrophobic group is —$(CH2)_k$—$CH_3$, wherein k is an integer from 3-25.

8. The derivatized insulin of claim 7, wherein k is 11.

9. The derivatized insulin of claim 1, wherein the hydrophobic group is a bile acid.

10. The derivatized insulin of claim 1, wherein q is 11.

11. The derivatized insulin of claim 1, wherein the bile acid is cholic acid, lithocholic acid, hyocholic acid, deoxycholic acid, hyodeoxycholic acid, or chenodeoxycholic acid.

12. The derivatized insulin of claim 1, wherein $R_{14}$ is —$(CH_2)_t$—$R_{30}$, wherein $R_{30}$ is the phenylboronic acid group, and wherein t is an integer from 3-25.

13. The derivatized insulin of claim 1, wherein r is 3 and s is 6, 8, 10, 12, or 14.

14. The derivatized insulin of claim 1, wherein r is 5 and s is 6, 8, 10, 12, or 14.

15. The derivatized insulin of claim 1, wherein r is 11 and s is 6, 8, 10, 12, or 14.

16. The derivatized insulin of claim 1, wherein r+s is an integer from 13 to 21.

17. The derivatized insulin of claim 1, wherein each organic borate group has the formula:

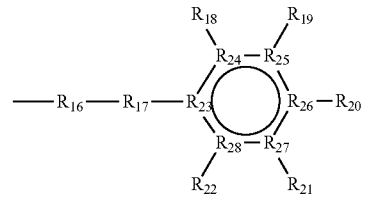

wherein $R_{16}$ is NH, $NR_{29}$, or is not present, wherein $R_{17}$ is $CH_2$, CO, $SO_2$, or is not present, wherein $R_{18}$, $R_{19}$, $R_{20}$, $R_{21}$, and $R_{22}$ are each independently —$B(OH)_2$, —F, —$NO_2$, —CN, —H, or not present, wherein only one of $R_{18}$, $R_{19}$, $R_{20}$, $R_{21}$, and $R_{22}$ is —$B(OH)_2$, wherein $R_{23}$, $R_{24}$, $R_{25}$, $R_{26}$, and $R_{27}$ are each independently C or N, wherein at most only three of $R_{23}$, $R_{24}$, $R_{25}$, $R_{26}$, and $R_{27}$ are N, wherein $R_{28}$ is C, and wherein $R_{29}$ is $C_{1-4}$ alkyl.

18. A method of alleviating one or more symptoms of diabetes comprising administering to a diabetic subject an effective amount of the derivatized insulin of claim 1.

* * * * *

UNITED STATES PATENT AND TRADEMARK OFFICE
CERTIFICATE OF CORRECTION

| | | |
|---|---|---|
| PATENT NO. | : 9,867,869 B2 | Page 1 of 1 |
| APPLICATION NO. | : 14/652011 | |
| DATED | : January 16, 2018 | |
| INVENTOR(S) | : Daniel G. Anderson et al. | |

It is certified that error appears in the above-identified patent and that said Letters Patent is hereby corrected as shown below:

On the Title Page

(72) Inventors, replace "Michael J. Webber" with "Matthew J. Webber"

In the Claims

Column 55, Line 50, replace "(CH2)1" with "(CH.sub.2).sub.j."
Column 56, Line 36, delete "residue"
Column 56, Line 59, "R5" is unclear
Column 59, Line 41, replace "(CH2).sub.k" with "(CH.sub.2).sub.k"
Column 60, Line 1, replace "q" with "n"
Column 60, "R23" in the drawing is unclear Signed and Sealed this
Twenty-second Day of May, 2018

Andrei Iancu
*Director of the United States Patent and Trademark Office*